United States Patent
Esvelt et al.

(10) Patent No.: US 10,526,618 B2
(45) Date of Patent: Jan. 7, 2020

(54) RNA-GUIDED GENE DRIVES

(71) Applicant: President and Fellows of Harvard College, Cambridge, MA (US)

(72) Inventors: Kevin M. Esvelt, Auburndale, MA (US); Andrea L. Smidler, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/172,645

(22) Filed: Jun. 3, 2016

(65) Prior Publication Data
US 2016/0333376 A1    Nov. 17, 2016

Related U.S. Application Data

(63) Continuation of application No. PCT/US2015/010550, filed on Jan. 8, 2015.

(60) Provisional application No. 62/024,642, filed on Jul. 15, 2014, provisional application No. 61/924,735, filed on Jan. 8, 2014.

(51) Int. Cl.
| | |
|---|---|
| *C12N 9/90* | (2006.01) |
| *C12N 15/90* | (2006.01) |
| *C12N 15/63* | (2006.01) |
| *C12N 15/10* | (2006.01) |
| *C12N 9/22* | (2006.01) |

(52) U.S. Cl.
CPC .............. *C12N 15/905* (2013.01); *C12N 9/22* (2013.01); *C12N 15/102* (2013.01); *C12N 15/63* (2013.01); *C12N 15/902* (2013.01)

(58) Field of Classification Search
None
See application file for complete search history.

(56) References Cited

U.S. PATENT DOCUMENTS

| | | |
|---|---|---|
| 2005/0120395 A1 | 6/2005 | Burt |
| 2012/0315670 A1* | 12/2012 | Jacobson ............ C12N 15/1051 435/69.1 |
| 2013/0326645 A1 | 12/2013 | Cost et al. |
| 2015/0159174 A1 | 6/2015 | Frendewey et al. |
| 2015/0159175 A1* | 6/2015 | Frendewey .......... C12N 15/907 435/462 |

FOREIGN PATENT DOCUMENTS

| | | |
|---|---|---|
| WO | 2013/126794 A1 | 8/2013 |
| WO | 2013/131920 A1 | 9/2013 |
| WO | 2013/141680 A1 | 9/2013 |
| WO | WO-2013/131920 * | 9/2013 |
| WO | 2013/176772 A1 | 11/2013 |
| WO | 2013188638 A2 | 12/2013 |
| WO | 2013192278 A1 | 12/2013 |

OTHER PUBLICATIONS

Windbichler et al ("A synthetic homing endonuclease-based gene drive system in the human malaria mosquito." (Nature, May 12, 2011, vol. 473, pp. 212-2015 published online Apr. 20, 2011).*
Basset & Liu, (published online Dec. 18, 2013, "CRISPR/Cas9 and Genome Editing in *Drosophila*" Journal of Genetics and Genomics vol. 41 (2014) pp. 7-19).*
Burt et al (Proc R Soc Lond B (2003) 270, pp. 921-928).*
Champer et al, "Cheating evolution: engineering gene drives to manipulate the fate of wild populations" Nature Reviews: Genetics, Mar. 2016, vol. 17, pp. 146-159. (Year: 2016).*
International Search Report issued from corresponding PCT/US2015/010550, dated May 11, 2015.
Esvelt, Kevin M. et al., "Genome-scale engineering for systems and synthetic biology", Molecular Systems Biology. vol. 9, No. 1, Jan. 22, 2013, pp. 1-17.
Windbichler, Nikolai et al., "A synthetic homing endonuclease-based gene drive system in the human malaria mosquito", Nature, Nature Publishing Group, United Kingdon, vol. 473, No. 7346, May 12, 2011, pp. 212-215.
Jao, Li-En, et al., "Efficient multiplex biallelic zebrafish genome editing using a CRISPR nuclease system", Proceedings of the National Academy of Sciences, vol. 110, No. 34, Aug. 5, 2013, pp. 13904-13909.
Esvelt, Kevin M. et al., "Emerging Technology: Concerning RNA-guided gene drives for the alteration of wild populations", ELIFE, vol. 3, Jul. 17, 2014, pp. 1-21.
Oct. 19, 2017—European Search Report—EP 15735409.3.
Japanese Office Action issued for JP 2016-545854 dated Feb. 19, 2019.
Jinek, Martin et al., "A Programmable Dual-RNA-Guided DNA Endonuclease in Adaptive Bacterial Immunity". Science, Aug. 2012, vol. 337, pp. 816-821, Supplementary Materials.

* cited by examiner

*Primary Examiner* — Catherine S Hibbert
(74) *Attorney, Agent, or Firm* — Banner & Witcoff, Ltd.

(57) ABSTRACT

RNA guided Cas9 gene drives and method for their use are disclosed.

25 Claims, 29 Drawing Sheets

Specification includes a Sequence Listing.

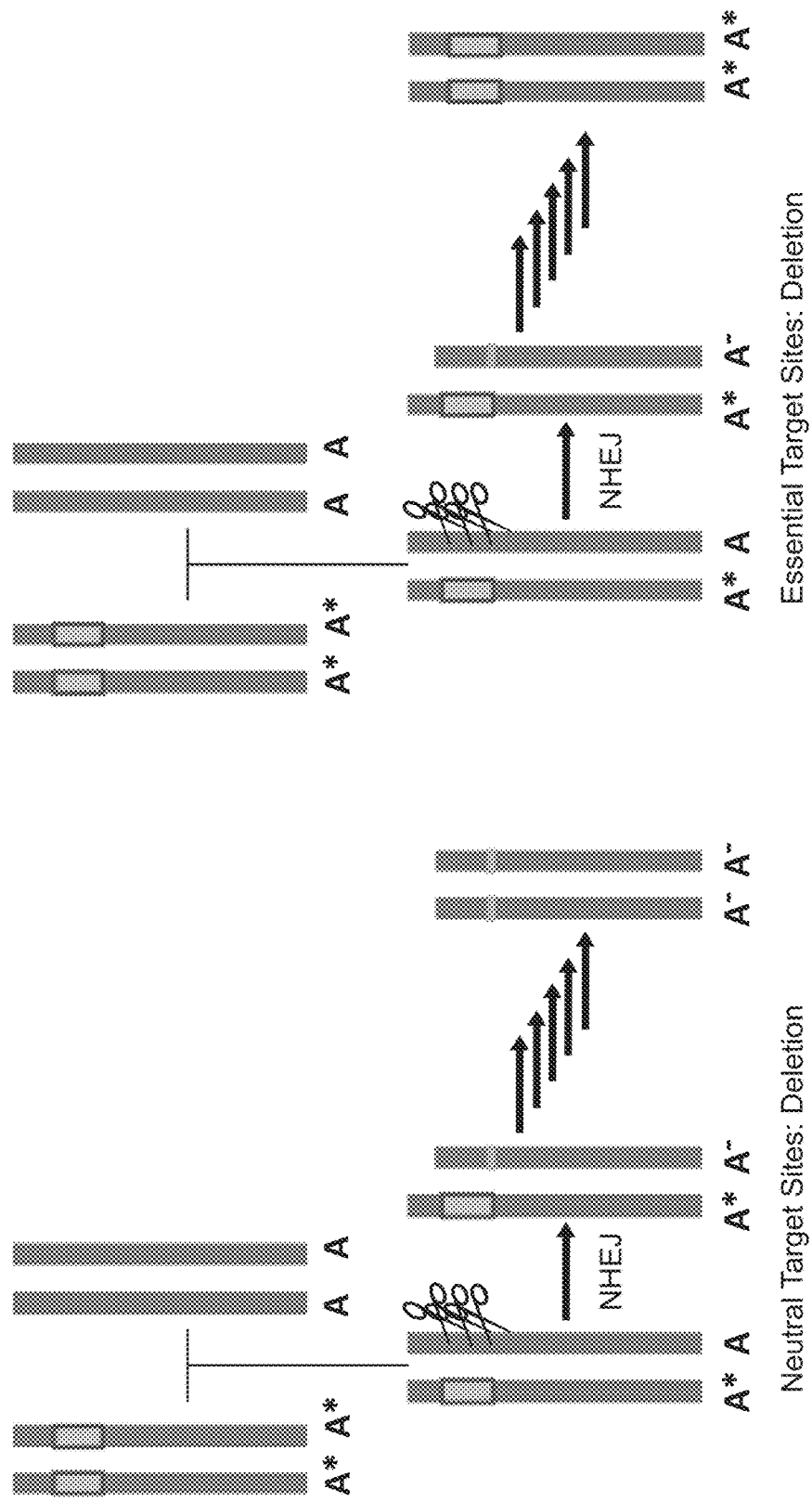

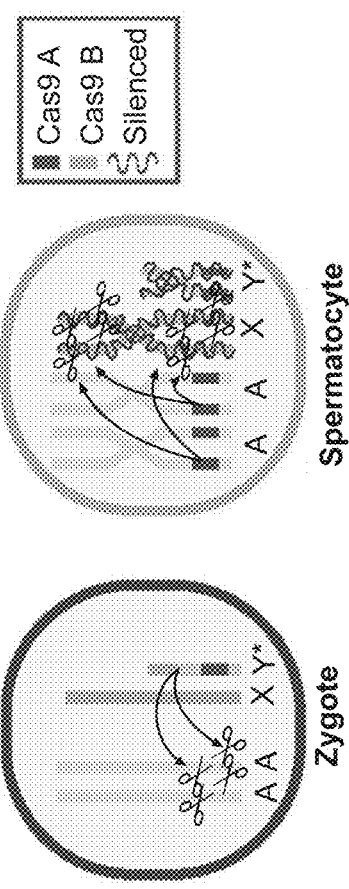
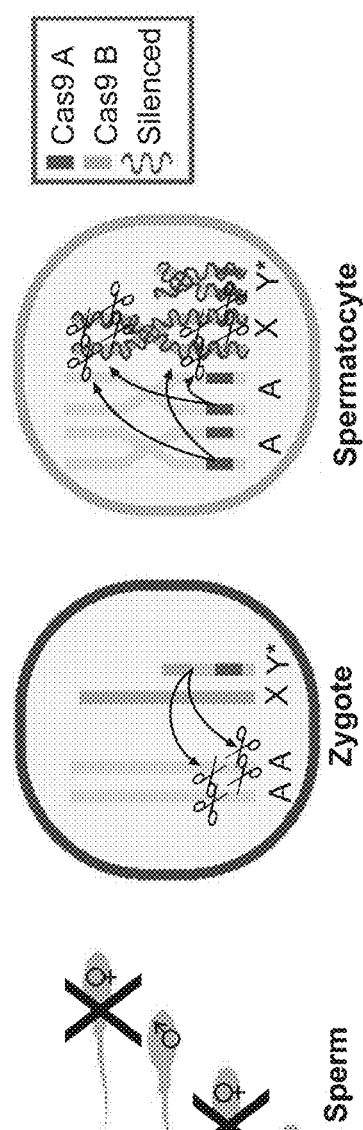
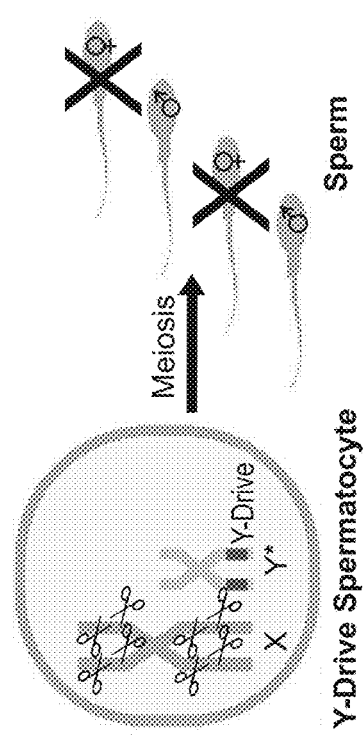
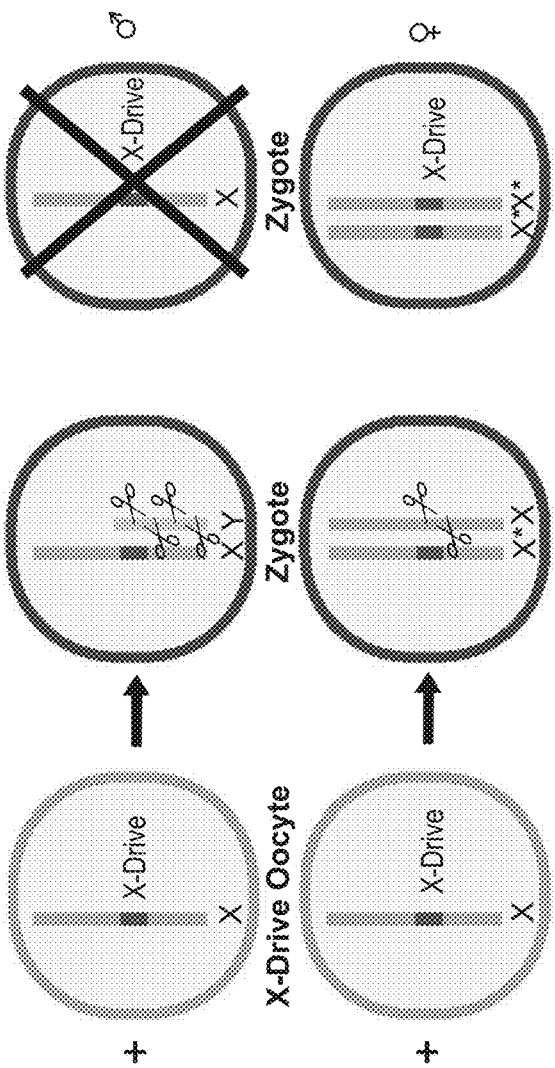
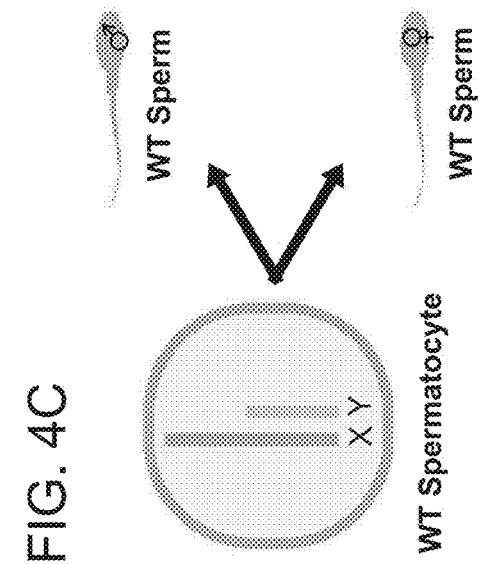
FIG. 4A
FIG. 4B
FIG. 4C

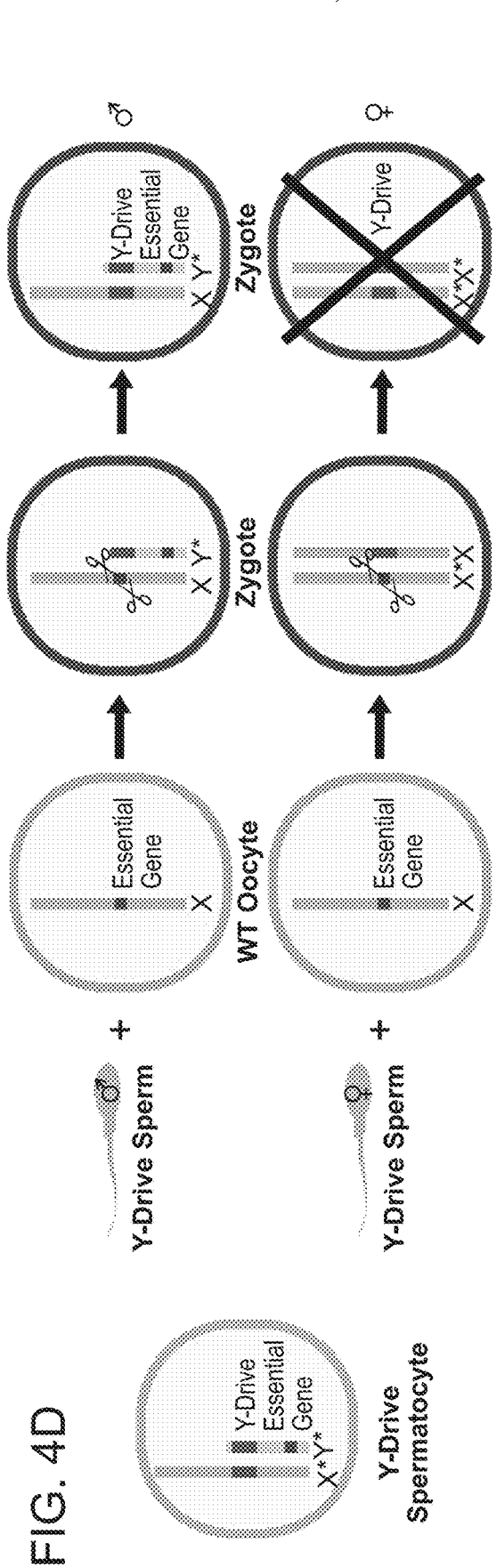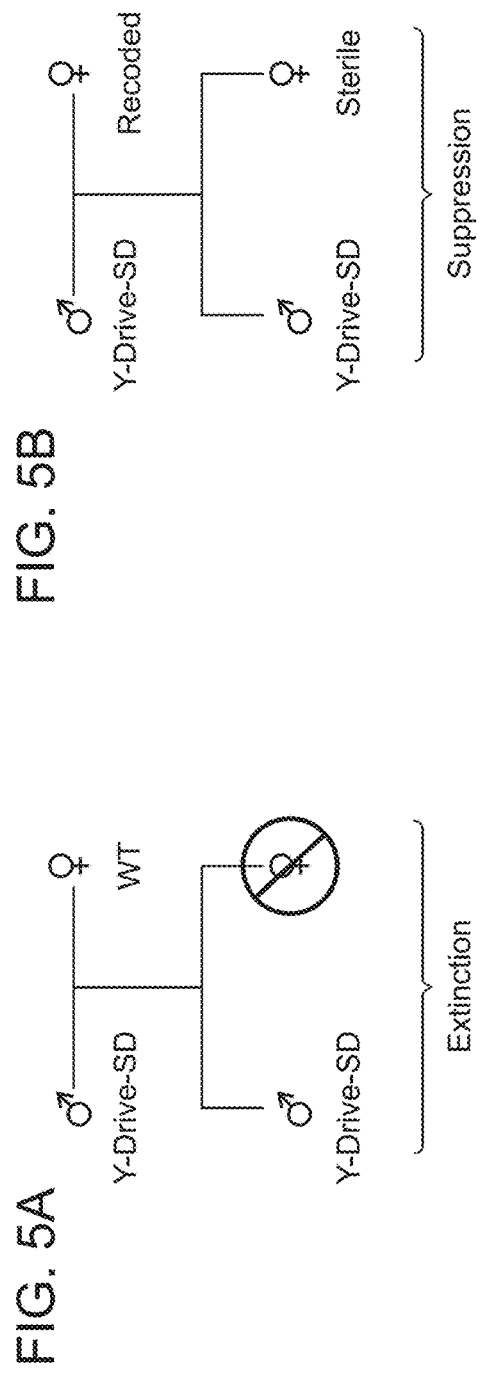
FIG. 4D
FIG. 5A
FIG. 5B

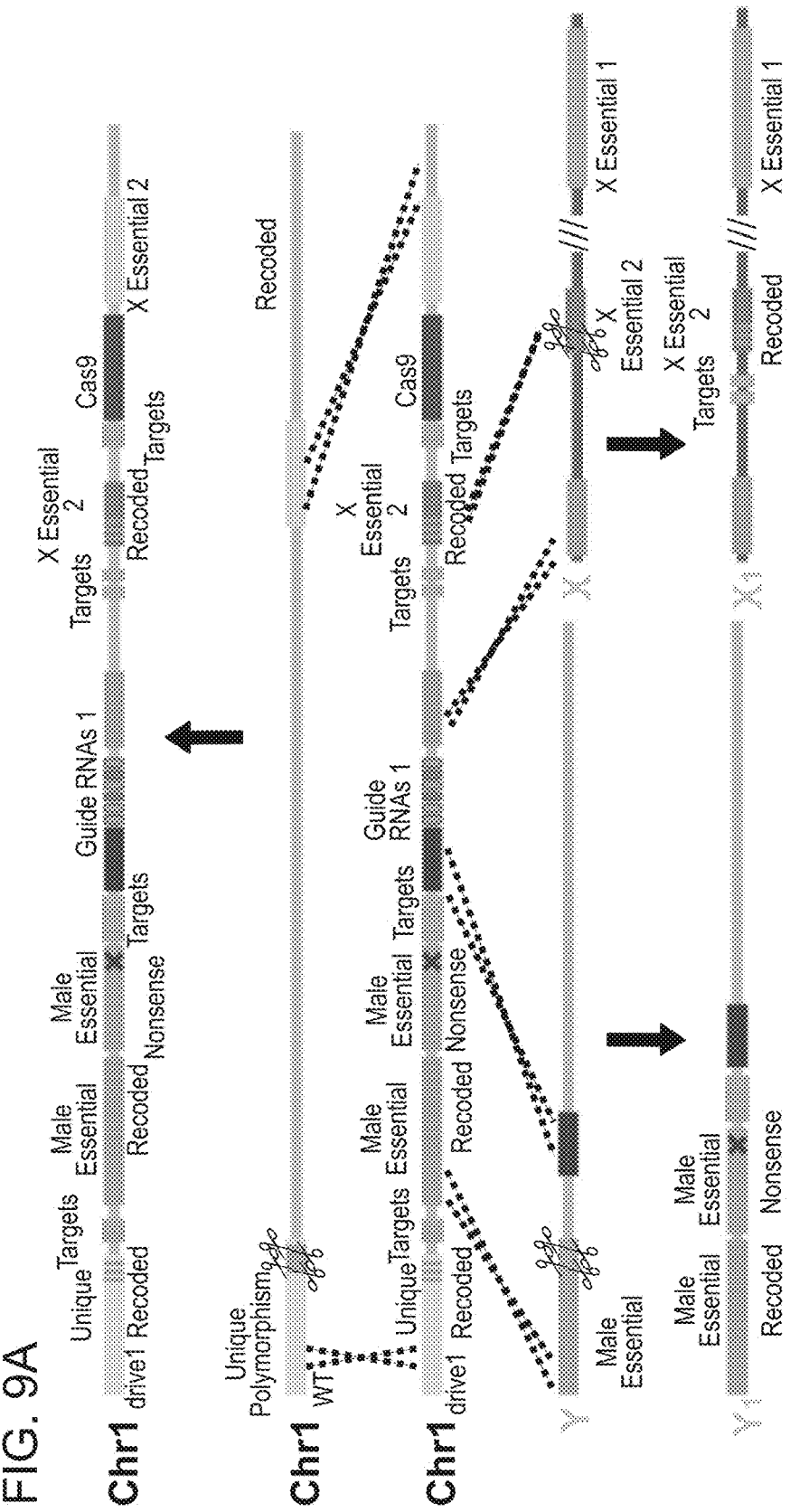

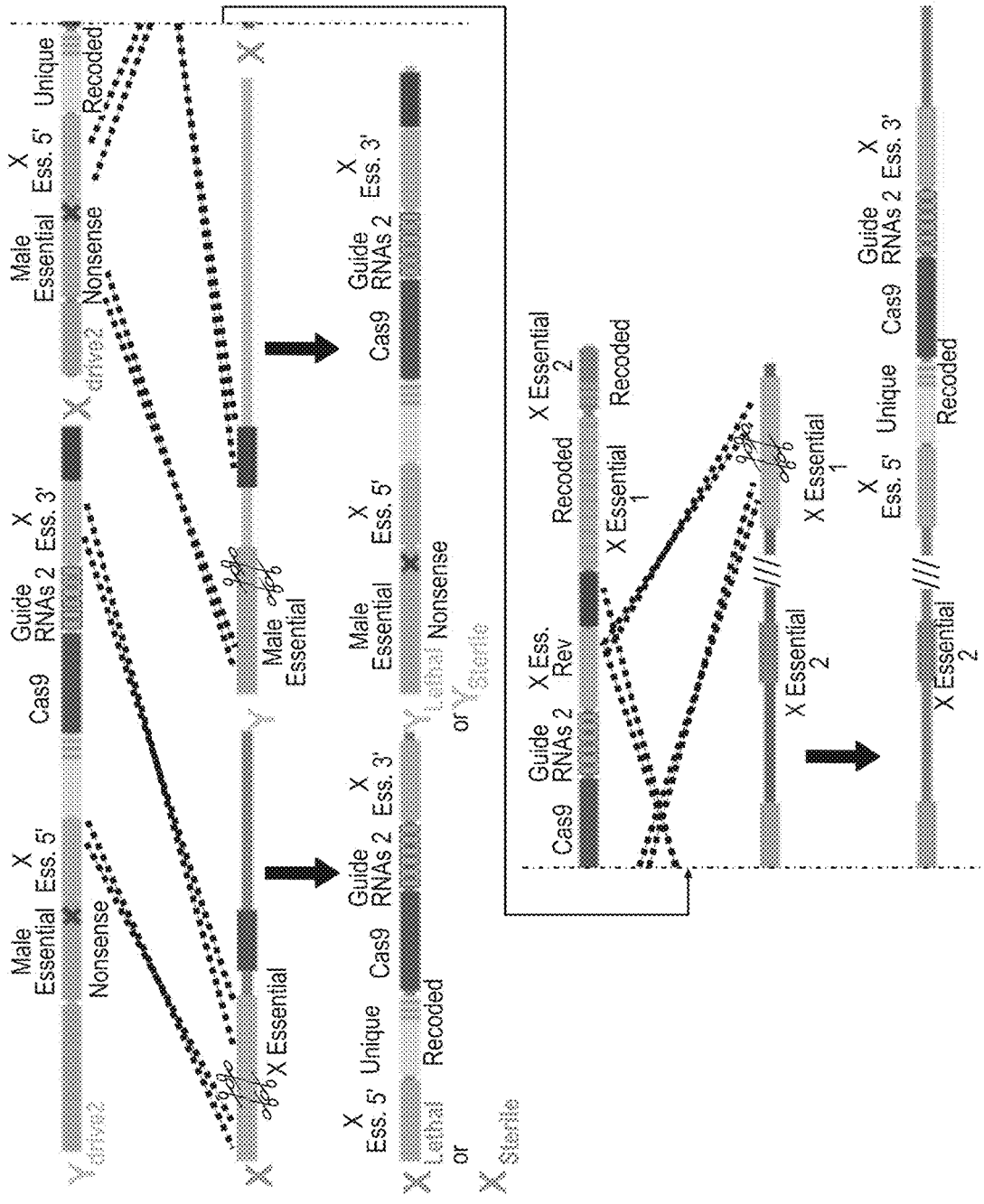

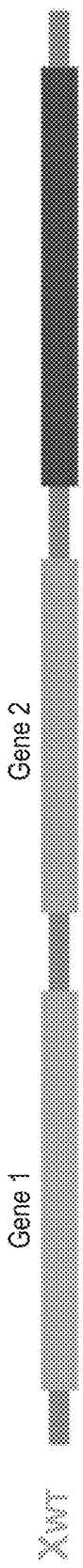
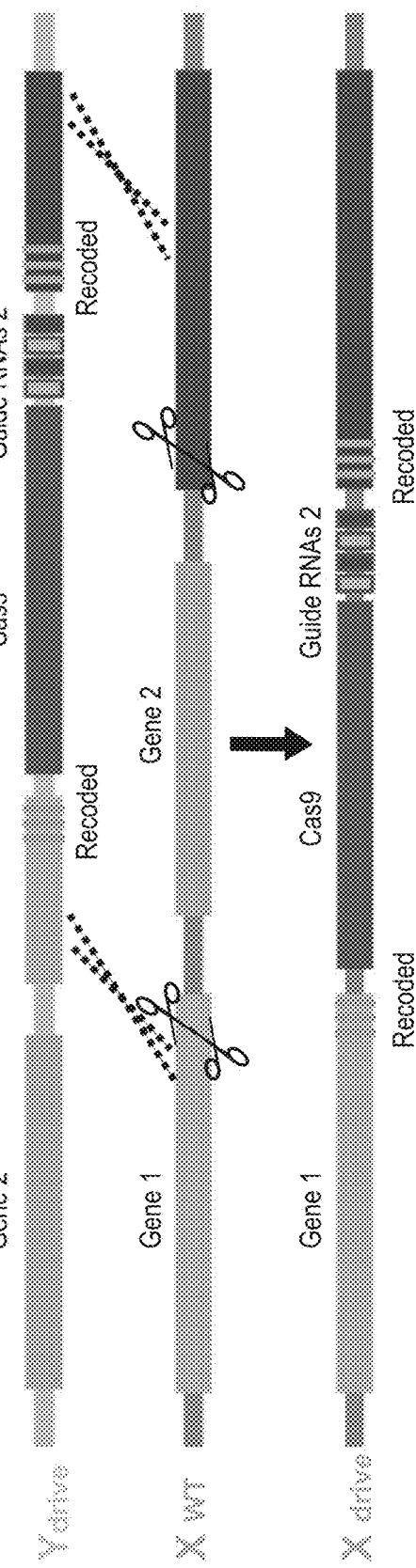
FIG. 10A
FIG. 10B
FIG. 10C

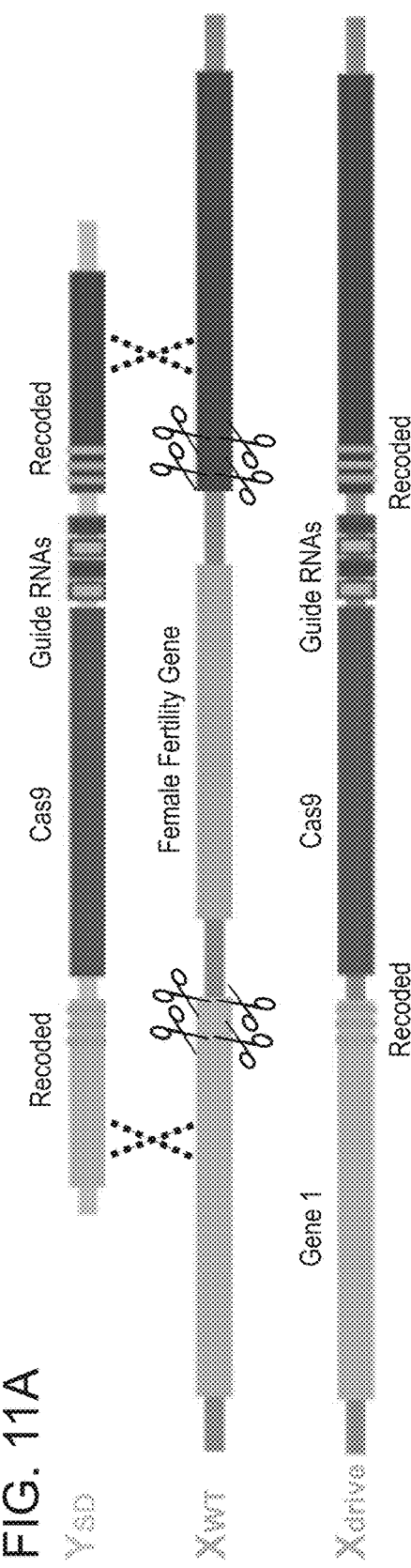
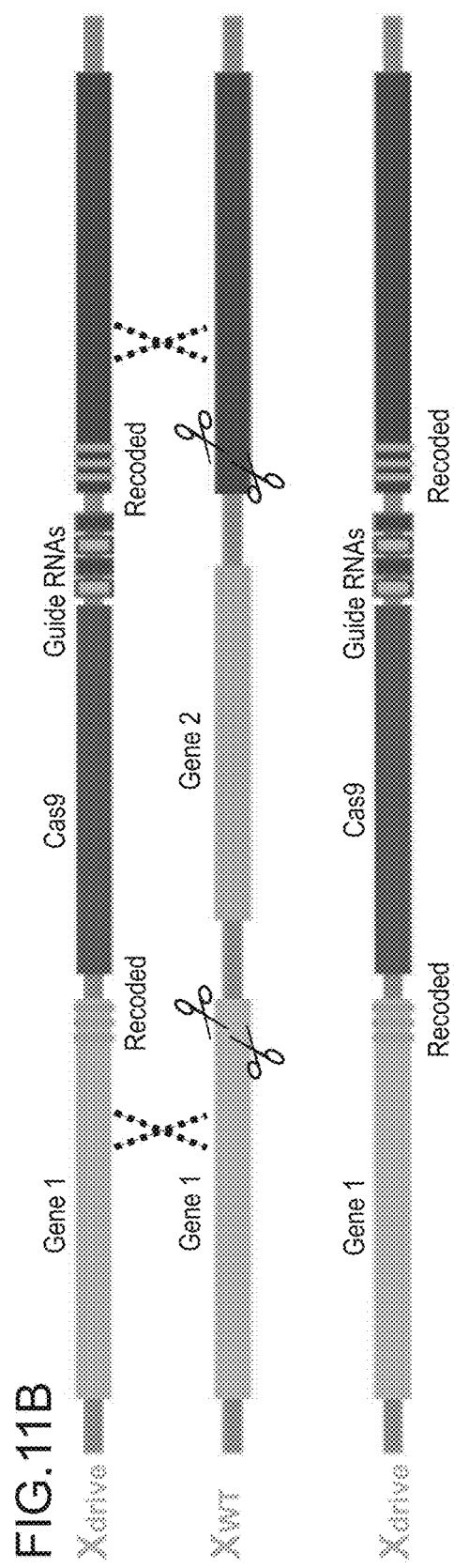
FIG. 11A
FIG. 11B

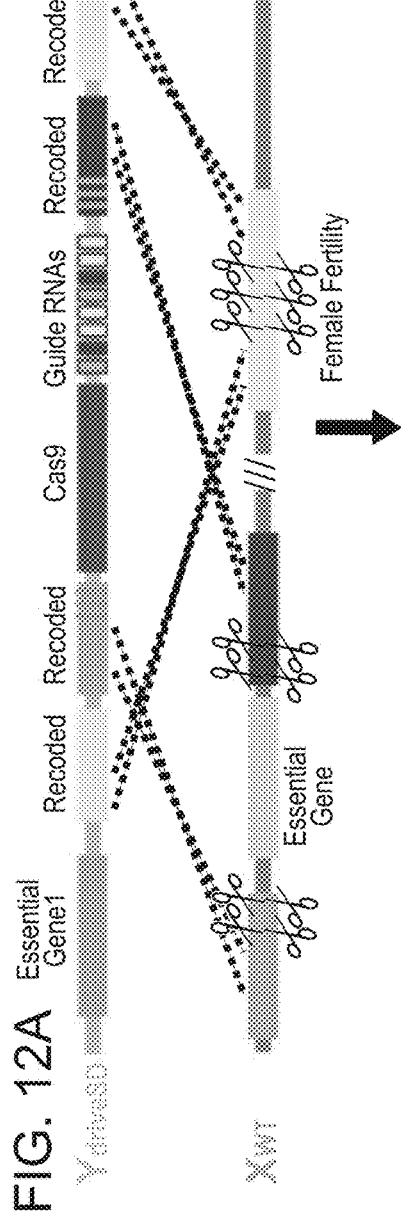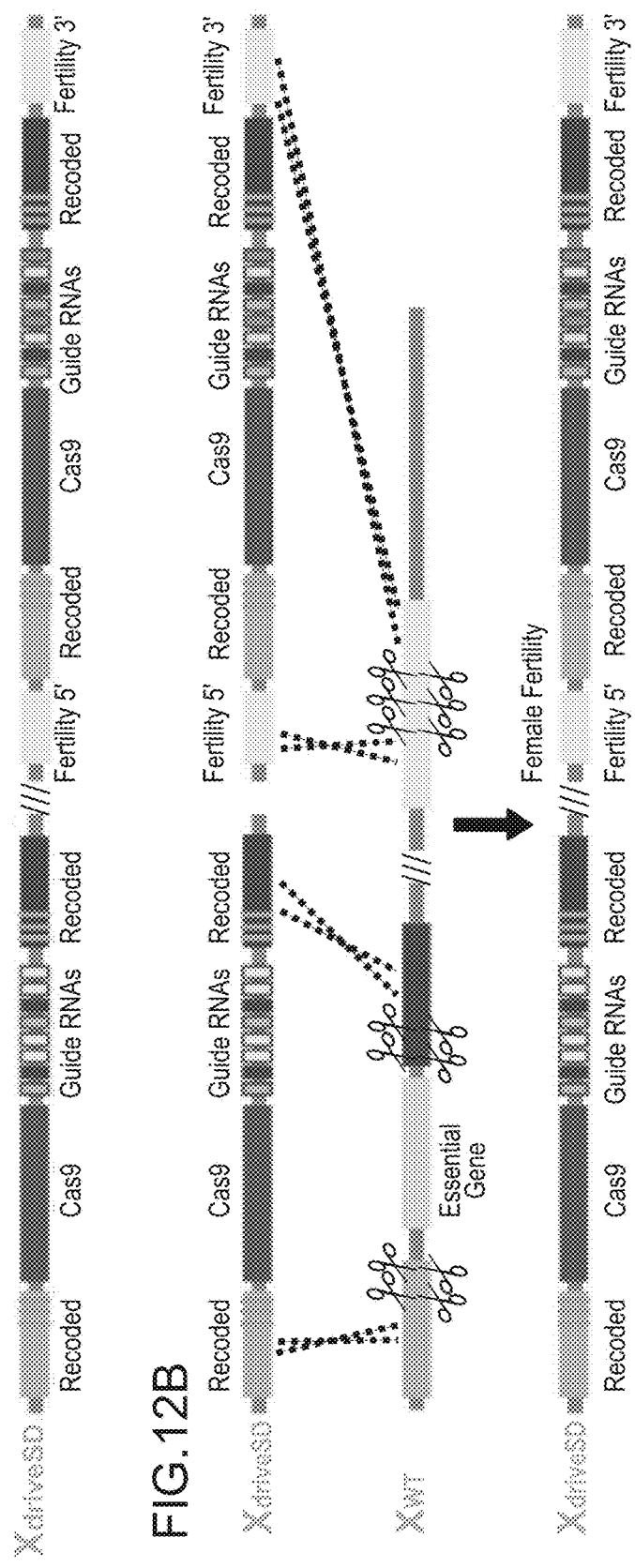
FIG. 12A
FIG. 12B

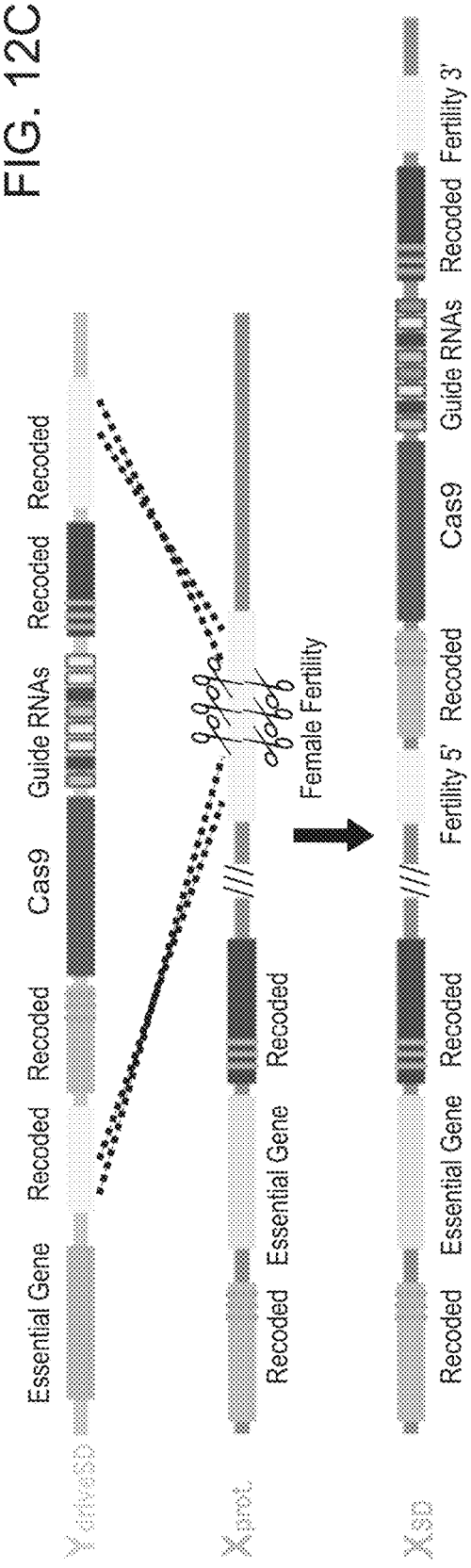
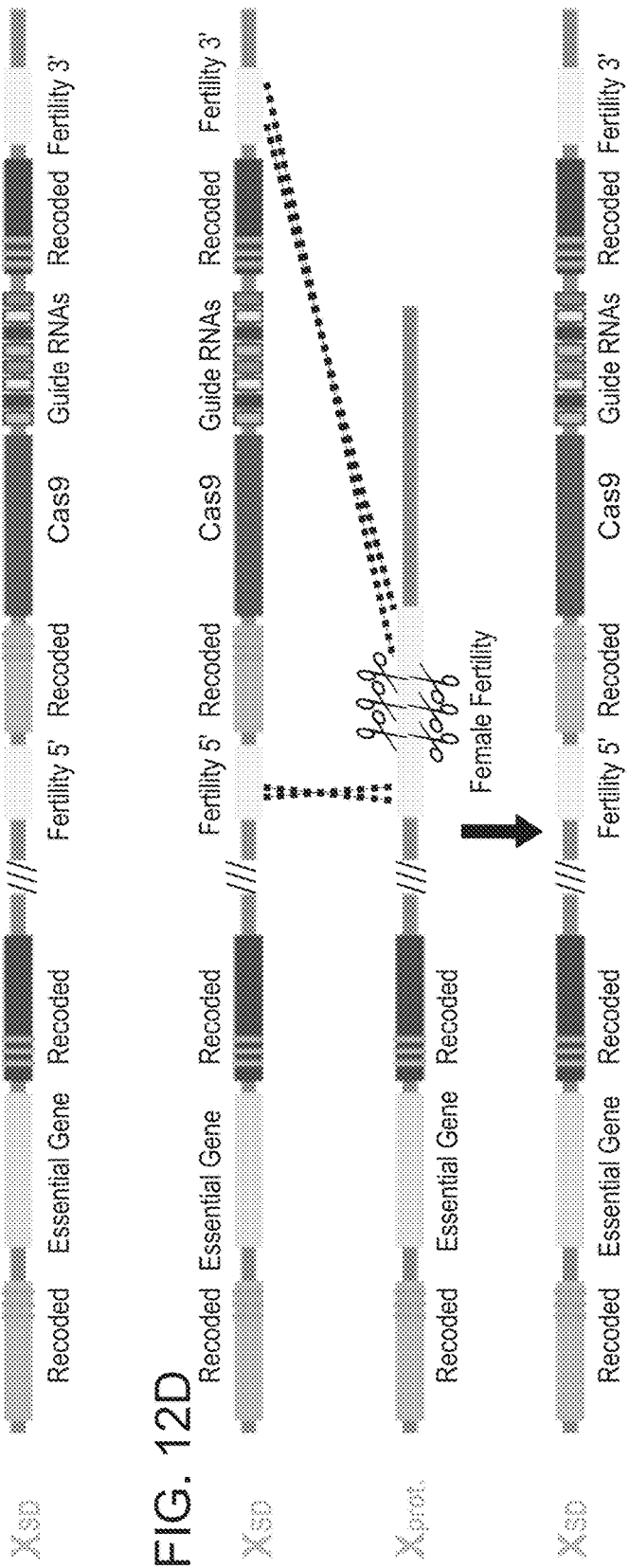

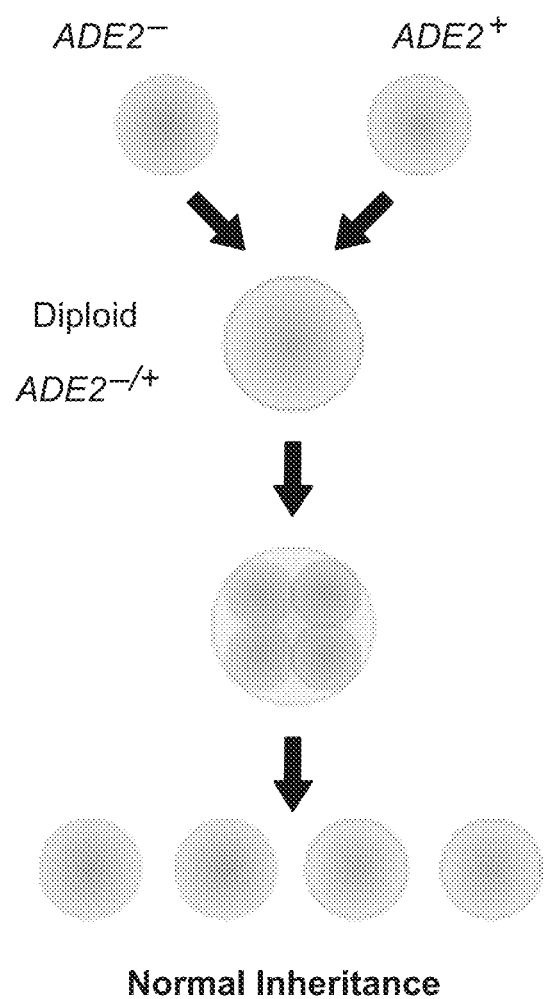

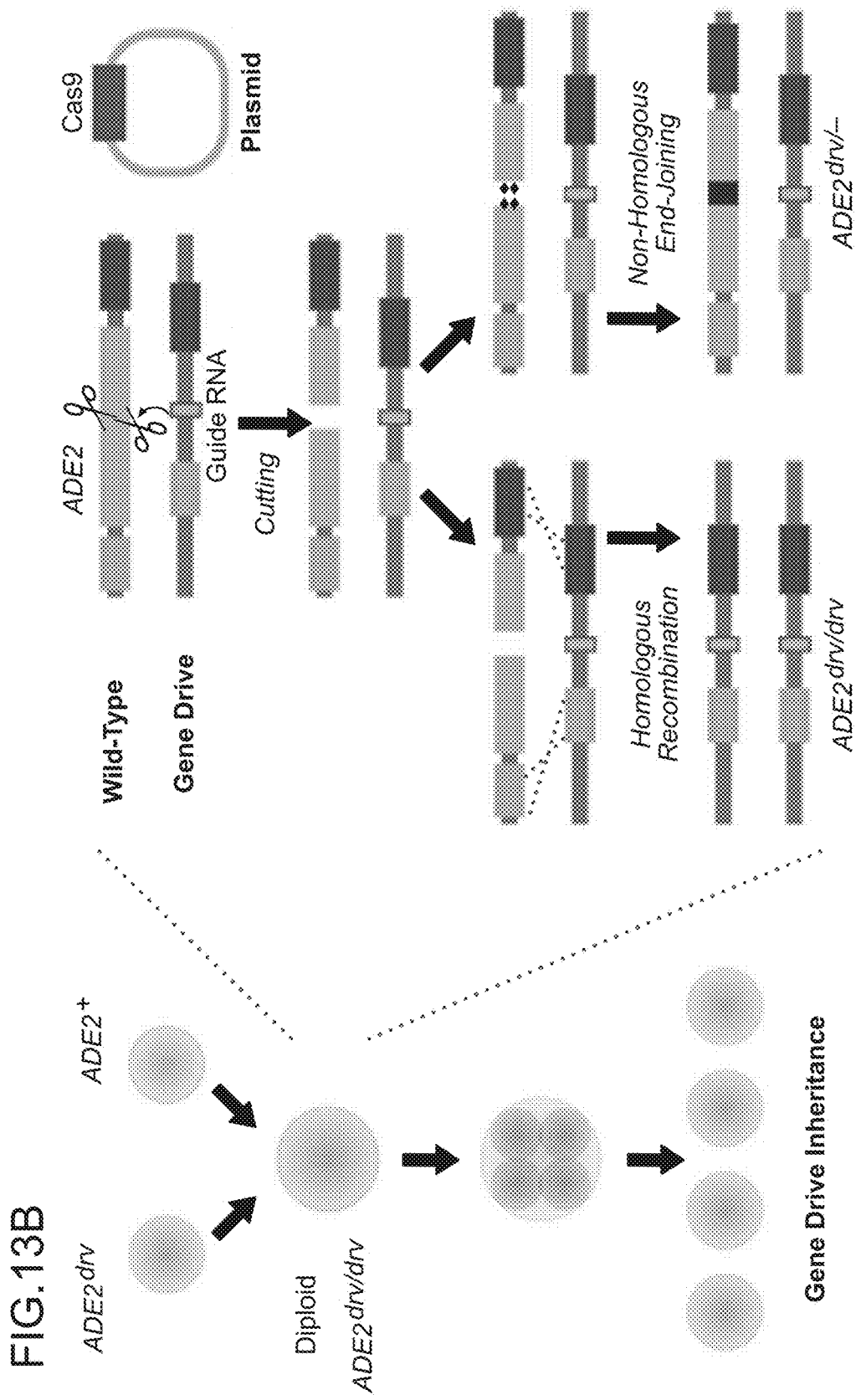

15 Dissected Tetrads | $URA3^-$ WT Parent | $URA3^+$ Drive Parent

SC media (no uracil) | $URA3^-$ WT Parent | $URA3^+$ Drive Parent

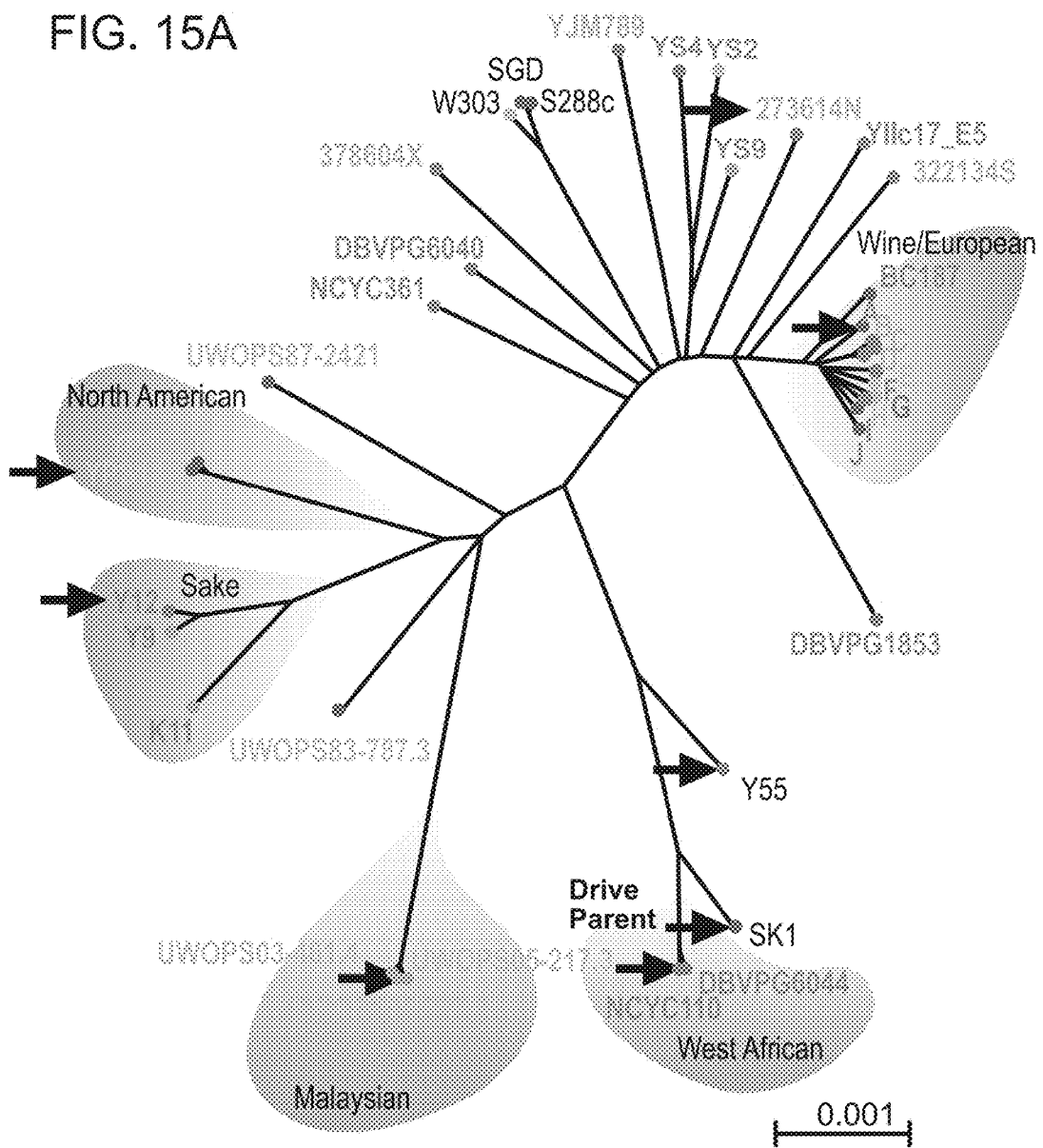

RNA-GUIDED GENE DRIVES

RELATED APPLICATION DATA

This application claims priority to U.S. Provisional Application No. 61/924,735, filed on Jan. 8, 2014 and U.S. Provisional Application No. 62/024,642, filed on Jul. 15, 2014 each of which is hereby incorporated herein by reference in their entirety for all purposes.

BACKGROUND

Gene drives are generally known as genetic elements that skew the natural odds in their favor of being inherited and passed on by progeny. Examples include homing endonuclease genes that copy themselves into chromosomes lacking them, segregation distorters that destroy competing chromosomes during meiosis, transposons that insert copies of themselves elsewhere in the genome, Medea elements that eliminate competing siblings who do not inherit them, and maternally heritable microorganisms such as *Wolbachia* that induce cytoplasmic incompatibility to favor the spread of infected individuals. Because they circumvent the normal rules of natural selection, all of these elements have been considered as potential "gene drive" systems capable of spreading engineered modifications through insect vector populations to block the spread of disease. Homing endonuclease based gene drives have been proposed as a means of genetically controlling malaria mosquito populations. See Windbichler et al., Nature, doi:10.1038/nature09937 (2011). Site-specific selfish genes have been proposed as tools for the control and genetic engineering of natural populations. See Burt, Proc. R. Soc. Lond. B (2003) 270, 921-928 (2003). However, such proposed gene drives are limited in their site specificity or difficult to express in various organisms. A need therefore exists to develop gene drives which can target any desired gene and can be utilized across a broad spectrum of organisms.

SUMMARY

Aspects of the present disclosure are directed to RNA guided gene drives, and in particular, a foreign nucleic acid sequence which is stably introduced into a germline cell of a desired organism. The term foreign nucleic acid sequence as described herein and the term RNA guided gene drive may be used interchangeable herein. A resulting transgenic organism may be developed from the germline cell. The resulting transgenic organism can then be introduced into a wild type population, and through mating by the transgenic organism with a wild type organism, the foreign nucleic acid sequence is transferred to resulting offspring or progeny. As a result, methods of the present disclosure are directed to the production of a population of transgenic organisms having desired traits from an initial transgenic organism and a wild type organism. When the transgenic organism is introduced into a wild type population and mates with a wild type organism, the resulting progeny may be referred to as an altered wild type population. As a result of the foreign nucleic acid sequence being stably entered into the genome of the transgenic offspring or transgenic progeny, transgenic offspring or transgenic progeny may have one or more desired traits resulting from expression of the foreign nucleic acid. According to certain aspects, methods described herein may be used to create an altered wild type population of transgenic organisms where the transgenic organisms exhibit one or more desired traits resulting from the expression of the foreign nucleic acid.

According to certain aspects, the foreign nucleic acid sequence encodes at least an RNA guided DNA binding protein, such as one or more of an RNA guided DNA binding protein nuclease, an RNA guided DNA binding protein nickase or a nuclease null RNA guided DNA binding protein, and one or more or a plurality of guide RNAs (ribonucleic acids). A guide RNA is complementary to DNA (deoxyribonucleic acid), such as a target DNA in the genome of a germline cell. The foreign nucleic acid sequence also encodes at least one or more promoters such that the germline cell may express the RNA guided DNA binding protein and the guide RNAs or any other nucleic acid sequence or gene which may be in the foreign nucleic acid sequence. One of skill will readily be able to identify suitable promoters based on the present disclosure and the particular germline cell. The foreign nucleic acid sequence may also include any other nucleic acid sequence or sequences known to those of skill in the art to be required for expression of the foreign nucleic acid sequence by a germline cell. The foreign nucleic acid sequence may also include any other gene sequence or gene sequences desired to be expressed by the germline cell. Such a gene sequence or such gene sequences may be referred to as "cargo DNA." It is to be understood that one of skill will readily be able to identify one or more gene sequences depending upon the desired trait one of skill wishes to be exhibited by the germline cell or the organism developed from the germline cell when the cell expresses the foreign nucleic acid sequence. The foreign nucleic acid sequence also encodes at least two flanking sequences which flank at least the RNA guided DNA binding protein nuclease and the one or more guide RNAs. As known to those of skill in the art, flanking sequences are placed at opposite ends of a particular nucleic acid sequence such that the particular nucleic acid sequence is between the flanking sequences. According to one aspect, the flanking sequences include at least a sequence which is identical to a corresponding sequence on a selected chromosome. According to one aspect, such flanking sequences allow a cell to insert the foreign nucleic acid sequence into its genomic DNA at a cut site using well-understood mechanisms such as homologous recombination or nonhomologous end joining.

According to certain aspects, when the foreign nucleic acid sequence is expressed by the germline cell, one or more of an RNA guided DNA binding protein and one or more or a plurality of guide RNAs are produced. The RNA guided DNA binding protein and a guide RNA produces a complex of the RNA guided DNA binding protein, the guide RNA and a double stranded DNA target sequence. In this aspect, the RNA is said to guide the DNA binding protein to the double stranded DNA target sequence for binding thereto. This aspect of the present disclosure may be referred to as co-localization of the RNA and DNA binding protein to or with the double stranded DNA.

DNA binding proteins within the scope of the present disclosure may include those which create a double stranded break (which may be referred to as a DNA binding protein nuclease), those which create a single stranded break (referred to as a DNA binding protein nickase) or those which have no nuclease activity (referred to as a nuclease null DNA binding protein) but otherwise bind to target DNA. In this manner, a DNA binding protein-guide RNA complex may be used to create a double stranded break at a target DNA site, to create a single stranded break at a target DNA site or to localize a transcriptional regulator protein or domain, which may be expressed by the cell, at a target DNA site so as to regulate expression of target DNA. According to certain aspects, the foreign nucleic acid sequence may encode one or more of a DNA binding protein nuclease, a DNA binding protein nickase or a nuclease null DNA binding protein. The foreign nucleic acid sequence may also encode one or more transcriptional regulator proteins or domains or one or more donor nucleic acid sequences that are intended to be inserted into the genomic DNA. According to one aspect, the foreign nucleic acid sequence encoding an RNA guided nuclease-null DNA binding protein further encodes the transcriptional regulator protein or domain fused to the RNA guided nuclease-null DNA binding protein. According to one aspect, the foreign nucleic acid sequence encoding one or more RNAs further encodes a target of an RNA-binding domain and the foreign nucleic acid encoding the transcriptional regulator protein or domain further encodes an RNA-binding domain fused to the transcriptional regulator protein or domain.

Accordingly, expression of a foreign nucleic acid sequence by a germline cell may result in a double stranded break, a single stranded break and/or transcriptional activation or repression of the genomic DNA. Donor DNA may be inserted at the break site by cell mechanisms such as homologous recombination or nonhomologous end joining. It is to be understood that expression of a foreign nucleic acid sequence as described herein may result in a plurality of double stranded breaks or single stranded breaks at various locations along target genomic DNA, including one or more or a plurality of gene sequences, as desired.

Aspects of the present disclosure are directed to using the foreign nucleic acid sequence as a gene drive. The concept of a gene drive is known to those of skill in the art and refers to a foreign nucleic acid sequence which when expressed is capable of inserting itself into the genome of the cell into which it has been introduced. The concept of a gene drive is provided in Windbichler et al., *Nature*, doi:10.1038/nature09937 (2011) and Burt, *Proc. R. Soc. Lond*. B (2003) 270, 921-928 (2003) each of which is hereby incorporated by reference in their entireties.

According to one aspect of the present disclosure, the foreign nucleic acid sequences described herein act as gene drives when introduced into a germline cell. In one aspect, the foreign nucleic acid sequence is expressed by the germline cell to produce an RNA guided DNA binding protein and a guide RNA. The guide RNA is complementary to a target DNA sequence on a chromosome. The RNA guided DNA binding protein and the guide RNA co-localize to the target DNA, and the target DNA is cleaved in a site specific manner. The target DNA may be a target DNA site on one or both chromosomes of a chromosome pair. The foreign nucleic acid sequence is then inserted into the genomic DNA at the target DNA cut site, for example, by homologous recombination. The foreign nucleic acid sequence may be inserted into the genomic DNA at one or both chromosomes of a chromosome pair if each chromosome has been cleaved in a site specific manner by the RNA guided DNA binding protein. If inserted into both chromosomes of a chromosome pair, then the germline cell is homozygous for the foreign nucleic acid sequence. In an alternate embodiment, the foreign nucleic acid sequence is inserted into a first chromosome of a chromosome pair. The inserted foreign nucleic acid sequence is then expressed by the cell and the RNA guided DNA binding protein and the guide RNA co-localize at or to a second chromosome of a chromosome pair which is then cleaved in a site specific manner, just as was the first chromosome. The cleaved target DNA in the second chromosome is then repaired, for example by homologous recombination, using the first chromosome as a template. In this manner, the second chromosome is repaired to include the foreign nucleic acid sequence resulting in a germline cell that is homozygous for the foreign nucleic sequence, i.e., the foreign nucleic acid sequence is present in both the first and second chromosome of the chromosome pair. The mechanisms by which cells repair damaged, cleaved or cut genomic DNA are well known. Aspects of the present disclosure take advantage of these cell mechanisms in combination with DNA binding protein nucleases or nickases to create a gene drive with desired foreign genetic material that inserts into the genomic DNA of cells wherein the cell becomes homozygous for the foreign genetic material. The foreign genetic material is then passed on to progeny to create a population of transgenic organisms having one or more desired traits.

Using the concept of a foreign nucleic acid sequence as described herein as a gene drive, methods are provided for incorporating foreign genetic material into a wild population of organisms. Methods are provided for making a cell homozygous for foreign genetic material. Methods are provided for spreading a genetic modification through a wild population of organisms. Methods are provided for spreading a human designed genetic modification through a wild population of organisms. Methods are provided for pan genome engineering by spreading a human designed genetic modification through a wild population of organisms. Methods are provided for editing the genome of a wild species. Methods are provided for editing multiple loci of genomic DNA of an organism. Methods are provided for the multiplexed editing of genomic loci. Methods are provided for reversibly editing a locus or multiple loci of genomic DNA of an organism.

Based upon the desired function of the gene drive described herein, methods are provided for controlling gene flow through a wild population of organisms. Methods are provided for suppressing expansion of a target population of an organism. Methods are provided for decreasing or eliminating a target population of an organism. Methods are providing for increasing a target population of an organism. Methods are provided for reducing or eliminating vector born diseases, such as malaria. Methods are provided for decreasing the spread of disease by a target organism, such as an insect vector population. Methods are provided for disrupting a gene responsible for disease transmission by a target organism. Methods are provided for disrupting a Y chromosome in a germline cell. Methods are provided for disrupting an X chromosome in a germline cell. Methods are provided for controlling invasive pests. Methods are provided for preserving species threatened by ecological change.

According to certain aspects, a method of blocking gene flow from an engineered organism to the wild-type population is provided which includes 1) the insertion of a recoded copy of a gene whose phenotype when disrupted is dominant negative lethal into a distal region of the same chromosome in which the wild-type copy is encoded and 2) the insertion of a selfish genetic element, i.e. RNA guided gene drive as described herein and as the term gene drive is understood by those of skill in the art, that copies itself in place of the wild-type version of the same gene, such that any offspring from an engineered organism and an engineered organism contain two functional copies of the recoded gene, while the offspring of an engineered organism and a wild-type organism will possess only a single copy of the recoded gene after the selfish genetic element replaces the wild-type copy and cannot copy the recoded gene onto the wild-type chromosome.

According to certain aspects, a method of blocking gene flow between a subpopulation bearing a unique sequence and the remaining population is provided which includes 1) releasing a first selfish genetic element that spreads exclusively using the unique sequence and inserts part of a gene whose phenotype when disrupted is dominant negative elsewhere in the genome, 2) releasing a second selfish genetic element that exclusively spreads using the partial gene sequences and inserts a recoded version of the gene and also disrupts the wild-type copy of the gene such that 1) all offspring resulting from matings between an organism bearing the first selfish genetic element and an organism bearing the second selfish genetic element contain the second selfish genetic element in which both wild-type copies of the gene are disrupted but are replaced by recoded copies elsewhere in the genome, and 2) any cross between an organism containing the second selfish genetic element and a wild-type organism generates no progeny because the wild-type copy of the gene is lost and not replaced by a recoded copy.

According to certain aspects, a method of biasing the sex ratio of offspring is provided including using one or more chromosomes that together 1) encode an RNA-guided nuclease that is expressed exclusively during pre-meiosis and 2) express guide RNAs that target the nuclease to cleave sequences uniquely found on one of the sex chromosomes such that viable gametes contain fewer instances of the targeted chromosome than is typical of an unmodified organism.

According to certain aspects, a method of biasing the sex ratio of a population is provided including using a sex chromosome that encodes an RNA-guided nuclease that is expressed exclusively during pre-meiosis and also expresses guide RNAs that target the nuclease to cleave sequences uniquely found on the opposite sex chromosome such that viable gametes predominantly contain the sex chromosome encoding the RNA-guided nuclease.

According to certain aspects, a method of biasing the sex ratio of offspring towards the heterogametic sex (for example XY) is provided including using a chromosome engineered with a copy of an essential gene normally present on the X chromosome and a selfish genetic element that copies itself in place of the wild-type essential gene on the X chromosome such that female progeny are not developmentally viable due to loss of the essential gene while male progeny survive due to the copy on the engineered chromosome.

According to certain aspects, a method of biasing the sex ratio of a population towards the heterogametic sex (for example XY) is provided including using a Y chromosome engineered with a copy of an essential gene normally present on the X chromosome and a selfish genetic element that copies itself in place of the wild-type essential gene on the X chromosome such that female progeny are not developmentally viable due to loss of the essential gene while male progeny survive due to the copy on the engineered Y chromosome.

According to certain aspects, a method of biasing the sex ratio of offspring towards the homogametic sex (for example XX in mammals) including using one or more chromosomes that together 1) encode an RNA-guided nuclease and 2) express guide RNAs that target the nuclease to cleave sequences uniquely found on the heterogametic sex chromosome (for example XY in mammals) such that the heterogametic sex chromosome of any offspring that would normally develop as the heterogametic sex (e.g. males in mammals) is destroyed.

According to certain aspects, a method of biasing the sex ratio of a population towards the homogametic sex (for example XX in mammals) including using a homogametic sex chromosome that 1) encodes an RNA-guided nuclease and 2) expresses guide RNAs that target the nuclease to cleave sequences uniquely found on the heterogametic sex chromosome (for example XY in mammals) such that the heterogametic sex chromosome of any offspring that would normally develop as the heterogametic sex (e.g. males in mammals) is destroyed.

According to certain aspects, a method of biasing the sex ratio of a population towards males includes the release of engineered males that encode a selfish genetic element that copies itself in place of a gene required for female fertility. According to one aspect, the selfish genetic element is encoded on the Y chromosome. According to one aspect, the Y chromosome also encodes a selfish genetic element targeting an essential gene present on the X chromosome.

According to certain aspects, a method of population control is provided including the release into a population to be removed of engineered male organisms containing a Y chromosome that encodes 1) a selfish genetic element that copies itself in place of a gene required for female fertility and 2) a second selfish genetic element that copies itself in place of an essential gene on the X chromosome such that female offspring are nonviable, and the release into a population to be protected of organisms encoding a third selfish genetic element that changes the sequence of the essential gene on the X chromosome such that the offspring of matings between males containing the first and second selfish genetic elements and females containing the third selfish genetic element give rise to fertile male but sterile female offspring.

According to certain aspects, a method is provided of altering a eukaryotic germline cell of an organism including introducing into the germline cell a first foreign nucleic acid sequence encoding an RNA guided DNA binding protein nuclease and one or more guide RNAs, and including corresponding promoter sequences and a first flanking sequence and a second flanking sequence, wherein the one or more guide RNAs are complementary to one or more target locations on genomic DNA of a first chromosome and a second chromosome of a chromosome pair of the germline cell, wherein the nucleic acid sequence encoding the RNA guided DNA binding protein nuclease and the nucleic acid sequence encoding the one or more guide RNAs are between the first flanking sequence and the second flanking sequence, wherein the first flanking sequence includes a first sequence identical to a first portion of the target location on the first chromosome or the second chromosome of the genomic DNA, wherein the second flanking sequence includes a second sequence identical to a second portion of the target location on the first chromosome or the second chromosome of the genomic DNA, wherein at least one copy of the sequence located between the first flanking sequence and the second flanking sequence that is cut and replaced by the foreign nucleic acid sequence is required for the organism to survive or to produce viable offspring, expressing the first foreign nucleic acid sequence to produce the RNA guided DNA binding protein nuclease and the one or more RNAs wherein the RNA guided DNA binding protein nuclease and an associated guide RNA co-localize to an associated target location on the first chromosome of the genomic DNA and the second chromosome of the genomic DNA and the RNA guided DNA binding protein nuclease cleaves the first chromosome of the genomic DNA at the target location in a cleavage site specific manner and cleaves the second chromosome of the genomic DNA at the target location in a cleavage site specific manner, inserting the first foreign nucleic acid sequence into the first chromosome of the chromosome pair of the genomic DNA at the cleavage site, and inserting the first foreign nucleic acid sequence into the second chromosome of the chromosome pair of the genomic DNA at the cleavage site to render the germline cell homozygous for the foreign nucleic acid sequence, and performing the above expression and insertion steps at developmental stage at which the sequence located between the first flanking sequence and the second flanking sequence that is cut and replaced by the foreign nucleic acid sequence to produce a genetic load is no longer required for that organism to survive or produce fertile offspring.

According to certain aspects, a method for targeted population suppression or extinction according to such methods described herein includes releasing an RNA-guided genetic load drive into the targeted population.

A genetic load as that term is used herein may refer to the difference between the fitness of the theoretically optimal genotype in a population and the fitness of the observed average genotype in a population. The term genetic load may also refer to a reduction in the mean fitness for a population compared to the maximum fitness.

Further features and advantages of certain embodiments of the present invention will become more fully apparent in the following description of embodiments and drawings thereof, and from the claims.

BRIEF DESCRIPTION OF THE DRAWINGS

FIG. 1E depicts NHEJ deleting all recognition sites to create a drive resistant allele. FIG. 1F depicts NHEJ creating a drive resistant allele that deleteriously disrupts an essential gene.

FIG. 4A depicts the use of meiotic gene drives to eliminate the competing sex chromosome during meiosis, producing a biased pool of gametes. Drive expression is limited to pre-meiosis to prevent the drive from being lethal. FIG. 4B depicts that meiotic sex chromosome silencing can be circumvented using two orthogonal Cas9 nucleases. Cas9 A causes the cassette encoding Cas9 B to be copied from the sex chromosome to an autosome early in development, where it is free to eliminate the competing sex chromosome during meiosis. FIG. 4C depicts that zygotic X-drives can target the Y chromosome for destruction in the fertilized egg, yielding exclusively female progeny. FIG. 4D depicts that zygotic Y-drives can encode an essential gene normally found on the X chromosome and utilize a gene drive cassette to eliminate that gene from the X. The drive copies itself from the paternal to the maternal X, leaving female zygotes without any copies of the essential gene.

FIG. 5A depicts population suppression using dual-function Y-drives where the A Y-drive that also contains a sterile-daughter capability (Y-Drive-SD) acts as a zygotic drive in the wild-type population, which can lead to extinction. FIG. 5B depicts that upon encountering a standard drive that recodes the essential gene, the Y-Drive-SD will no longer drive. The sterile-daughter effect will prevent mutual drive invasion until the invasive population collapses.

FIGS. 9A-9C depict a method described herein wherein Drive 1 recodes a male essential gene on the Y chromosome (if present) and a recessive essential gene on the X chromosome while inserting itself (i.e., being inserted by a cell mechanism such as homologous recombination after expression of Cas9 and guide RNA and localization of the Cas9 and guide RNA to a target nucleic acid sequence) adjacent to the unique gene. Drive 2 spreads through the modified X chromosome, eliminates Drive 1 from the autosome, and also jumps into the modified Y chromosome if present. Upon mating with a wild-type organism, Drive 2 eliminates the essential genes from the X or Y chromosomes. The only viable progeny are hybrid females that retain a single recoded copy of the recessive essential gene on the X chromosome. These can mate freely with males that have been modified with Drive 2, permitting wild-type genes to spread into the engineered population. Mating with a wild-type male yields only more hybrid females, preventing gene flow back into the wild-type population.

FIGS. 10A-10D depict a method for making a zygotic Y-drive as described herein.

FIG. 11A depicts one method of making a sterile-daughter Y chromosome that eliminates a gene required for female fertility. Y chromosome (Y-SD) is not a true drive, but incorporates a limited gene drive mechanism that replaces a gene essential for female fertility with the drive. FIG. 11B depicts that in the daughters of Y-SD males, the drive similar replaces the maternal copy of the female fertility gene, causing sterility. If no gene specific for female fertility is known, a fertility gene required for both sexes can be target and complemented with an extra copy elsewhere on the Y chromosome.

FIG. 12A depicts a method of making a Y-drive that includes sterile-daughter capability (Y-drive-SD) (Y-drive+ sterile-daughter Y chromosomes. Upon mating with a wild-type female, Y-drive-SD replaces or disrupts both an essential gene and a female fertility gene. Males survive due to complementation from the extra copy on Y-drive-SD. As depicted in FIG. 12B, in female progeny, the drives similarly replace the maternal copies, leaving daughters embryonically nonviable. Y-drive-SD consequently exhibits drive. As depicted in FIG. 12C, females modified with a protective drive have the sites flanking the essential gene recoded. Y-Drive-SD can only replace the fertility gene. As depicted in FIG. 12D, female progeny are still viable, but lack any copies of the fertility gene and are consequently infertile. Because males do not gain any fitness benefit from the absence of sisters, Y-drive-SD will not drive in a protected population. However, its only fitness cost is that incurred by the drive itself, so it will be removed from the population only slowly. The loss of female reproductive output will result in potent population suppression. Because of this, protected individuals will find it difficult to invade populations where Y-drive-SD is common. Similarly, Y-Drive-SD will not be able to invade protected populations.

FIG. 13A is a schematic showing that biased inheritance of ADE2 is readily visible in *S. cerevisiae*. Mutations in ADE2 generate a red phenotype on adenine-limiting media due to the buildup of red pigments. Mating a red mutant haploid to a wild-type haploid produce cream-colored diploids, which yield 50% red and 50% cream-colored progeny upon sporulation. Biased inheritance of ADE2 is readily visible in *S. cerevisiae*. FIG. 13B is a schematic showing that when haploids with a gene drive targeting ADE2 mate with wild-type haploids in the presence of Cas9, cutting and subsequent replacement or disruption of ADE2 will lead to red diploids that yield exclusively red progeny.

FIG. 15A is a schematic of a phylogenomic tree indicating the relationships between wild-type strains selected for gene drive testing. Adapted with permission from Macmillan Publishers Ltd: *Nature* 458:337-341, copyright 2009.

DETAILED DESCRIPTION

Figure 1A:
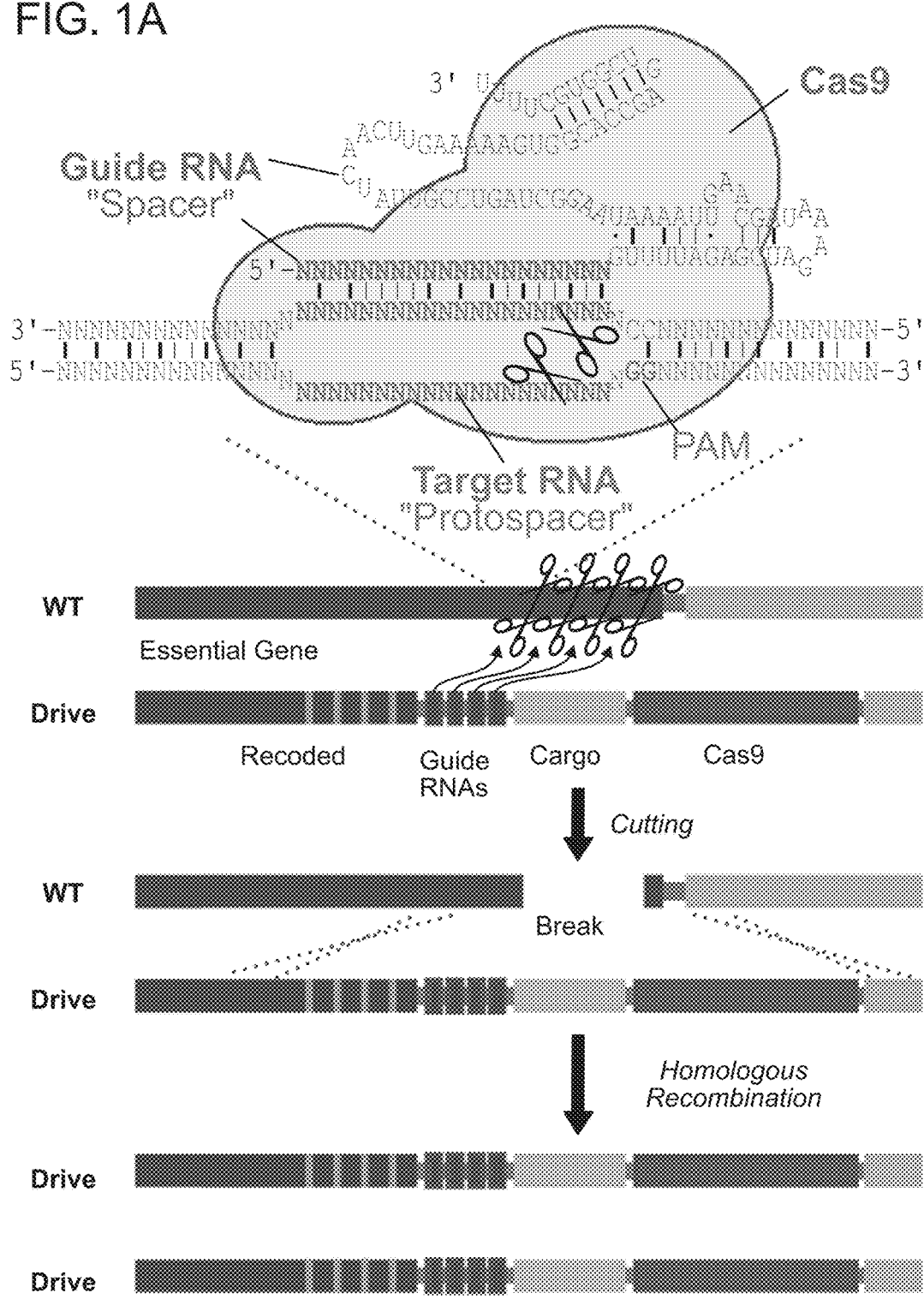
FIG. 1A is a schematic of a standard RNA-guided Cas9 gene drive showing expression of Cas9 and guide RNA, co-localization, cutting of a target gene to create a break and insertion of the RNA guided Cas9 gene drive into the target gene at the cut site by homologous recombination.

Embodiments of the present disclosure are based on the use of RNA guided DNA binding proteins to co-localize with guide RNA at a target DNA site and act as gene drives. Such DNA binding proteins are readily known to those of skill in the art to bind to DNA for various purposes. Such DNA binding proteins may be naturally occurring. DNA binding proteins included within the scope of the present disclosure include those which may be guided by RNA, referred to herein as guide RNA. According to one aspect, the guide RNA is between about 10 to about 500 nucleotides. According to one aspect, the RNA is between about 20 to about 100 nucleotides. According to this aspect, the guide RNA and the RNA guided DNA binding protein form a co-localization complex at the DNA.

DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

Bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus. Journal of Bacteriology* 190, 1390 (February, 2008).

Three classes of CRISPR systems are generally known and are referred to as Type I, Type II or Type III). According to one aspect, a particular useful enzyme according to the present disclosure to cleave dsDNA is the single effector enzyme, Cas9, common to Type II. See K. S. Makarova et al., Evolution and classification of the CRISPR-Cas systems. *Nature reviews. Microbiology* 9, 467 (June, 2011) hereby incorporated by reference in its entirety. Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9.

According to one aspect, the enzyme of the present disclosure, such as Cas9 unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, different protospacer-adjacent motif can be utilized. For example, the *S. pyogenes* system requires an NGG sequence, where N can be any nucleotide. *S. thermophilus* Type II systems require NGGNG (see P. Horvath, R. Barrangou, CRISPR/Cas, the immune system of bacteria and archaea. *Science* 327, 167 (Jan. 8, 2010) hereby incorporated by reference in its entirety and NNAGAAW (see H. Deveau et al., Phage response to CRISPR-encoded resistance in *Streptococcus thermophilus. Journal of bacteriology* 190, 1390 (February, 2008) hereby incorporatd by reference in its entirety), respectively, while different *S. mutans* systems tolerate NGG or NAAR (see J. R. van der Ploeg, Analysis of CRISPR in *Streptococcus mutans* suggests frequent occurrence of acquired immunity against infection by M102-like bacteriophages. *Microbiology* 155, 1966 (June, 2009) hereby incorporated by refernece in its entirety. Bioinformatic analyses have generated extensive databases of CRISPR loci in a variety of bacteria that may serve to identify additional useful PAMs and expand the set of CRISPR-targetable sequences (see M. Rho, Y. W. Wu, H. Tang, T. G. Doak, Y. Ye, Diverse CRISPRs evolving in human microbiomes. *PLoS genetics* 8, e1002441 (2012) and D. T. Pride et al., Analysis of streptococcal CRISPRs from human saliva reveals substantial sequence diversity within and between subjects over time. *Genome research* 21, 126 (January, 2011) each of which are hereby incorporated by reference in their entireties.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Enke et al., *Science* 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: Methanococcus maripaludis C7; *Corynebacterium diphtheriae; Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua; Lactobacillus casei; Lactobacillus rhamnosus* GG; *Lactobacillus salivarius* UCC 118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans; Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ 1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum; Mycoplasma* mobile 163K; *Mycoplasma penetrans; Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus*

Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylei 269 97; *Campylobacter jejuni* 81116; *Campylobacter jejuni*; *Campylobacter* lari RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis* holarctica; *Francisella tularensis* FSC 198; *Francisella tularensis tularensis*; *Francisella tularensis* WY96-3418; and *Treponema denticola* ATCC 35405. The Cas9 protein may be referred by one of skill in the art in the literature as Csn1. An exemplary *S. pyogenes* Cas9 protein sequence is shown below. See Deltcheva et al., *Nature* 471, 602-607 (2011) hereby incorporated by reference in its entirety.

MDKKYSIGLDIGTNSVGWAVITDEYKVPSKKFKVLGNTDRHSIKKNLIGA

LLFDSGETA

E

ATRLKRTARRRYTRRKNRICYLQEIFSNEMAKVDDSFEHRLEESELVEED

KKHERHPIFGNIVDEVAYHEKYPTIYHLRKKLVDSTDKADLRLIYLALAH

MIKERGHFLIEGDLNPDNSDVDKLFIQLVQTYNQLFEENPINASGVDAKA

ILSARLSKSRRLENLIAQLPGEKKNGLFGNLIALSLGLTPNFKSNFDLAE

DAKLQLSKDTYDDDLDNLLAQIGDQYADLFLAAKNLSDA

I

LLSDILRVNTEITKAPLSASMIKRYDEHHQDLTLLKALVRQQLPEKYKEI

FEDQSKNGYAGYIDGGASQEEFYKFIKPILEKMDGTEELLVKLNREDLLR

KQRTFDNGSIPHQIHLGELHAILRRQEDEYPELKDNREKIEKILTERIPY

YVGPLARGNSREAWMTRKSEETITPWNFEEVVDKGASAQSFIERMTNEDK

NLPNEKVLPKHSLLYEYFTVYNELTKVKYVTEGMRKPA

FL

SGEQKKAIVDLLFKTNRKVTVKQLKEDYFKKIECFDSVEISGVEDRFNAS

LGTYHDLLKIIKDKDFLDNEENEDILEDIVLTLTLFEDREMIEERLKTYA

HLFDDKVMKQLKRRRYTGW

G

RLSRKLINGIRDKQSGKTILDFLKSDGEANRNFMQLIHDDSLTFKEDIQK

AQVSGQGDSLHEHIANLAGSPAIKKGILQTVKVVDELVKVMGRHKPENIV

IEMARENQTTQKGQKNSRE

R

MKRIEEGIKELGSQILKEHPVENTQLQNEKLYLYYLQNGRDMYVDQELDI

NRLSDYDVD

H

IVPQSFLKDDSIDNKVLTRSDKNRGKSDNVPSEEVVKKMKNYWRQLLNAK

LITQRKFD

NL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDV

RK

MIAKSEQEIGKATAKYFFYSNIMNFFKTEITLANGEIRKRPLIETNGETG

EIVWDKGRDFATVRKVLSMPQVNIVKKTEVQTGGFSKESILPKRNSDKLI

ARKKDWDPKKYGGFDSPTV

A

YSVLVVAKVEKGKSKKLKSVKELLGITIMERSSFEKNPIDFLEAKGYKEV

KKDLIIKLPKYSLFELENGRKRMLASAGELQKGNELALPSKYVNFLYLAS

HYEKLKGSPEDNEQKQLF

VE

QHKHYLDEIIEQISEFSKRVILADANLDKVLSAYNKHRDKPIREQAENII

HLFTLTNLGAPAAFKYFDTTIDRKRYTSTKEVLDATLIHQSITGLYETRI

DLSQLGGD

According to one aspect, the specificity of gRNA-directed Cas9 cleavage is used as a mechanism for genome engineering and as a drive gene. According to one aspect, hybridization of the gRNA need not be 100 percent in order for the enzyme to recognize the gRNA/DNA hybrid and affect cleavage. Some off-target activity could occur. For example, the *S. pyogenes* system tolerates mismatches in the first 6 bases out of the 20 bp mature spacer sequence in vitro. According to one aspect, greater stringency may be beneficial in vivo when potential off-target sites matching (last 14 bp) NGG exist within the human reference genome for the gRNAs.

According to certain aspects, specificity may be improved. When interference is sensitive to the melting temperature of the gRNA-DNA hybrid, AT-rich target sequences may have fewer off-target sites. Carefully choosing target sites to avoid pseudo-sites with at least 14 bp matching sequences elsewhere in the genome may improve specificity. The use of a Cas9 variant requiring a longer PAM sequence may reduce the frequency of off-target sites. Directed evolution may improve Cas9 specificity to a level sufficient to completely preclude off-target activity, ideally requiring a perfect 20 bp gRNA match with a minimal PAM. Accordingly, modification to the Cas9 protein is a representative embodiment of the present disclosure. CRISPR systems useful in the present disclosure are described in R. Barrangou, P. Horvath, CRISPR: new horizons in phage resistance and strain identification. *Annual review of food science and technology* 3, 143 (2012) and B. Wiedenheft, S. H. Sternberg, J. A. Doudna, RNA-guided genetic silencing systems in bacteria and archaea. *Nature* 482, 331 (Feb. 16, 2012) each of which are hereby incorporated by reference in their entireties.

According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase.

An exemplary DNA binding protein is an RNA guided DNA binding protein nuclease of a Type II CRISPR System, such as a Cas9 protein or modified Cas9 or homolog of Cs9. An exemplary DNA binding protein is a Cas9 protein nickase. An exemplary DNA binding protein is an RNA guided DNA binding protein of a Type II CRISPR System which lacks nuclease activity. An exemplary DNA binding protein is a nuclease-null Cas9 protein.

According to certain aspects of methods of RNA-guided genome regulation described herein, Cas9 is altered to reduce, substantially reduce or eliminate nuclease activity. According to one aspect, Cas9 nuclease activity is reduced, substantially reduced or eliminated by altering the RuvC nuclease domain or the HNH nuclease domain. According to one aspect, the RuvC nuclease domain is inactivated. According to one aspect, the HNH nuclease domain is inactivated. According to one aspect, the RuvC nuclease domain and the HNH nuclease domain are inactivated. According to an additional aspect, Cas9 proteins are provided where the RuvC nuclease domain and the HNH nuclease domain are inactivated. According to an additional aspect, nuclease-null Cas9 proteins are provided insofar as the RuvC nuclease domain and the HNH nuclease domain are inactivated. According to an additional aspect, a Cas9 nickase is provided where either the RuvC nuclease domain or the HNH nuclease domain is inactivated, thereby leaving the remaining nuclease domain active for nuclease activity. In this manner, only one strand of the double stranded DNA is cut or nicked.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinke et al., *Science* 337, 816-821 (2012). According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 or Cas9N and exhibits reduced or eliminated nuclease activity, or nuclease activity is absent or substantially absent within levels of detection. According to this aspect, nuclease activity for a Cas9N may be undetectable using known assays, i.e. below the level of detection of known assays.

According to one aspect, the Cas9 protein, Cas9 protein nickase or nuclease null Cas9 includes homologs and orthologs thereof which retain the ability of the protein to bind to the DNA and be guided by the RNA. According to one aspect, the Cas9 protein includes the sequence as set forth for naturally occurring Cas9 from *S. pyogenes* and protein sequences having at least 30%, 40%, 50%, 60%, 70%, 80%, 90%, 95%, 98% or 99% homology thereto and being a DNA binding protein, such as an RNA guided DNA binding protein.

According to one aspect, an engineered Cas9-gRNA system is provided which enables RNA-guided genome regulation in cells by tethering transcriptional activation domains to either a nuclease-null Cas9 or to guide RNAs. According to one aspect of the present disclosure, one or more transcriptional regulatory proteins or domains (such terms are used interchangeably) are joined or otherwise connected to a nuclease-deficient Cas9 or one or more guide RNA (gRNA). The transcriptional regulatory domains correspond to targeted loci. Accordingly, aspects of the present disclosure include methods and materials for localizing transcriptional regulatory domains to targeted loci by fusing, connecting or joining such domains to either Cas9N or to the gRNA. According to certain aspects, methods are provided for regulating endogenous genes using Cas9N, one or more gRNAs and a transcriptional regulatory protein or domain. According to one aspect, an endogenous gene can be any desired gene, referred to herein as a target gene.

According to one aspect, a Cas9N-fusion protein capable of transcriptional activation is provided. According to one aspect, a VP64 activation domain (see Zhang et al., *Nature Biotechnology* 29, 149-153 (2011) hereby incorporated by reference in its entirety) is joined, fused, connected or otherwise tethered to the C terminus of Cas9N. According to one method, the transcriptional regulatory domain is provided to the site of target genomic DNA by the Cas9N protein. According to one method, a Cas9N fused to a transcriptional regulatory domain is provided within a cell along with one or more guide RNAs. The Cas9N with the transcriptional regulatory domain fused thereto bind at or near target genomic DNA. The one or more guide RNAs bind at or near target genomic DNA. The transcriptional regulatory domain regulates expression of the target gene. According to a specific aspect, a Cas9N-VP64 fusion activated transcription of reporter constructs when combined with gRNAs targeting sequences near the promoter, thereby displaying RNA-guided transcriptional activation.

According to one aspect, a gRNA-fusion protein capable of transcriptional activation is provided. According to one aspect, a VP64 activation domain is joined, fused, connected or otherwise tethered to the gRNA. According to one method, the transcriptional regulatory domain is provided to the site of target genomic DNA by the gRNA. According to one method, a gRNA fused to a transcriptional regulatory domain is provided within a cell along with a Cas9N protein. The Cas9N binds at or near target genomic DNA. The one or more guide RNAs with the transcriptional regulatory protein or domain fused thereto bind at or near target genomic DNA. The transcriptional regulatory domain regulates expression of the target gene. According to a specific aspect, a Cas9N protein and a gRNA fused with a transcriptional regulatory domain activated transcription of reporter constructs, thereby displaying RNA-guided transcriptional activation.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain is a transcriptional repressor. According to one aspect, the transcriptional regulator protein or domain downregulates expression of the target nucleic acid. Transcriptional activators and transcriptional repressors can be readily identified by one of skill in the art based on the present disclosure.

According to one aspect, the foreign nucleic acid sequence encodes two or more guide RNAs with each RNA being complementary to an adjacent site in the DNA target nucleic acid and also encodes at least one RNA guided DNA binding protein nickase and being guided by the two or more RNAs, wherein the two or more RNAs and the at least one RNA guided DNA binding protein nickase are expressed and wherein the at least one RNA guided DNA binding protein nickase co-localizes with the two or more RNAs to the DNA target nucleic acid and nicks the DNA target nucleic acid resulting in two or more adjacent nicks. According to certain aspects, the two or more adjacent nicks are on the same strand of the double stranded DNA. According to one aspect, the two or more adjacent nicks are on the same strand of the double stranded DNA and result in homologous recombination. According to one aspect, the two or more adjacent nicks are on different strands of the double stranded DNA. According to one aspect, the two or more adjacent nicks are on different strands of the double stranded DNA and create double stranded breaks. According to one aspect, the two or more adjacent nicks are on different strands of the double stranded DNA and create double stranded breaks resulting in nonhomologous end joining. According to one aspect, the two or more adjacent nicks are on different strands of the double stranded DNA and are offset with respect to one another. According to one aspect, the two or more adjacent nicks are on different strands of the double stranded DNA and are offset with respect to one another and create double stranded breaks. According to one aspect, the two or more adjacent nicks are on different strands of the double stranded DNA and are offset with respect to one another and create double stranded breaks resulting in nonhomologous end joining. According to one aspect, the two or more adjacent nicks are on different strands of the double stranded DNA and create double stranded breaks resulting in fragmentation of the target nucleic acid thereby preventing expression of the target nucleic acid.

According to certain aspects, binding specificity of the RNA guided DNA binding protein may be increased according to methods described herein. According to one aspect, off-set nicks are used in methods of genome-editing. A large majority of nicks seldom result in NHEJ events, (see Certo et al., Nature Methods 8, 671-676 (2011) hereby incorporated by reference in its entirety) thus minimizing the effects of off-target nicking. In contrast, inducing off-set nicks to generate double stranded breaks (DSBs) is highly effective at inducing gene disruption. According to certain aspects, 5' overhangs generate more significant NHEJ events as opposed to 3' overhangs. Similarly, 3' overhangs favor HR over NHEJ events, although the total number of HR events is significantly lower than when a 5' overhang is generated. Accordingly, methods are provided for using nicks for homologous recombination and off-set nicks for generating double stranded breaks to minimize the effects of off-target Cas9-gRNA activity.

Germline cells according to the present disclosure include any germline cell into which foreign nucleic acids can be introduced and expressed as described herein. It is to be understood that the basic concepts of the present disclosure described herein are not limited by cell type. Germline cells according to the present disclosure include eukaryotic germline cells, prokaryotic germline cells, animal germline cells, mammalian germline cells, plant germline cells, insect germline cells, fungal germline cells, archael germline cells, eubacterial germline cells and the like. Further, germline cells include any in which it would be beneficial or desirable to introduce a foreign nucleic acid sequence described herein.

Target nucleic acids include any nucleic acid sequence to which a co-localization complex as described herein can be useful to either cut, nick or regulate. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and Cas9 proteins which co-localize to a DNA including a target nucleic acid. One of skill will further be able to identify transcriptional regulator proteins or domains which likewise co-localize to a DNA including a target nucleic acid. DNA includes genomic DNA, mitochondrial DNA, viral DNA or exogenous DNA.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

Transcriptional regulator proteins or domains which are transcriptional activators or transcriptional repressors may be readily identifiable by those skilled in the art based on the present disclosure and the particular germline cell.

The following examples are set forth as being representative of the present disclosure. These examples are not to be construed as limiting the scope of the present disclosure as these and other equivalent embodiments will be apparent in view of the present disclosure, figures and accompanying claims.

Example I

Cas9 Gene Drives

Figure 1B:
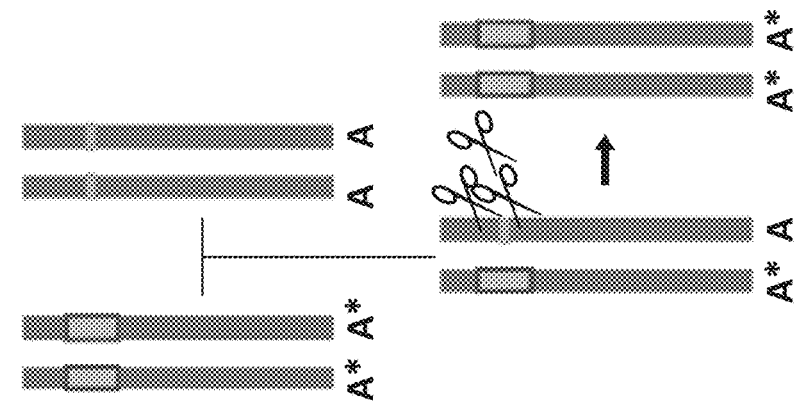
FIG. 1B depicts a chromosomal view of gene drive inheritance.

FIG. 1A is a schematic showing the colocalization of a guide RNA and a Cas9 nuclease to a target DNA. The target DNA sites include a "protospacer" sequence that matches the "spacer" of the guide RNA and a short protospacer-adjacent motif (PAM) required for Cas9 binding. An exemplary Cas9 gene drive shown in FIG. 1A is a foreign nucleic acid sequence as described herein (which may be referred to as a "cassette" as that term is understood by those of skill in the art) that encodes at least an RNA guided Cas9 nuclease, one or more guide RNAs that are complementary to one or more target DNA sites, such as within an adjacent essential gene, and flanking sequences. The cassette may also include any cargo genetic material, such as one or more genes to be expressed by the germline cell into which the cargo genetic material is to be inserted or to be expressed by the descendants of that cell. The Cas9 gene drive is expressed to produce Cas9 and the one or more guide RNAs which then co-localize at one or more target DNA sites on a first chromosome of a chromosome pair and where the Cas9 then cleaves the target DNA on the first chromosome in a site specific manner producing a double stranded break. Homology-directed repair of Cas9-induced double-strand breaks then inserts the Cas9 gene drive into the first chromosome at the cut site. According to certain aspects, the inserted Cas9 gene drive is then expressed to produce Cas9 and the one or more guide RNAs which then co-localize at the one or more target DNA sites on the second chromosome of the chromosome pair and then cleaves the target DNA in a site specific manner producing a double stranded break. Homology directed repair of the Cas9-induced double stranded breaks uses the intact Cas9 drive-containing chromosome as a template thereby inserting the Cas9 drive into the second chromosome of the chromosome pair to create a chromosome pair that is homozygous for the Cas9 gene drive. This is depicted in FIG. 1B.

Figure 1C:
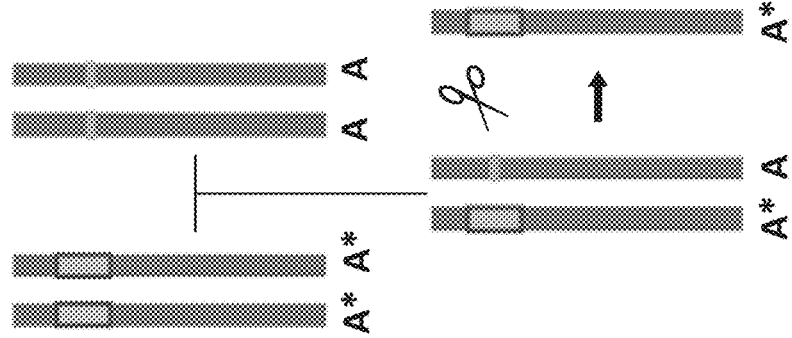
FIG. 1C depicts a mutation preventing the co-localization of Cas9 and a guide RNA so as to prevent cutting of the target DNA and insertion of the gene drive.
Figure 1D:
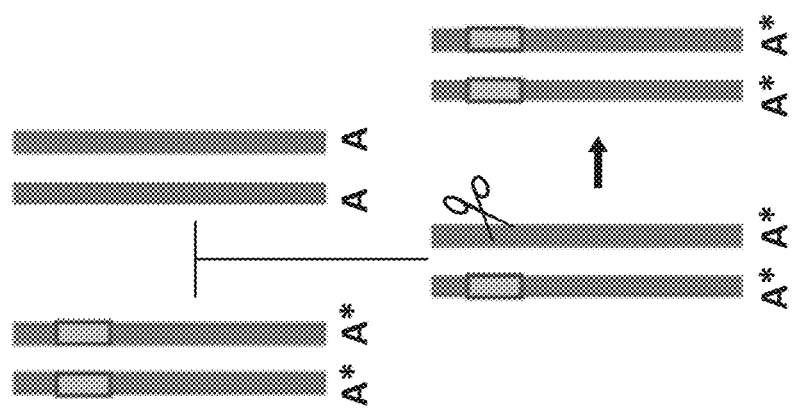
FIG. 1D depicts the use of a plurality of guide RNAs and cut sites to avoid a mutation from preventing insertion of the gene drive.

FIG. 1C depicts that a mutation at the target DNA site may prevent cutting by a single Cas9 protein. Accordingly, aspects of the present disclosure depicted in FIG. 1D provide multiple guide RNAs for multiple target DNA sites. In this manner, RNA-guided gene drives can overcome resistant alleles by targeting multiple adjacent sequences such that no single mutation can confer resistance. The chances that a target site will not be cleaved due to a mutation are greatly reduced as the target DNA site will likely be cleaved in multiple locations thereby providing a cut site into which the RNA guided gene drive can be inserted. As shown in FIG. 1E, repair using the alternative non-homologous end-joining (NHEJ) pathway can delete all recognition sites, creating a drive-resistant allele that outcompetes the drive. FIG. 1F depicts that NHEJ events that disrupt an essential gene are highly deleterious and will be selected against in favor of the drive. Choosing target sites within an essential gene ensures that incorrect repair events cannot create resistant alleles by deleting all of the targeted sequences. Non-homologous end joining can create small insertions or deletions at the junction of the repair which can prevent binding of a guide RNA and Cas9 to the repair site. As a result, the RNA guided gene drive may not be able to be inserted into this site on the chromosome if there is only a single guide RNA for this site encoded in the RNA guided gene drive. However, having the RNA guided gene drive encode for multiple guide RNAs targeting multiple sites and therefore making multiple cut sites will increase the odds that the RNA guided gene drive will be inserted into the chromosome. Further, aspects of the present disclosure are directed to targeting multiple sites for Cas9 within an essential gene as a method for improving efficiency of inserting the RNA guided gene drive into a chromosome.

Example II

Editing and Regulating Multiple Endogenous Loci

Figure 2A:
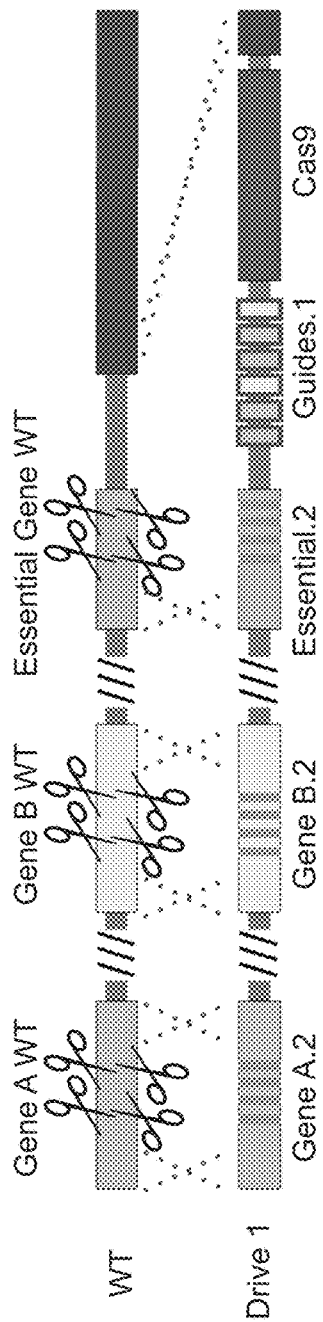
FIG. 2A depicts the use of a single drive to edit multiple distal sites by including appropriate guide RNAs.
Figure 2B:
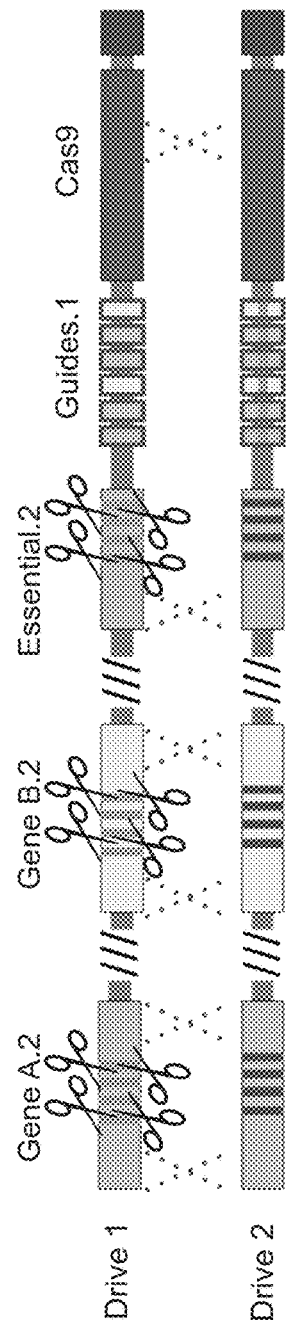
FIG. 2B depicts the use of subsequent drives to update changes made by a first drive.
Figure 2C:
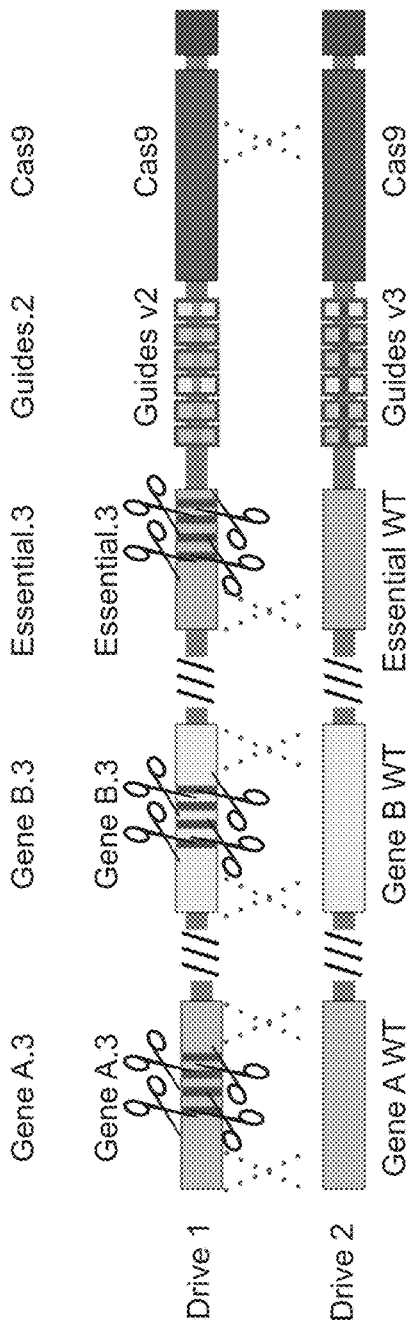
FIG. 2C depicts the use of a restorative drive to all changes back to the wild-type, leaving only the Cas9 gene and guide RNAs.
Figure 7:
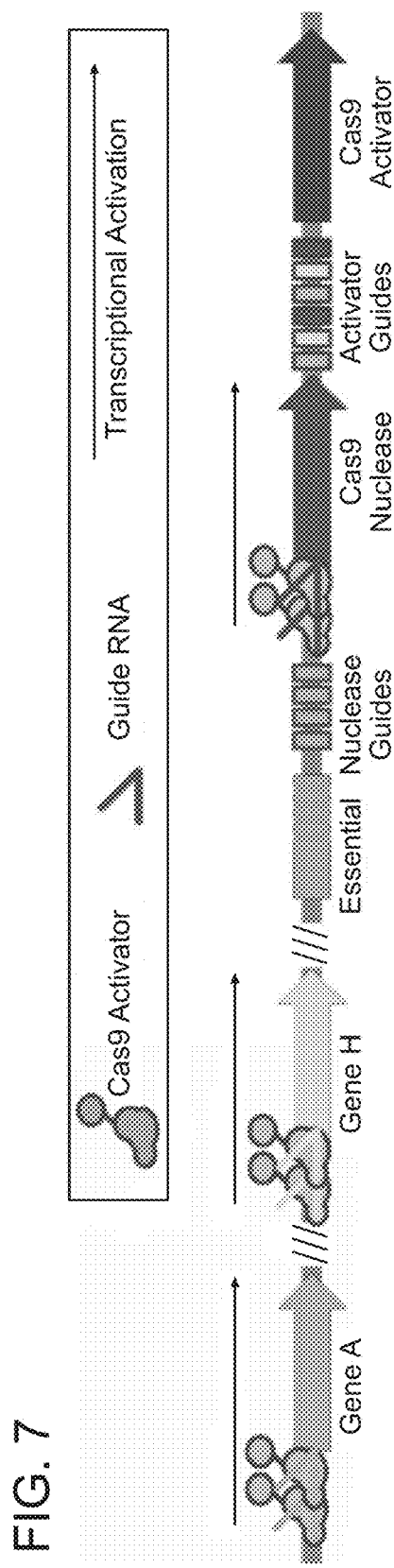
FIG. 7 depicts drive-mediated regulating of endogenous genes where RNA-guided transcriptional regulators can modulate the activity of distant genes without editing their sequence. Regulation will be evolutionarily stable during the lifetime of the drive if the drive nuclease requires the regulator for proper expression.

According to certain aspects of the present disclosure, an RNA-guided gene drive can edit multiple endogenous alleles distal to the drive itself by incorporating guide RNAs that target the respective wild-type alleles. As shown in FIG. 2A, multiple guide RNAs are provided for a plurality of gene sequences, i.e., Gene A WT, Gene B WT and Essential Gene WT. Expression of the multiple guide RNAs and the Cas9 protein results in each of the genes being modified by Cas9. According to one aspect, the Cas9 drive may also include one or more orthogonal nuclease null Cas9 proteins and associated guide RNAs with transcriptional regulators which can colocalize to a target DNA site so that the transcriptional regulator can regulate the gene. See FIG. 7. As shown in FIG. 2B, additional subsequent Cas9 drives can be used to update the changes that have been previously made by a prior Cas9 drive. For example, if a particular drive causes unexpected side effects, a second drive released as an update can overwrite one or all modifications encoded by the first drive. According to this aspect, the second drive can be designed to remove the existing inserted drive and then itself be inserted into the chromosome. In addition, one or more genes that have been modified by a prior RNA guided gene drive may be removed and replaced with a desired gene. Similarly, as depicted in FIG. 2C, a third restorative drive can restore the wild type sequence in all genomic locations except for the presence of the Cas9 gene and guide RNAs required to spread the restorative drive. In this manner, a population can be modified to revert back to its wild type. Accordingly, aspects of the present disclosure are directed to the modification or replacing of a previously inserted RNA guided Cas9 gene drive by introducing a second RNA guided Cas9 gene drive into a previously modified cell using the methods described herein. The second gene drive is designed to make further modifications beyond those made by the first gene drive or to eliminate the modifications made by the first gene drive.

Example III

Controlling Spread

According to certain aspects, the spread of RNA-guided gene drives can be limited to a single target species or even a subpopulation by targeting a unique gene or sequence polymorphism associated with the single target species or subpopulation. Because the drive can only cut the unique sequence, it does not spread through non-target populations. Accordingly, aspects of the present disclosure are directed to methods of designing and using RNA guided gene drives that are specific for a unique gene sequence or sequence polymorphism. In this manner one or more guide RNA are designed to be complementary to the unique gene sequence or sequence polymorphism. In this manner, the DNA binding protein is restricted to localizing at the unique gene sequence or sequence polymorphism.

Example IV

Inducing Artificial Speciation

Figure 3:
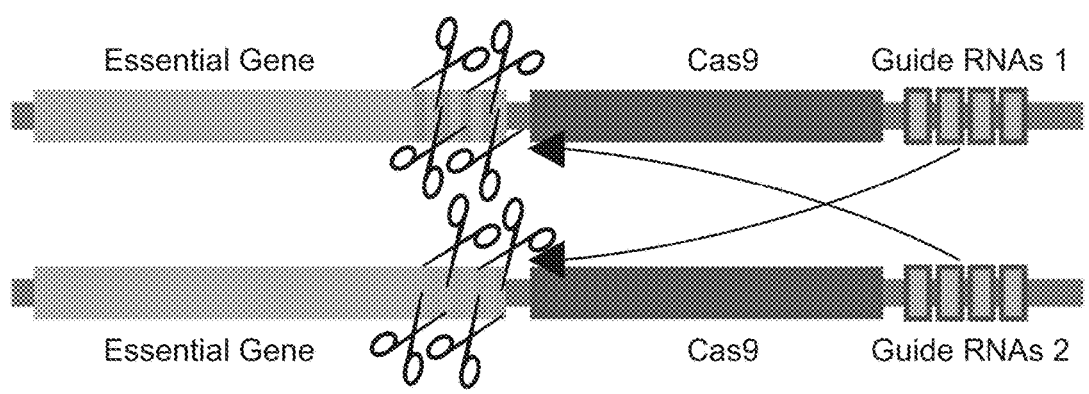
FIG. 3 depicts the use of two gene drives that target the same essential gene using different guide RNAs that become incompatible when crossed due to the loss of both copies. Releasing this type of drive into a population will artificially split it into as many species as there are drives.

According to certain aspects, methods are provided of using RNA-guided gene drives to block gene flow by causing genetic incompatibility between two populations. According to this aspect and as shown in FIG. 3, two gene drives that target different sequences within the same essential gene using different guide RNAs are released into two populations. The two populations become incompatible because of the loss of each copy of the essential gene within each population. Releasing this type of drive into a population will artificially split it into as many species as there are drives. As shown in exemplary FIG. 3, drive A cuts sequences 1, 2, 3, and 4 within essential gene X. As drive A spreads, it replaces gene X with a version that has sequences 1, 2, 3, and 4 recoded so they can not be cut. Drive B cuts sequences 5, 6, 7, and 8 within gene X, and its version of gene X has these sequences recoded so they can not be cut. Crossing a male with drive A and a female with drive B results in progeny that inherit one chromosome with drive A and gene X with 1/2/3/4 recoded, and one chromosome with drive B and gene X with 5/6/7/8 recoded. Drive A cuts the second copy of gene X at sites 1/2/3/4, because the second copy doesn't have those sites recoded—it only has 5/6/7/8 recoded. Similarly, drive B cuts the first copy of gene X at sites 5/6/7/8 because the first copy doesn't have those sites recoded, it only has 1/2/3/4 recoded. The organism ends up with both copies of gene X cut. Since gene X is essential and the organism lacks an intact copy of gene X to fix them with, the organism dies. Drive A and drive B are accordingly incompatible.

According to this aspect, each drive encodes a different version of the essential gene—a first foreign nucleic acid sequence and a second foreign nucleic acid sequence—that each preserve the amino acid sequence of the essential protein encoded by that gene, but which have different sets of target locations recoded—the first drive has sites 1/2/3/4 recoded to be noncomplementary to guides 1/2/3/4, whereas the second drive has sites 5/6/7/8 recoded to be noncomplementary to guides 5/6/7/8. When the drives are crossed, the first drive cleaves the second drive's copy of the essential gene at 1/2/3/4 because it doesn't have those sites recoded, while the second drive cleaves the first drive's copy of the essential gene at 5/6/7/8 because it doesn't have those sites recoded.

Figure 8A:
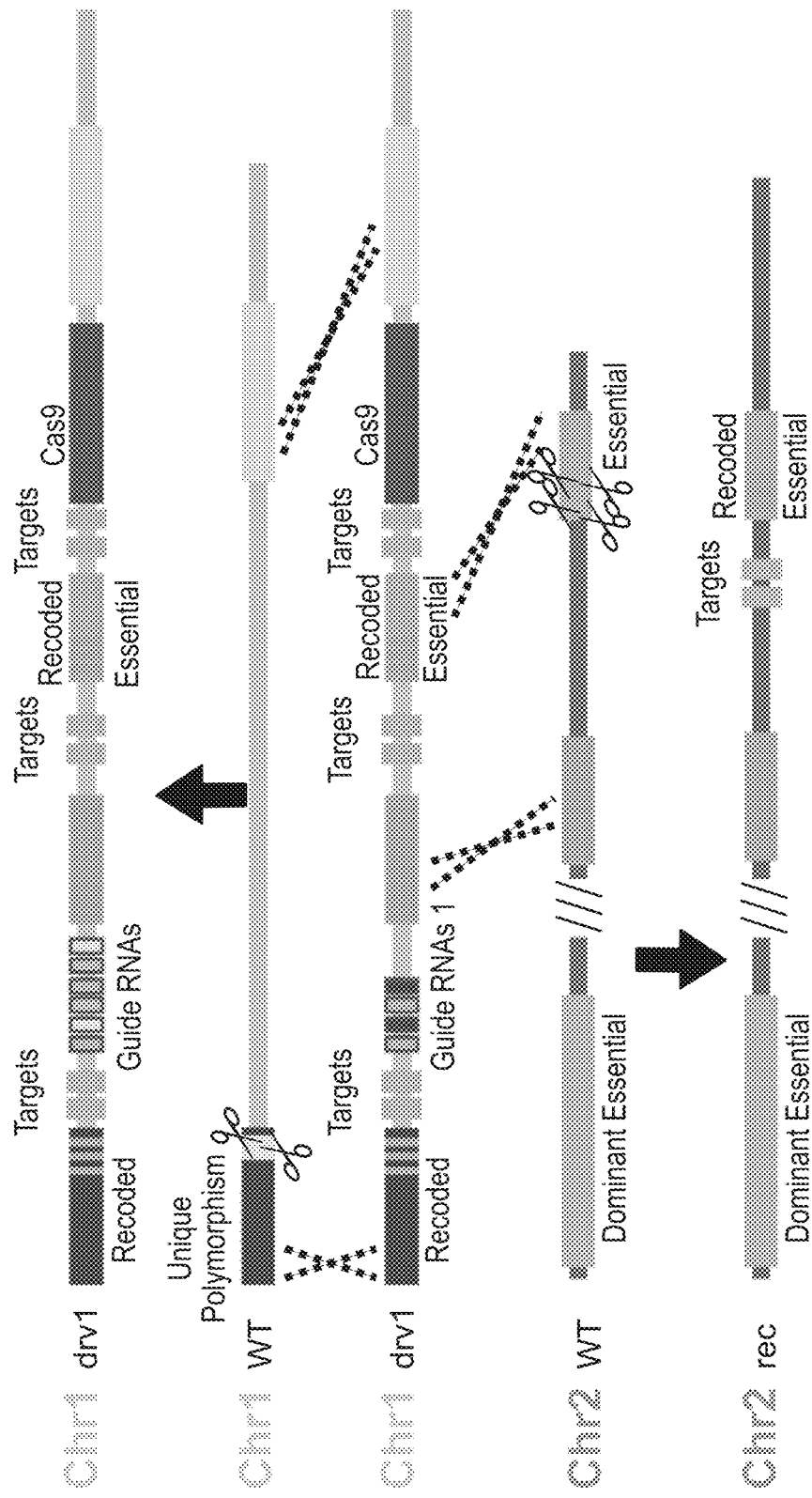
FIGS. 8A-8C depict inducing speciation from an unmodified wild-type population. Two successive gene drives targeting a subpopulation bearing a unique allele (depicted as a unique gene) can induce genetic incompatibility with the remaining wild-type population. The first drive spreads using the unique allele and recodes a gene that displays a dominant lethal phenotype when disrupted. The second drive spreads using the recoded gene and eliminates the first drive. Any mating with a wild-type organism causes the second drive to disrupt the wild-type copy, causing lethality in all progeny.
Figure 8B:
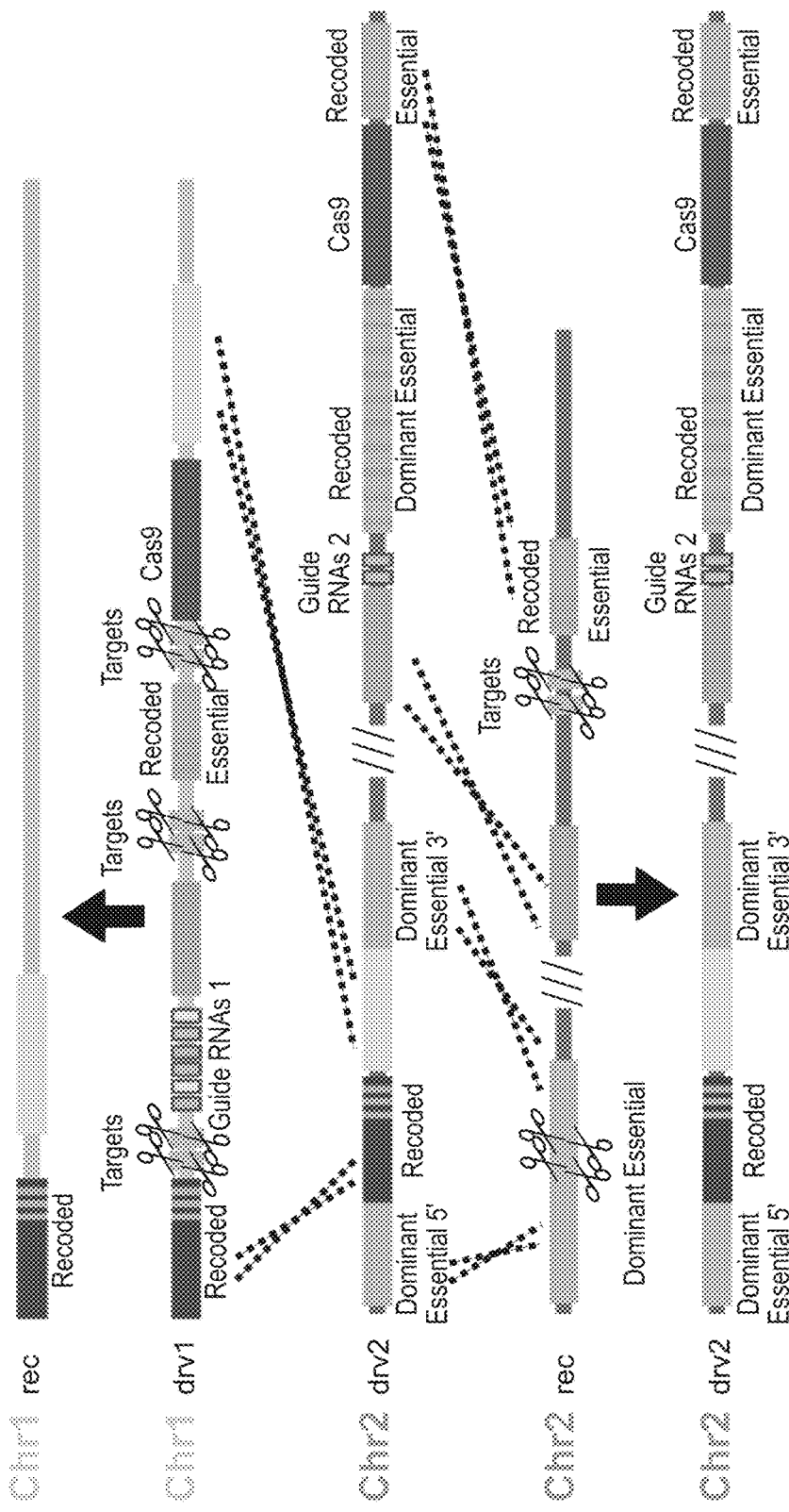
Figure 8C:
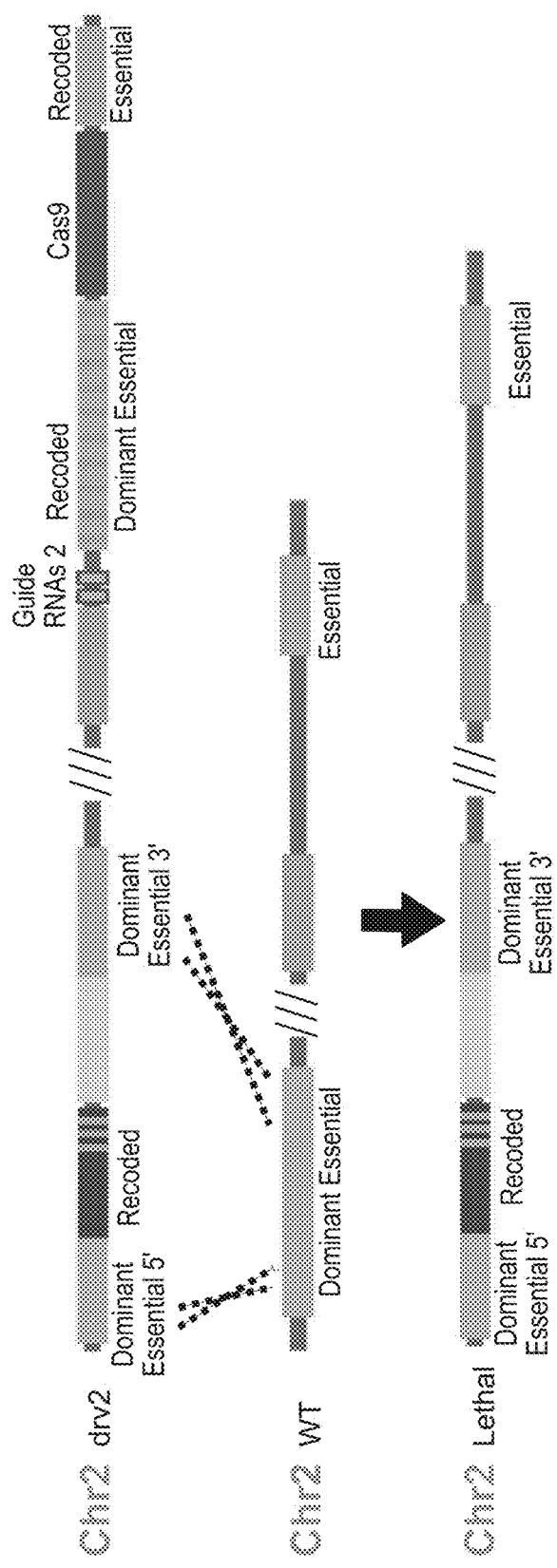
Figure 9B:
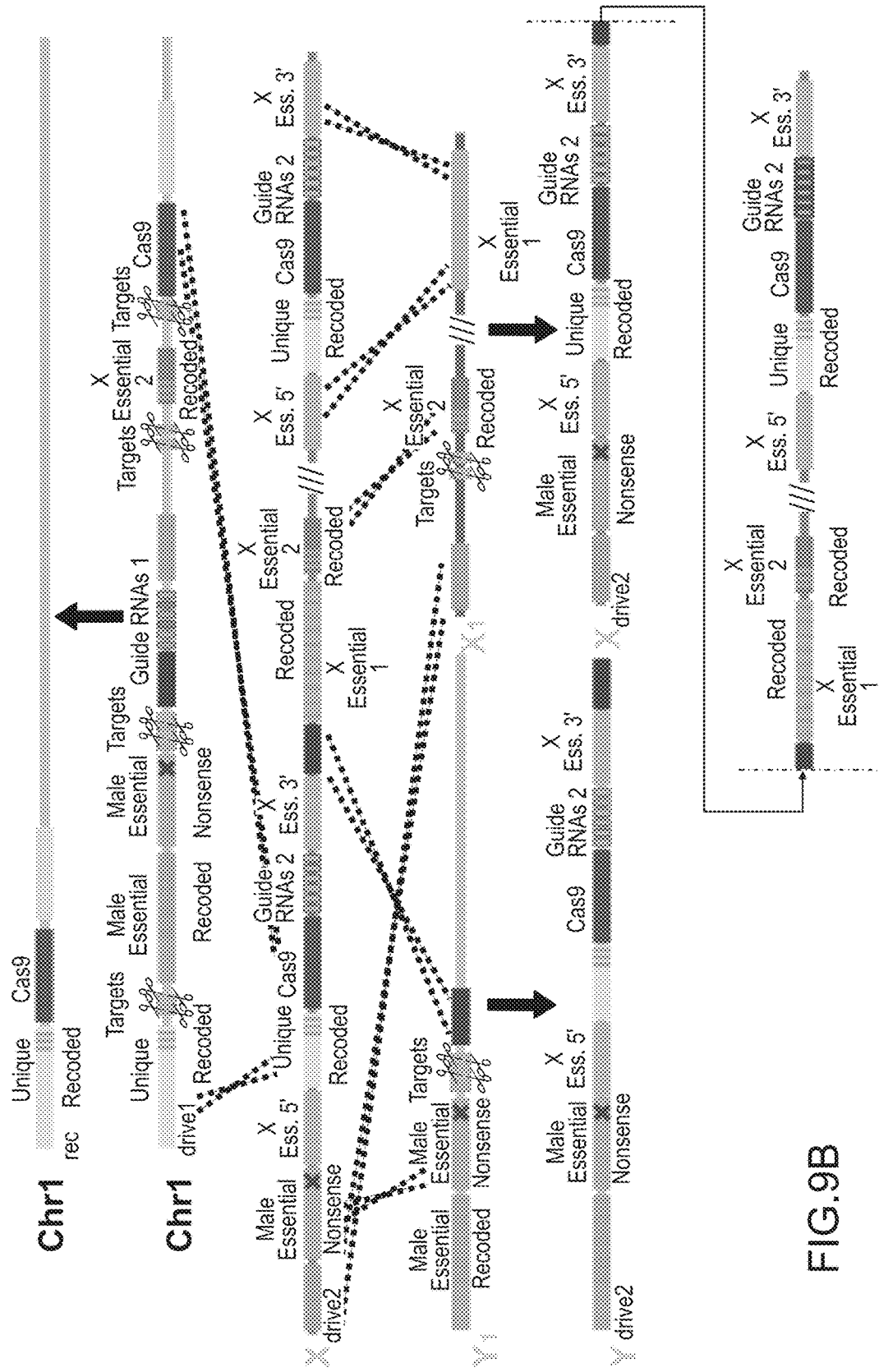

More complex gene drives can block gene flow between an engineered subpopulation and the wild-type population without modifying the latter (see FIG. 8). This barrier can even be one-way, allowing the engineered population to receive but not donate genetic material to the wild-type population (see FIG. 9). These or related designs might be used to prevent other gene drives or genetic modifications from spreading to unmodified members of the same or related species. According to this aspect, only one of the two populations are modified and two separate RNA guided gene drives are used. The first drive creates an insertion site for the second drive. The second drive 1) includes a copy of an essential gene, such that it copies that gene as it spreads into the insertion site created by the first drive, and 2) kills the wild-type copy of that essential gene. When an organism with the second drive mates with an organism with the first drive, the second drive is copied into the insertion site created by the first drive, adding a copy of the essential gene and removing the wild-type copy. Net change in essential genes is 0, so the cell is viable. When an organism with the second drive is mated with a wild-type organism, the drive and its essential gene is unable to be inserted into the wild-type chromosome because it lacks an insertion site. However, the second drive still kills the wild-type copy. Net change in essential genes is −1, so the cell dies. Accordingly, any matings between organisms containing the second drive and wild-type organisms produce no progeny. This aspect of the disclosure provides a method of making transgenic organisms incompatible with the wild-type population to prevent the spread of transgenes.

Example V

Population Suppression and Extinction

According to certain aspects, RNA-guided nucleases can create several different forms of sex-biasing gene drives that may be useful for population control. As shown in FIG. 4A, expressing Cas9 and guide RNAs targeting the X chromosome exclusively during male meiosis will result in a classical "meiotic" Y-drive analogous to those found in nature. The meiotic gene drive eliminates the competing sex chromosome during meiosis, producing a biased pool of gametes. Drive expression must be strictly limited to pre-meiosis or the drive will be lethal. This type of drive can bias the gametes of organisms employing XY, ZW, and to a lesser extent XO sex-determination systems in favor of either sex. Further with respect to FIG. 4A, an RNA guided gene drive is introduced into the Y chromosome of a spermatocyte. The RNA guided gene drive includes a plurality of guide RNA complementary to target sequences on the X chromosome. When the RNA guided gene drive is expressed, the guide RNAs and the Cas9 nuclease colocalize at the X chromosome where the Cas9 nuclease creates double stranded breaks rendering the X chromosome inoperable. After meiosis, only sperm having the Y chromosome will be viable.

Importantly, orthogonal Cas9 nucleases should be capable of circumventing meiotic chromosome silencing. Aspects of the present disclosure are directed to the use of a first RNA guided gene drive as described herein on a Y chromosome to express Cas9 with suitable guide RNA prior to generation of sperm where the expressed Cas9 and the suitable guide RNA cuts an autosome and a second RNA guided gene drive encoding a second Cas9 and suitable guide RNA is inserted into the autosome. During spermatogenesis, the second RNA guided gene drive in the autosome is expressed and the expressed second Cas9 and suitable guide RNA cuts the X chromosome thereby rendering it inoperable. This method allows the cutting of the X chromosome even in species in which the X and Y chromosomes are not expressed during spermatogenesis. As shown in FIG. 4B, Cas9 causes the cassette encoding Cas9B to be copied from the sex chromosome to an autosome early in development, where it is free to eliminate the competing sex chromosome during meiosis. According to one aspect, RNA guided gene drives that bias for a particular sex are provided on the sex chromosome which they bias the population towards. For example, males have Y chromosomes in mammals, so a drive that biases populations towards males has to be on the Y chromosome, as it then assists the Y chromosome make more copies of itself. As mammalian sex chromosomes are not expressed during meiosis (sperm and egg formation), two copies of Cas9 can be used to facilitate proper insertion of the drives into a chromosome which when expressed will produce a Cas9 that will cut the sex chromosome. The first Cas9 acts early in development, well before sperm formation, and it cuts an autosome (non sex chromosomes that are not silenced during meiosis) thereby allowing insertion of an RNA guided gene drive encoding a second Cas9 into the autosome. This second Cas9 is expressed from the autosome during sperm formation and cuts the X chromosome, thereby ensuring that most viable sperm contain the Y chromosome. Thy above described method therefore uses two RNA guided gene drives where one is inserted into an expressable autosome to bias populations towards males in the situation where sex chromosomes can't express genes during meiosis.

As shown in FIG. 4C, "zygotic" sex-biasing drives eliminate opposite-sex siblings during the zygotic or post-zygotic stage (see Rice and Friberg 2008 hereby incorporated by reference in its entirety). Importantly, they do not require highly specific expression patterns in order to function. X-drives eliminate male zygotes by simply targeting sites on the Y chromosome (FIG. 4C). In Y-drives, a gene drive cassette copies itself in place of an essential gene on the X chromosome, the loss of which is complemented in males by a copy inserted elsewhere on the driving Y chromosome (FIG. 4D). It may be necessary to adjust expression of the transplanted essential gene to account for dosage compensation in some species.

With respect to FIG. 4C, a wild type spermatocyte creates a wild type sperm with an X chromosome and a wild type sperm with a Y chromosome. An oocyte is provided with an RNA guided gene drive with one or more guide RNAs complementary to the Y chromosome, which is referred to as an "X drive oocyte". When the wild type sperm with the Y chromosome is combined with the oocyte, the RNA guided gene drive is expressed, the guide RNA and the Cas9 nuclease colocalize to the Y chromosome where the Cas9 nuclease creates double stranded breaks in the Y chromosome rendering the Y chromosome inoperable and thereby producing an inoperable zygote. In contrast, when the wild type sperm with the X chromosome is combined with the oocyte, the RNA guided gene drive is expressed, guide RNA complementary to the X chromosome and the Cas9 nuclease colocalize to the X chromosome where the Cas9 nuclease creates double stranded breaks in the X chromosome which is repaired by homologous recombination thereby inserting the RNA guided gene drive into the X chromosome rendering the zygote homozygous for the X chromosome. This copy of the X chromosome remains viable because the double strand breaks are repaired when the RNA guided gene drive is copied. The resulting progeny are all female, because the males are not viable due to loss of the Y chromosome. These females have an advantage over other females that do not encode an RNA guided gene drive because they do not have to compete with male siblings for resources. Consequently, the X chromosome with an RNA guided gene drive has a fitness advantage.

With respect to FIG. 4D, zygotic Y-drives encode an essential gene normally found on the X chromosome and utilize a gene drive cassette to eliminate that essential gene from the X chromosome. The Y drive is inserted from the paternal to the maternal X chromosome, leaving female zygotes without any copies of the essential gene. In particular, a spermatocyte is provided with a Y chromosome having an essential gene from the X chromosome and an RNA guided gene drive encoding one or more guide RNAs complementary to the essential gene on the X chromosome. The X chromosome of the spermatocyte also includes the same RNA guided gene drive. The spermatocyte produces a sperm with the Y chromosome and a sperm with the X chromosome. The sperm with the Y chromosome is combined with a wild type oocyte having an X chromosome with the essential gene. When the RNA guided gene drive is expressed, the one or more guide RNAs colocalize with the Cas9 nuclease to the X chromosome where the Cas9 nuclease cuts out the essential gene from the X chromosome. However, since the essential gene from the X chromosome is present on the Y chromosome, the zygote will be viable. In contrast, when the sperm with the X chromosome including the RNA guided gene drive combines with the wild type oocyte with the X chromosome, the expressed one or more guide RNAs colocalize with the Cas9 nuclease to the X chromosome where the Cas9 nuclease cuts out the essential gene from the X chromosome. Since the essential gene no longer exists in the oocyte, the oocyte is not viable.

The fitness benefit of zygotic drives will vary depending on the degree of sibling competition, the extent of parental investment in offspring, and the mating dynamics in adults. All zygotic Y-drives should produce at least as many if not more sons than competing wild-type Y chromosomes, and none of those sons will have to compete with sisters. Unlike other drive types, the host range of zygotic Y-drives can be restricted by ensuring that matings with specific at-risk related species or non-targeted subpopulations are sterile. This can be accomplished by incorporating guide RNAs that cleave unique sequences on the X-chromosomes to eliminate hybrid males.

Releasing a Y-drive will render the local population extinct if mutations capable of blocking the drive do not quickly arise on the X chromosome or one of the autosomes. The drive can be halted and eventually eliminated by releasing organisms bearing sex chromosomes that are immune to cutting. Close monitoring and control can prevent total extinction.

Figure 10D:
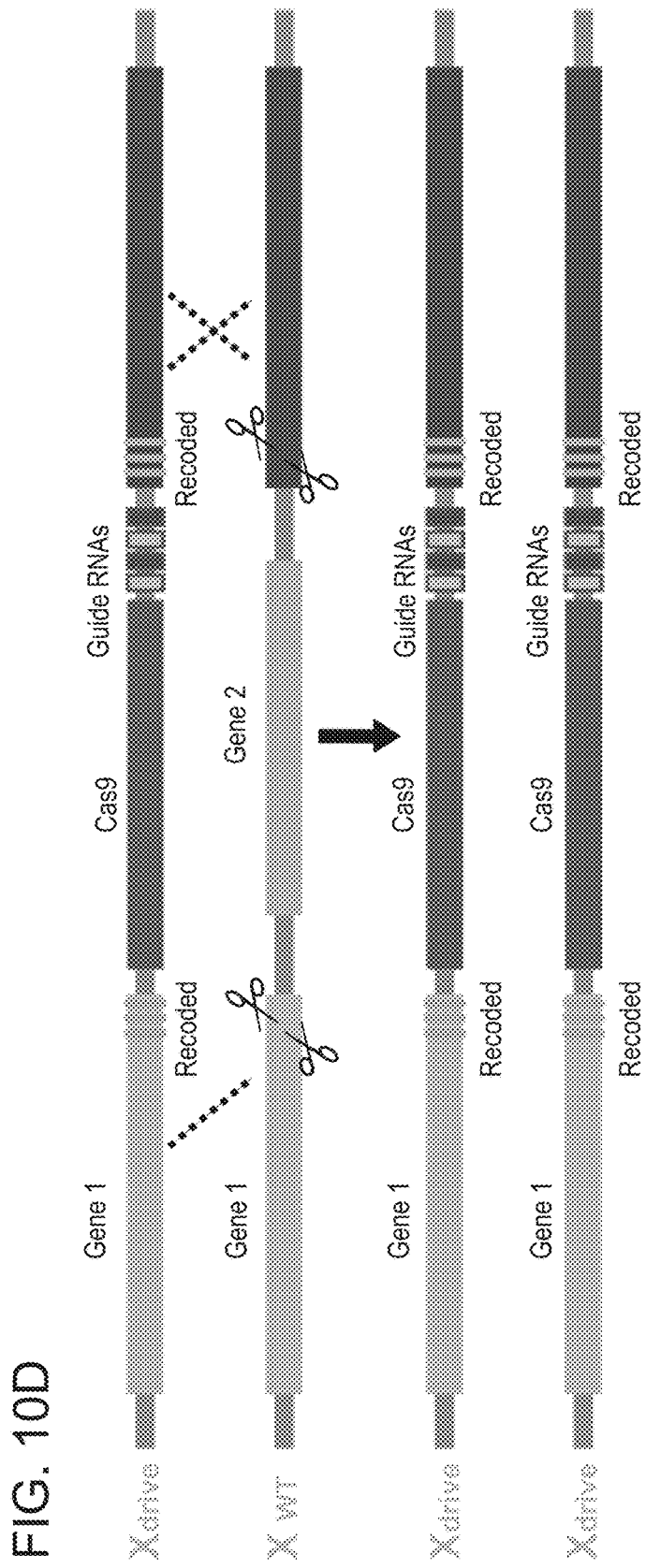

RNA-guided nucleases can also create less aggressive "sterile-daughter" Y chromosomes that can suppress populations but do not spread like a drive (FIG. 10A). A copy of Cas9 on the Y chromosome that targets an X-linked gene essential for female fertility rather than viability will still eliminate the reproductive potential of female progeny, but will provide no advantage to sons. Due to the minor cost of Cas9 activity, a sterile-daughter Y will eventually be outcompeted by the wild-type Y chromosome, but not before causing severe population suppression if introduced in sufficiently large numbers. This approach is closely related to the female-specific lethality and sterility methods being developed for the control of insect and fish populations, but is likely to be both more straightforward to construct and more evolutionarily stable due to its location on the Y.

Hybrid approaches to population control might combine the advantages of the Y-drive and sterile-daughter methods (FIG. 5A-B). For example, a Y chromosome that targets both an essential gene and a female fertility gene will quickly drive itself through the population because it is a Y-drive. However, it would lose its fitness advantage upon encountering a subsequently released standard gene drive that recodes the essential gene, but not the female fertility gene, on the X chromosome. Hybrid females will grow up to be infertile instead of dying embryonically, causing continued suppression without extinction.

A related approach to population control utilizes RNA-guided gene drives to disrupt one or more genes that are 1) required for fertility or viability, but 2) one intact copy largely suffices for function. Such a drive would cut and replace the target gene in the germline cells of organisms that inherit one copy of the drive and one copy of the wild-type gene at any time after the gene's function is required. For example, a gene required for gonad development and subsequent fertility might be cut and replaced by an RNA-guided gene drive just prior to meiosis. Since an organism that inherited only one copy would already have undergone correct gonad development because the wild-type copy suffices for this purpose, it would have normal fertility. However, most or all offspring would inherit the drive due to drive copying just prior to sperm and/or egg production. This design allows the drive to spread through the population when rare because most mating events will produce more individuals that inherit one copy of the drive and one copy of the wild-type. Later on, matings between two individuals that carry the drive will produce sterile offspring, leading to a population crash. This scenario has been modeled extensively as described in: Burt, A. Site-specific selfish genes as tools for the control and genetic engineering of natural populations. Proc. Biol. Sci. 270, 921-928 (2003). Deredec, A., Burt, A. & Godfray, H. C. J. The population genetics of using homing endonuclease genes in vector and pest management. Genetics 179, 2013-2026 (2008). North, A., Burt, A. & Godfray, H. C. J. Modelling the spatial spread of a homing endonuclease gene in a mosquito population. J. Appl. Ecol. 50, 1216-1225 (2013), each of which is hereby incorporated by reference in their entireties. Methods of restricting gene expression to germline cells and/or the time period prior to meiosis are known to those in the art.

Example VI

Applications

The gene drives described herein have particular practical utility in the eradication of infectious diseases and the control of invasive species. Such RNA guided Cas9 gene drives may be used to quickly spread protective alleles through threatened or soon-to-be-threatened species such as amphibians. Such RNA guided Cas9 gene drives may also be used to immunize wild populations that commonly serve as reservoirs for human viruses by targeting dsDNA viruses with Cas9 and RNA viruses with RNAi machinery from a foreign species carried by the drive. Disease vectors can be engineered to be unable to acquire the pathogen or can be eliminated using a Y drive described herein, i.e. an RNA guided Cas9 gene drive which inhibits propogation of an X chromosome. Similarly, invasive and ecologically destructive pests could be locally controlled or eradicated using Y-drives. Domesticated animals may be prevented from contributing genes to related wild species and feral populations controlled to minimize ecological damage and reduce the need for shelters and rescue agencies. Similarly, transgenic crops and animals could be genetically separated from their unmodified cousins, as could threatened species endangered by genetic dilution from more abundant or invasive relatives. Finally, gene drives could be used to directly test hypotheses concerning the evolutionary and ecological importance of genes, sex ratios, and speciation in natural environments.

The gene drives described herein have particular practical utility with vector born diseases. The human toll of vector-borne infectious disease is staggering. Malaria alone kills over 650,000 people each year, most of them children, while afflicting 200 million more with debilitating fevers that economically devastate their societies. Dengue, yellow fever, trypanosomiasis, leishmaniasis, Chagas disease, and Lyme disease are caused by others pathogens that spread using vectors. All of these can potentially be reduced or even eliminated by driving changes in the vector that prevent transmission. Scientists have identified several candidate gene disruptions or inserted genes that interfere with the transmission of malaria (Ito et al Nature 2002, PMID: 12024215: Dong et al PloS Pathogens 2012, PMID: 22216006; Isaacs et al., PNAS 2012, PMID: 22689959) and other well-studied diseases (Franz et al PNAS 2006, PMID: 16537508), but not for many other pathogens. Hence, aspects of the present disclosure are directed to directly eliminating the vector species with a Y-drive. In the case of malaria, this strategy is particularly promising against emerging mosquito vectors that prefer to bite and rest outdoors, as these behaviors are highly resistant to current control strategies focused around indoor insecticide spraying and bednets. Although all vector species must be targeted in a given area in order to stop transmission, the disease will be permanently eradicated if the newly vacated ecological niches are filled by competing non-vector species. Significantly, this strategy requires little or no understanding of the vector's molecular biology, but unavoidably entails the local or possibly global extinction of the vector species.

Figure 6A:
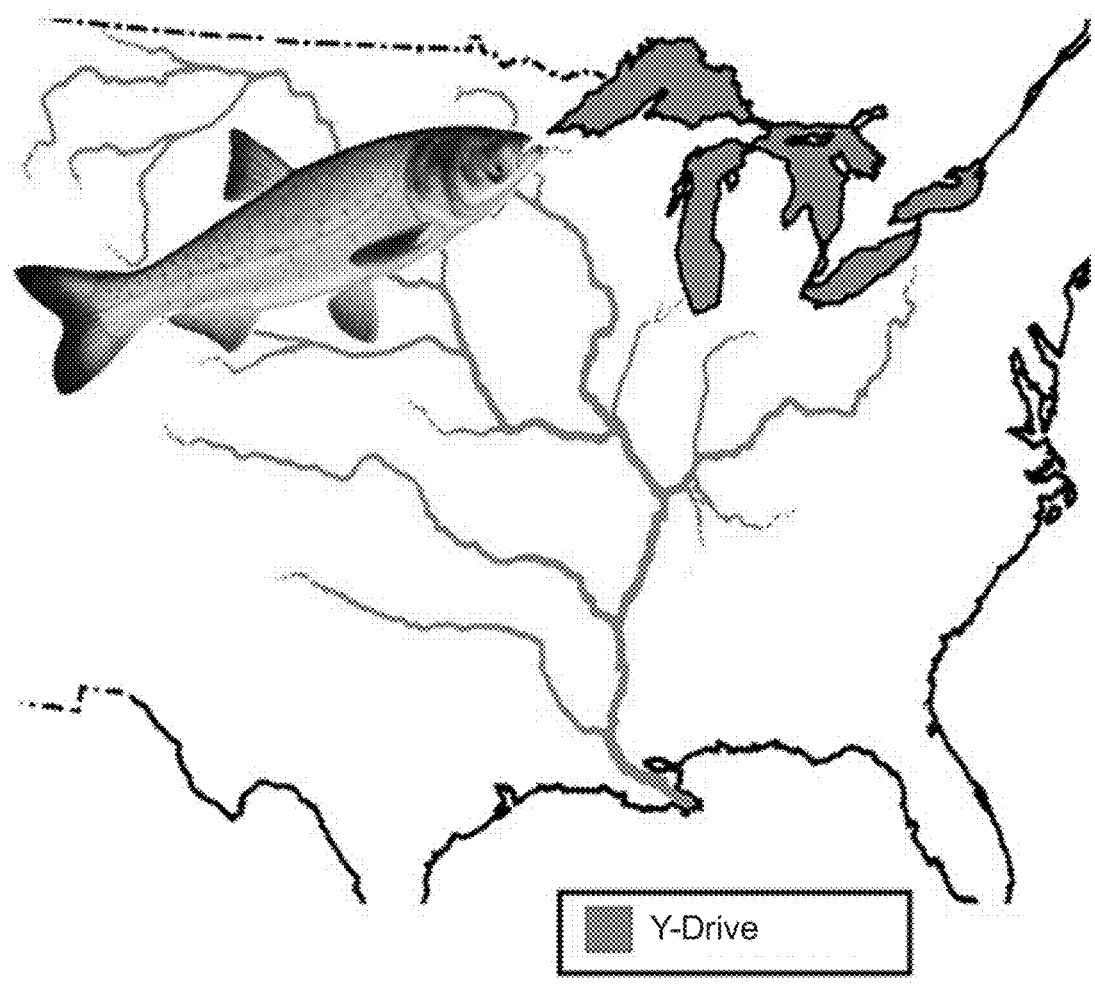
FIG. 6A depicts a method for controlling low- and high-mobility invasive species where Y-drive male Asian carp released throughout invaded habitats such as the Mississippi can be used to eradicate Asian carp populations. A protective recoding drive can be available to protect Asian populations in the event of deliberate human transport of Y-drive males.
Figure 6B:
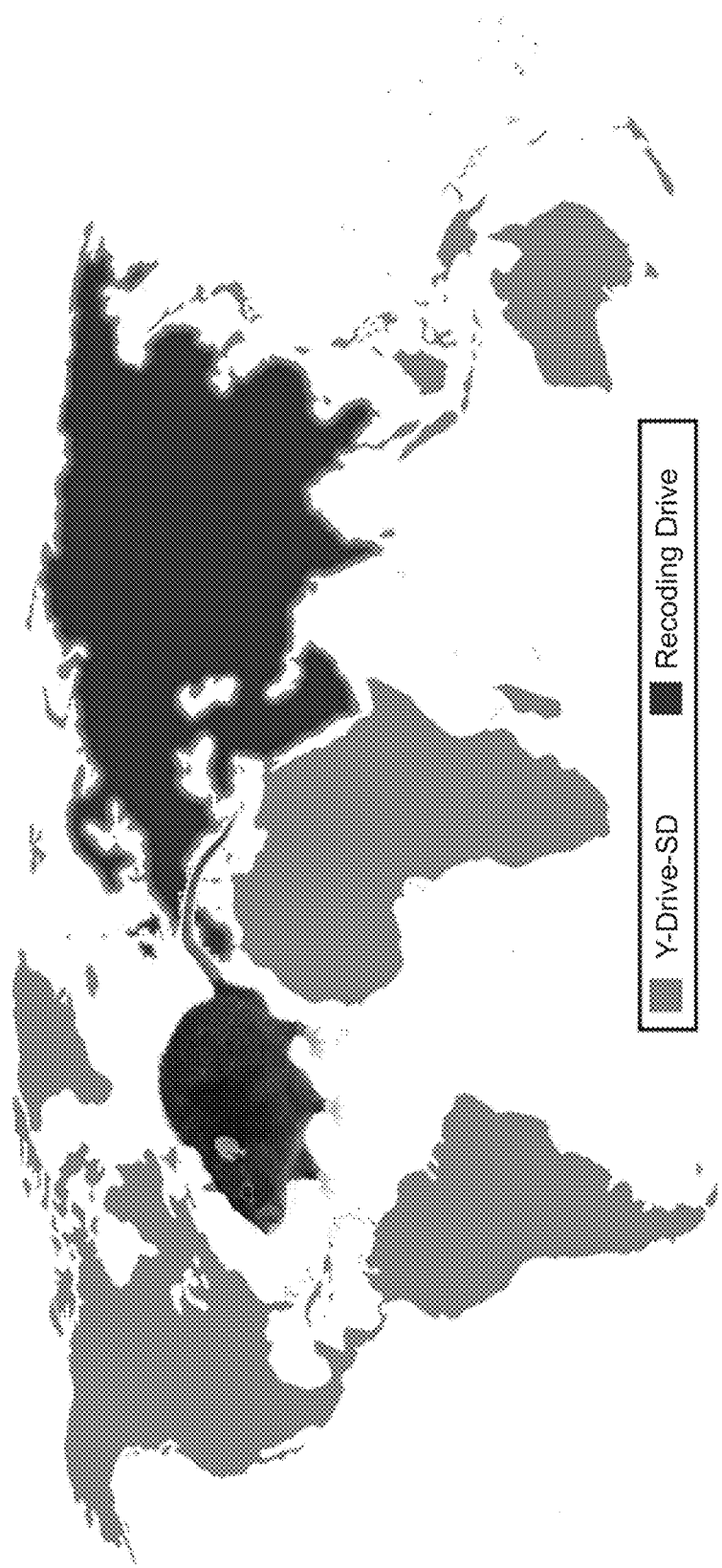
FIG. 6B depicts releasing Y-Drive-SD male rats into invasive rat populations which will initiate local eradication while a standard drive protectively recodes the native rat populations of Eurasia. The Y-Drive-SD construct will eradicate invasive rats from most islands and many continental areas. Stowaway-mediated gene flow will be limited by the sterile-daughter effect of Y-Drive-SD in recoded populations. The process can be repeated with new drives once recoded stowaways successfully invade rat-free habitats.

The gene drives described herein have particular practical utility in controlling invasive species. One of the most environmentally damaging consequences of global economic activity is the transport of invasive species, which often causes ecological disruption and the extinction of native species. Isolated ecosystems such as those on small islands are especially vulnerable. Cas9 Y-drives have tremendous potential to promote biodiversity by controlling or even eradicating these species from individual islands or possibly entire continents. Designing drive sequences unique to the invasive species, incorporating guide RNAs that will degrade the X chromosomes of at-risk relatives, and using speciation drives to render the target species genetically incompatible with its relatives target the drive to the selected species and reduce the risk of cross-species transfer without directly modifying all related species. Related species can be protected by releasing species-specific standard gene drives that recode the sites required for Y-drive function. The risk that the Y-drive might spread from the invasive population back into the native habitat is negligible for species that only invade through intentional human action, such as freshwater fish or cane toads, but Y-drive spread is all but certain for rats and other invasive stowaways. Native populations can always be protected from extinction by releasing an X-recoding drive or even a resistant X chromosome. As an example, invasive populations of low-mobility species such as Asian carp are excellent candidates for straightforward elimination by Y-drive. (FIG. 6A) Because gene flow would require deliberate human introduction, local eradication is likely to be permanent and achievable without being forced to recode the native population. In contrast, rats and other highly mobile invasive species cannot be permanently eliminated barring total extinction of the species. However, they might be controlled by periodically releasing a standard recoding drive in native populations and a Y-drive with sterile-daughter effect (Y-Drive-SD) throughout invasive populations (FIG. 6B).

Example VII

Agricultural Safety and Sustainability

Aspects of the present disclosure are directed to the use of the Cas9 methods described herein to control, reduce, or eliminate weeds and pests associated with agriculture. A pest generally refers to a plant or animal detrimental to humans or human concerns such as with agriculture or livestock production. The term pest may include any living organism which is invasive or prolific, detrimental, troublesome, noxious, destructive, a nuisance to either plants or animals, human or human concerns, livestock, human structures, wild ecosystems etc. The term pest may also include vermin, weed, plant and animal parasites and pathogens. A weed according to the present disclosure may refer to a plant considered undesirable in a particular situation. In a broad sense, a weed may be considered a pest that is a plant. Examples commonly are plants unwanted in human-controlled settings, such as farm fields, gardens, lawns, and parks. The term "weed" may also include any plant that grows or reproduces aggressively, or is invasive outside its native habitat.

According to one embodiment of the present disclosure, the Cas9 methods are used to insert into the genome of a germline cell of a weed or pest one or more RNA-guided "sensitizing drives." A sensitizing drive is a gene drive as described herein and may also be referred to as a "sensitizing gene drive." Accordingly, a "sensitizing drive" is a gene drive that is inserted into genomic DNA and which is transferred to progeny and renders the progeny sensitive to an external stimulus. According to one aspect, the RNA-guided "sensitizing drive" confers to the weed or pest as a result of being incorporated into genomic DNA a harmful sensitivity to a compound or chemical, such as toxicity. In this manner, the growth and proliferation of the weed or pest may be controlled by contacting the weed or pest with a compound or chemical or condition which ordinarily would not be toxic to the weed or pest. In this manner, the phenotype of the weed or pest has been altered by the sensitizing gene drive as a result of insertion of the gene drive into the germline cell and transfer to progeny. In this manner, the reference to a weed or pest may refer to the population that results from initial insertion of the sensitizing gene drive into the germline cell and mating with a wild type population. The resulting population may be referred to as an altered population or sensitized population or genetically altered population.

According to the present disclosure, the term "sensitivity" as it relates to a weed or pest means a harmful reaction, such as toxicity, to a compound or chemical or condition to which the weed or pest is exposed. The sensitizing drive is a gene drive as described herein that alters genomic DNA to result in a harmful reaction, such as toxicity, in response to a compound, chemical or condition to which the weed or pest is exposed. "Sensitizing drives" may also be referred to herein as "toxicity drives" or "toxicity gene drive" to the extent that a chemical, compound or condition is toxic to the weed or pest as a result of having the sensitizing drive or toxicity drive present in its genome. According to one aspect, the sensitizing drive or toxicity drive is exogenously added to the germline organism. In this manner, the sensitizing gene drive or toxicity gene drive is a foreign nucleic acid, even though, according to certain application, it may include a sequence native to the weed or pest species, but not present in the germline cell into which it is to be introduced. According to one aspect, the sensitizing drive or toxicity drive is a foreign nucleic acid that is exogenously added to the germline organism using an RNA guided DNA binding protein nuclease and associated guide RNA as described herein.

According to one aspect, the weed or pest may be resistant to a particular herbicide or pesticide or the weed or pest may have developed over time a resistance to the particular herbicide or pesticide. The evolution of weeds or pests to herbicides or pesticides is a major problem for agriculture. Methods described herein use RNA-guided "sensitizing drives" to confer sensitivity of the organism to a chemical, compound or condition that was previously nontoxic or of low toxicity to the organism, so that progeny of the organism will be sensitive to the chemical, compound or condition and the organism will die as a result of toxicity or proliferation will be lowered, or the organism will be rendered sterile so that it cannot reproduce. In this manner, a nucleic acid sequence within the sensitizing gene drive is expressed by the organism, such as a weed or pest, and the expression of the nucleic acid alters the phenotype of the organism rendering it vulnerable to the chemical, compound or condition.

According to an additional aspect, a sensitizing drive or drives are used to replace resistant alleles (such as those with resistance mutations) with their ancestral (or non-mutated) equivalents to restore sensitivity. Accordingly, an organism that has developed resistance to an herbicide or pesticide through mutation of an allele may be rendered sensitive to the herbicide or pesticide by removing the mutant form of the allele having resistance and replacing it with the non-mutant form having sensitivity. In this manner, the non-mutant form of the allele is foreign to the organism or population of organisms as it includes the mutant form of the allele. Accordingly, a sensitizing gene drive might reverse known mutations that confer resistance to existing pesticides or herbicides. RNA-guided gene drives are used to reverse genome alterations that have spread through populations of an organism. According to this aspect, releasing a second drive could overwrite one or all changes caused by a first drive, as described herein. In this manner, the population of organisms is characterized by the presence of a first gene drive and first nucleic acid sequence imparting a phenotype such as toxicity that was first introduced into a germline cell to produce that phenotype in progeny and which was then transferred to progeny. However, through mutations or otherwise, the phenotype is lost. In this context, a second gene drive with a second nucleic acid sequence imparting the same phenotype is introduced into a germline cell with or without the first nucleic acid being removed and the second nucleic acid sequence is carried through into progeny. In this manner, the first gene drive nucleic acid is overwritten by the second gene drive nucleic acid, for example, to result in toxicity, by reversing the mutation creating resistance.

According to an additional aspect, a sensitizing drive may carry a prodrug-converting enzyme that would render a prodrug molecule toxic to organisms that express the enzyme. In this manner, the enzyme is produced and should the organism be contacted with the prodrug, the enzyme will convert the prodrug into a compound or chemical that is toxic to the organism, such as a weed or pest. Various prodrug/enzyme combinations will be apparent to one of skill in the art based on the present disclosure.

According to a still additional aspect, a sensitizing drive may replace an essential gene for a version that is strongly inhibited by a particular small molecule. Accordingly, either expression of the gene would be inhibited or the expression product of the gene would be inhibited. Such inhibition may result in death of the organism or a lower proliferation. Because, in some embodiments, sensitizing drives would have no effect in the absence of their associated molecule—and in some cases vice versa—they could grant very fine control over the geography and extent of population suppression with minimal ecological risk.

According to one exemplary aspect, a sensitizing drive is used to reverse mutations allowing the western corn rootworm to resist Bt toxins (see Gassman et al PNAS, vol. 111 no. 14, pages 5141-5146, doi: 10.1073/pnas.1317179111 (2014) hereby incorporated by reference in its entirety) or horseweed and pigweed to resist the herbicide glyphosate (See Gaines, T. A. et al. Proc. Natl. Acad. Sci. 107, 1029-1034 (2010) and Ge, X., d'Avignon, D. A., Ackerman, J. J. & Sammons, R. D. Pest Manag. Sci. 66, 345-348 (2010) each of which are hereby incorporated by reference in their entireties), an herbicide currently essential to environmentally sustainable no-till agriculture. According to this aspect, organisms having the sensitizing drive are released into the wild population, individual organisms of which may or may not have resistance, and the sensitizing drive is carried through into progeny, the result of which is to decrease resistance of the progeny population (where resistance is present in the wild population) and increase sensitivity of the progeny population to a particular herbicide or pesticide (where resistance is present in the wild population.) It is to be understood that only some members of the wild type population may have resistance but that the sensitizing drive will spread through both sensitive and resistant members of the wild type population resulting in a progeny population having the sensitizing drive. According to one aspect, organisms including the sensitizing drive or drives would be released into areas not treated with herbicide or pesticide thereby creating reservoirs of sensitizing drives that could spread into adjacent areas which are treated with an herbicide or pesticide.

According to one aspect, methods are provided where a sensitizing drive or drives are used to counter mutations which lead to resistance. According to this aspect, introducing such sensitizing drives into the genome of a wild type population, initially and over subsequent time periods, that has developed resistance to a pesticide or herbicide as a result of a mutation or mutations reverses the effect of the mutation or mutations to provide resistance and renders the pesticide or herbicide toxic to the population. Such a method allows the use of any given herbicide or pesticide indefinitely because mutations conferring resistance are countered or replaced thereby "rolling back" whatever resistance may occur.

According to an additional aspect, a plant or animal may be rendered vulnerable to a chemical or compound or condition by the inclusion into its genome (and therefore its progeny) of a sensitizing drive or drives which renders the chemical, compound or condition toxic to the plant or animal, such as a weed or pest. Accordingly, compounds which may be considered safe to humans may be toxic to plants or animals as a result of the inclusion of a sensitizing drive or drives into the genome of the plant or animal thereby rendering the chemical or compound toxic to the plant or animal. According to this aspect, existing compounds considered safe and/or effective might be applied against organisms that are not presently vulnerable to them if a sensitizing drive were to deliver a sensitive gene from an affected species or laboratory isolate or replace a gene important for fitness with a sensitive gene.

According to a further aspect, methods are provided where sensitizing drives are used to render pest populations vulnerable to molecules, compounds or chemicals that are harmless to other forms of life. Whereas current pesticides and herbicides—even those designated as "organic"—are chosen for their toxicity towards insect pests and weeds, they often harm non-pest species or even humans because the affected pathways are conserved across species. According to the present disclosure, methods are provided where a gene or genes are delivered that confer sensitivity to an organism to a normally harmless molecule. Introduction of the sensitivity gene drive effectively converts that molecule into a pesticide or herbicide highly specific for the particular pest or weed species modified by the drive. The combination of the drive and the molecule is lethal to the organism. One exemplary embodiment is the use of an enzyme/prodrug combination where the enzyme is introduced in the genome of the organism and is expressed. When the organism is exposed to the prodrug, the enzyme converts the prodrug into an active herbicide or pesticide. Analogous candidates demonstrating the principle for this aspect of the present disclosure are antiviral or anticancer therapies in which a locally produced viral or tumor-specific enzyme activates a prodrug. Examples include the cytosine deaminase/5-fluorocytosine pairing and the nitroreductase/CB1954 pairing. In the case of sensitizing drives, the enzyme would be delivered to the target species by the gene drive, causing the prodrug to become a specific pesticide. Another exemplary pairing includes primary metabolic enzymes altered to become strongly inhibited by particular chemicals. For example, an engineered invertase may become nonfunctional in the presence of a mostly biologically inert xenobiotic chemical such as sucralose or related halogenated polysaccharides. A sensitizing drive would replace the organism's natural invertase gene with the engineered version, rendering it sensitive to the otherwise mostly inert compound. One of skill would readily be able to identify useful enzyme/chemical pairings suitable for this purpose based on the sensitizing drive methods described herein.

One of skill will readily be able to identify weeds within the scope of the present disclosure as including those weed plants harmful to agricultural crops. Such weeds may or may not be designated as "noxious weed" under federal or state law. For example, horseweed and pigweed are considered weeds that are harmful to agricultural crops but may not be designed as noxious weeds. Exemplary weeds designated as noxious weeds by the USDA include the following.

| Latin Name | Common Name(s) |
| --- | --- |
| *Azolla pinnata* | Mosquito fern, water velvet |
| *Caulerpa taxifolia* Mediterranean strain) | Killer algae |
| *Eichhornia azurea* | Anchored waterhyacinth, rooted waterhyacinth |
| *Hydrilla verticillata* | Hydrilla |
| *Hygrophila polysperma* | Miramar weed |
| *Ipomoea aquatica* | Water-spinach, swamp morning glory |
| *Lagarosiphon major* | African elodea |
| *Limnophila sessiliflora* | Ambulia |
| *Melaleuca quinquenervia* | Broadleaf paper bark tree |
| *Monochoria hastata* | Arrowleaf false pickerelweed |
| *Monochoria vaginalis* | Heartshape false pickerelweed |
| *Ottelia alismoides* | Duck lettuce |
| *Sagittaria sagittifolia* | Arrowhead |
| *Salvinia auriculata* | Giant *salvinia* |
| *Salvinia biloba* | Giant *salvinia* |
| *Salvinia herzogii* | Giant *salvinia* |
| *Salvinia molesta* | Giant *salvinia* |
| *Solarium tampicense* | Wetland nightshade |
| *Sparganium erectum* | Exotic bur-reed |

| Latin Name | Common Name(s) |
| --- | --- |
| *Aeginetia* spp. | Varies by species |
| *Alectra* spp. | Varies by species |
| *Cuscuta* spp. (except for natives) | Dodders |
| *Orobanche* spp. (except for natives) | Broomrapes |
| *Striga* spp. | Witchweeds |

| Latin Name | Common Name(s) |
| --- | --- |
| *Acacia nilotica* | Prickly acacia |
| *Ageratina adenophora* | Crofton weed |
| *Ageratina riparia* | Mistflower, spreading snakeroot |
| *Alternanthera sessilis* | Sessile joyweed |
| *Arctotheca calendula* | Capeweed |
| *Asphodelus fistulosis* | Onionweed |

-continued

| Latin Name | Common Name(s) |
|---|---|
| *Avena sterilis* | Animated oat, wild oat |
| *Carthamus oxyacantha* | Wild safflower |
| *Chrysopogon aciculatus* | Pilipiliula |
| *Commelina benghalensis* | Benghal dayflower |
| *Crupina vulgaris* | Common crupina |
| *Digitaria scalarum* | African couchgrass, fingergrass |
| *Digitaria velutina* | Velvet fingergrass, annual couchgrass |
| *Drymaria arenariodes* | Lightning weed |
| *Emex australis* | Three-corned jack |
| *Emex spinosa* | Devil's thorn |
| *Euphorbia terracina* | False caper, Geraldton carnation weed |
| *Galega officinalis* | Goatsrue |
| *Heracleum mantegazzianum* | Giant hogweed |
| *Imperata brasiliensis* | Brazilian satintail |
| *Imperata cylindrica* | Cogongrass |
| *Inula britannica* | British yellowhead |
| *Ischaemum rugosum* | Murainograss |
| *Leptochloa chinensis* | Asian sprangletop |
| *Lycium ferocissimum* | African boxthorn |
| *Lygodium flexuosum* | Maidenhair creeper |
| *Lygodium microphyllum* | Old world climbing fern |
| *Melastoma malabathricum* | Malabar melastome |
| *Mikania cordata* | Mile-a-minute |
| *Mikania micrantha* | Bittervine |
| *Mimosa invisa* | Giant sensitive plant |
| *Mimosa pigra* | Catclaw mimosa |
| *Moraea collina* | Cape tulip |
| *Moraea flaccida* | One leaf cape tulip |
| *Moraea miniata* | Two leaf cape tulip |
| *Moraea ochroleuca* | Apricot tulip |
| *Moraea pallida* | Yellow tulip |
| *Nassella trichotoma* | Serrated tussock |
| *Onopordum acaulon* | Stemless thistle |
| *Onopordum illyricum* | Illyricum thistle |
| *Opuntia aurantiaca* | Jointed prickly pear |
| *Oryza longistaminata* | Red rice |
| *Oryza punctata* | Red rice |
| *Oryza rufipogon* | Red rice |
| *Paspalum scrobiculatum* | Kodo-millet |
| *Pennisetum clandestinum* | Kikuyugrass |
| *Pennisetum macrourum* | African feathergrass |
| *Pennisetum pedicellatum* | Kyasumagrass |
| *Pennisetum polystachion* | Missiongrass, thin napiergrass |
| *Prosopis alpataco* | Mesquite |
| *Prosopis argentina* | Mesquite |
| *Prosopis articulata* | Velvet mesquite |
| *Prosopis burkartii* | Mesquite |
| *Prosopis caldenia* | Calden |
| *Prosopis calingastana* | Cusqui |
| *Prosopis campestris* | Mesquite |
| *Prosopis castellanosii* | Mesquite |
| *Prosopis denudans* | Mesquite |
| *Prosopis elata* | Mesquite |
| *Prosopis farcta* | Syrian mesquite |
| *Prosopis ferox* | Mesquite |
| *Prosopis fiebrigii* | Mesquite |
| *Prosopis hassleri* | Mesquite |
| *Prosopis humilis* | Algaroba |
| *Prosopis kuntzei* | Mesquite |
| *Prosopis pallida* | Kiawe, algarroba |
| *Prosopis palmeri* | Mesquite |
| *Prosopis reptans* | Tornillo |
| *Prosopis rojasiana* | Mesquite |
| *Prosopis ruizlealii* | Mesquite |
| *Prosopis ruscifolia* | Mesquite |
| *Prosopis sericantha* | Mesquite |
| *Prosopis strombulifera* | Argentine screwbean |
| *Prosopis torquata* | Mesquite |
| *Rottboellia cochinchinensis* | Itchgrass |
| *Rubus fruticosis* | Wild blackberry |
| *Rubus moluccanus* | Wild raspberry |
| *Saccharum spontaneum* | Wild sugarcane |
| *Sagittaria sagittifolia* | Arrowhead |
| *Salsola vermiculata* | Wormleaf salsola |
| *Senecio inaequidens* | South African ragwort |

-continued

| Latin Name | Common Name(s) |
|---|---|
| *Senecio madagascariensis* | Fireweed |
| *Setaria pumila* | Cattail grass |
| *Solanum torvum* | Turkeyberry |
| *Solanum viarum* | Tropical soda apple |
| *Spermacoce alata* | Winged false buttonweed |
| *Tridax procumbens* | Coat buttons |
| *Urochloa panicoides* | Liverseed grass |

Additional weeds within the scope of the present disclosure include Atriplex, Spreading; Beggarsticks, Nodding; Brome, Downy; Carrot, wild; Chamomile, scentless; Chickweed, common; Cucumber, bur; Dandelion; Fleabane, Canada; Flixweed; Grass, Stink; Grass, Tufted love; Groundcherry, Smooth; Hedge-nettle, Marsh; Horse-nettle; Horsetail, Field; Lettuce, Prickly; Mercury, Three-seeded; Muhly, Wire-stemmed; Nipplewort; Redtop; Sandbur, Long-spined; Smartweed, Swamp; Sow-thistle, Annual; Sow-thistle, Perennial; Speedwell, Corn; Vetch, Tufted; Violet, Field; Waterhemp, Common; Wood-sorrel species; Bermuda grass; Bindweed; Broadleaf plantain; Burdock; Common lambsquarters; Creeping Charlie; Dandelion; Goldenrod; Japanese Knotweed; Kudzu; Leafy spurge; Milk thistle; Poison ivy; Ragweed; Sorrel; Striga; St John's wort; Sumac; Tree of heaven; Wild carrot; Wood sorrel and Yellow nutsedge.

Additional weeds identified by scientific name include *Acalypha rhomboidea* Raf.; *Agrostis gigantea* Roth; *Amaranthus rudis* L.; *Atriplex patula* L.; *Bidens cernua* L.; *Bromus tectorum* L.; *Cenchrus longispinus* Hack.; *Conyza Canadensis*; *Daucus carota* L.; *Descurainia sophia* L.; *Equisetum arvense* L.; *Eragrostis* spp.; *Lactuca scariola* L.; *Lapsana communis* L.; *Matricaria perforata* Merat.; *Muhlenbergia frondosa* Poir.; *Oxallis dillenii* Jacq; *Physalis virginiana* Mill.; *Polygonum coccineum* Muhl.; *Sicyos angulatus* L.; *Solanum carolinense* L; *Sonchus arvensis* L.; *Sonchus oleraceus* L.; *Stachys palustris* L.; *Stellaria media; Taraxacum officinale* Weber.; *Veronica avensis* L.; *Vicia cracca* L.; and *Viola avensis* L.

It is to be understood that additional weeds within the scope of the present disclosure may be identified by sources readily available to those of skill in the art.

Common herbicides to which a weed may be resistant or develop resistance include the following. One of skill in the art will readily be able to identify herbicides toxic to particular weed species based on the present disclosure.

| Common or Code Name* | Trade Name | Manufacturer |
|---|---|---|
| Acetochlor | Harness | Monsanto |
| Acifluorfen | Blazer | BASF |
| Aclonifen | Challenge | Bayer CropScience |
| Acrolein | Magnacide | Baker |
| Alachlor | Lasso | Monsanto |
| Alloxydim | Fervin | Bayer CropScience |
| Ametryn | Evik | Syngenta |
| Amicarbazone | | Bayer CropScience |
| Amidosulfuron* | Adret, Gratil | Bayer CropScience |
| Aminocyclopyrachlor | MAT28/KJM44 | DuPont |
| Aminopyralid | Milestone | Dow AgroSciences |
| Amitrole | Amitrol T | Bayer CropScience |
| Anilofos | Aniloguard | Ghardat |
| Asulam | Asulox | Bayer CropScience |
| Atrazine | Aatrex | Syngenta |
| | Atrazine | Terra |
| Azimsulfuron | Gulliver | DuPont |

| Common or Code Name* | Trade Name | Manufacturer |
| --- | --- | --- |
| Beflubutamid | Herbaflex | Ube Industries |
| Benazolin | Asset | Bayer CropScience |
| Benefin | Balan | Dow AgroSciences |
| Bensulfuron | Londax | DuPont |
| Bensulide | Prefar | Gowan |
| Bentazon | Basagran | BASF |
| Benzofenap | Taipan | Bayer CropScience |
| Bifenox | Modown | Bayer CropScience |
| Bispyribac | Regiment, Velocity | Valent |
| Bromacil | Hyvar | DuPont |
| Bromoxynil | Buctril | Bayer CropScience |
| Butachlor | Machete | Monsanto |
| Butafenacil | Rebin, Inspire | Syngenta |
| Butroxydim | Falcon | Syngenta |
| Butylate | Sutan | Cedar |
| Cacodylic acid | Cotton-Aide HC | Monterey |
| Carbetamide | Carbetamex | Feinchemie |
| Carfentrazone | Aim, Shark, Quicksilver | FMC |
| Chlorsulfuron | Glean, Telar | DuPont |
| Chlortoluron | Dicuran | Syngenta |
| Cinmethylin | Argold, Cinch | BASF |
| Clethodim | Select, Prism | Valent |
| Clodinfop | Topik | Syngenta |
| Clodinafop-propargy* | Discover | Syngenta |
| Clomazone | Command | FMC |
| Clopyralid | Stinger, Lontrel | Dow AgroSciences |
| Cloransulam-methyl | Firstrate | Dow AgroSciences |
| Cyanazine | Bladex | DuPont |
| Cycloate | RoNeet | Cedar |
| Cyclosulfamuron | Invest | BASF |
| Cycloxydim | Focus | BASF |
| Cyhalofop | Clincher | Dow AgroSciences |
| DCPA | Dacthal | Amvac |
| 2,4-D | Several | Several |
| 2,4-DB | Several | Several |
| Dazomet | Basamid | BASF |
| Desmedipham | Betamix | Bayer CropScience |
| Desmetryn | Semeron | Syngenta |
| Dicamba | Banvel, Clarity | BASF |
| Dichlobenil | Casoron | Uniroyal |
| Dichlorprop | Several | Bayer CropScience |
| Diclofop | Hoelon | Bayer CropScience |
| Diclosulam | Strongarm | Dow AgroSciences |
| Difenzoquat | Avenge | BASF |
| Diflufenican | Javelin | Bayer CropScience |
| Diflufenzopyr | Distinct | BASF |
| Dimethenamid | Frontier | BASF |
| Diquat | Reward, Reglone | Syngenta |
| Dithiopyr | Dimension | Monsanto |
| Diuron | Karmex | DuPont |
| DSMA | Several | several |
| Endothall | Several | Atochem |
| EPTC | Eptam | Syngenta |
| Ethalfluralin | Sonalan | Dow AgroSciences |
| | Curbit | UAP |
| Ethametsulfuron | Muster | DuPont |
| Ethofumesate | Nortron, Prograss | Bayer Crop Science |
| Ethoxysulfuron | Sunrice | Bayer Crop Science |
| Fenoxaprop | Acclaim, Whip | Bayer CropScience |
| Fentrazamide | Lecs | Bayer CropScience |
| Flazasulfuron | Katana | Ishihara Sangyo |
| Florasulam | Frontline, Boxer | Dow AgroSciences |
| Fluazifop-P | Fusilade DX, Fusilade II | Syngenta |
| Flucarbazone-sodium | Everest | Arvesta |
| Flufenacet | Axiom (flufenacet + metribuzin) | Bayer CropScience |
| | Epic (flufenacet + isoxaflutole) | |
| Flufenpyr-ethyl* | S-3153 | Valent |
| Flumetsulam | Python, Broadstrike | Dow AgroSciences |
| Flumiclorac | Resource | Valent |
| Flumioxazin | BroadStar, Valor, Chateau | Valent |

| Common or Code Name* | Trade Name | Manufacturer |
| --- | --- | --- |
| Fluometuron | Cotoran | Syngenta |
| | Others | others |
| Flupyrsulfuron | Lexus | DuPont |
| Flurchloridone | Racer | Syngenta |
| Fluridone | Sonar | Dow AgroSciences |
| Fluroxypyr | Starane, Vista, Spotlight | Dow AgroSciences |
| Fluthiacet | Action | Syngenta |
| Fomesafen | Reflex, Flexstar | Syngenta |
| Foramsulfuron | Equip, Revolver | Bayer CropScience |
| Fosamine | Krenite | Dupont |
| Glufosinate | Liberty, Rely | Bayer CropScience |
| Glyphosate | Roundup, Ultra, Rodeo, Touchdown Pro | Monsanto, Syngenta |
| Halosulfuron | Permit, Battalion SedgeHammer | Monsanto Gowan |
| Haloxyfop | Verdict | Dow AgroSciences |
| Hexazinone | Velpar | DuPont |
| Imazamethabenz | Assert | BASF |
| Imazamox | Raptor, Clearcast | BASF |
| Imazapic | Cadre, Plateau | BASF |
| Imazapyr | Arsenal, Habitat | BASF |
| Imazaquin | Image, Scepter | BASF |
| Imazethapyr | Pursuit | BASF |
| Iodosulfuron | Husar | Bayer CropScience |
| Isoxaben | Gallery | Dow AgroSciences |
| Isoxaflutole | Balance | Bayer CropScience |
| Lactofen | Cobra | Valent |
| Linuron | Lorox | DuPont |
| | Others | others |
| MCPA | Several | several |
| MCPB | Several | several |
| Mecoprop | MCPP, Mecopex | several |
| Mesosulfuron | Osprey | Bayer CropScience |
| Mefluidide | Enable | 3M Company |
| Mesotrione | Callisto, Tenacity | Syngenta |
| Metham | Metham Sodium | Amvac |
| Metolachlor | Dual Dual Magnum, Pennant Magnum | Syngenta |
| Metribuzin | Sencor, Lexone | Bayer CropScience |
| Metsulfuron | Ally, Escort | DuPont |
| MSMA | Several | several |
| Napropamide | Devrinol | United Phosphorus |
| Naptalam | Alanap | Uniroyal |
| Nicosulfuron | Accent | DuPont |
| Norflurazon | Zorial, Solicam | Syngenta |
| Oryzalin | Surflan | Dow AgroSciences |
| Oxadiazon | Ronstar | Lesco |
| Oxasulfuron* | Expert | Syngenta |
| Oxyfluorfen | Goal | Dow AgroSciences |
| Paraquat | Gramoxone Inteon, Gramoxone Max | Syngenta |
| Pebulate | Tillam | Monterey |
| Pelargonic acid | Scythe | Dow AgroSciences |
| Pendimethalin | Prowl | BASF |
| Penoxsulam | Grasp, Granite | Dow AgroSciences |
| Phenmedipham | Spin-Aid | Bayer CropScience |
| Picloram | Tordon | Dow AgroSciences |
| Picolinafen* | Pico | BASF |
| Pinoxaden | Axial | Syngenta |
| Primisulfuron | Beacon | Syngenta |
| Prodiamine | Barricade | Syngenta |
| Prometon | Pramitol | Agriliance |
| Prometryn | Caparol | Syngenta |
| Pronamide | Kerb | Dow AgroSciences |
| Propanil | Stam | Dow AgroSciences |
| Propaquizafop | Shogun | Syngenta |
| Propoxycarbazone | Olympus | Bayer CropScience |
| Propazine | MiloPro | Griffin |
| Prosulfocarb | Boxer (in France) | Syngenta |
| Pyrasulfotole | Huskie | Bayer CropScience |
| Pyrazon | Pyramin | BASF |
| Pyrazosulfuron-ethyl* | Sirius | Bayer CropScience |
| Pyridate | Tough | Syngenta |

-continued

| Common or Code Name* | Trade Name | Manufacturer |
|---|---|---|
| Pyrithiobac | Staple | DuPont |
| Pyroxsulam | Powerflex | Dow AgroSciences |
| Quinclorac | Drive, Facet, Paramount | BASF |
| Quinmerac* | Fiesta | BASF |
| Quizalofop | Assure | DuPont |
| Rimsulfuron | Matrix, Basis, TranXit | DuPont |
| Saflufenacil | Kixor | BASF |
| Sethoxydim | Poast, Poast Plus | BASF |
| Siduron | Tupersan | DuPont |
| Simazine | Princep, others | Syngenta, others |
| Sulcotrione | Mikado, Galleon | Bayer CropScience |
| Sulfentrazone | Dismiss, Spartan, Authority | FMC |
| Sulfometuron | Oust | DuPont |
| Sulfosulfuron | Certainty, Monitor, Outrider, Maverick | Monsanto |
| Tebuthiuron | Spike | Dow AgroSciences |
| Tembotrione | Laudis | Bayer CropScience |
| Tepaloxydim | Equinox | BASF |
| Terbacil | Sinbar | DuPont |
| Terbutryn | Igran | Syngenta |
| Thiazopyr | Visor | Dow AgroSciences |
| Thifensulfuron | Pinnacle, Harmony | DuPont |
| Thiencarbazone | | Bayer CropScience |
| Thiobencarb | Bolero | Valent |
| Topramezone | Impact | Amvac |
| Tralkoxydim | Achieve | Syngenta |
| Triallate | FarGo | Monsanto |
| Triasulfuron | Amber, Fuego | Syngenta |
| Tribenuron | Express | DuPont |
| Triclopyr | Renovate | SeaPro |
| Trifloxysulfuron | Garlon, Envoke, Monument | Dow AgroSciences, Syngenta |
| Triflusulfuron | Upbeet | DuPont |
| Vernolate | Vernam | Drexel |

It is to be understood that additional herbicides within the scope of the present disclosure may be identified by sources readily available to those of skill in the art.

Pests within the scope of the present disclosure associated with corn include the following.

| Scientific Name | Common Name |
|---|---|
| Autographa gamma | Silver Y moth |
| Chilo suppressalis | Asiatic rice borer |
| Diabrotica speciosa | Cucurbit beetle |
| Harpophora maydis | Late wilt of corn |
| Helicoverpa armigera | Old world bollworm |
| Heteronychus arator | Black maize beetle |
| Peronosclerospora maydis | Java downy mildew |
| Peronosclerospora philippinensis | Philippine downy mildew |
| Punctodera chalcoensis | Mexican corn cyst nematode |
| Sclerophthora rayssiae var. zeae | Brown stripe downy mildew |
| Spodoptera littoralis | Egyptian cottonworm |
| Spodoptera litura | Cotton cutworm |
| Thaumatotibia leucotreta | False codling moth |

Pests within the scope of the present disclosure associated with cotton include the following.

| Scientific Name | Common Name |
|---|---|
| Anthonomus grandis | Boll weevil |
| Autographa gamma | Silver Y moth |
| Eutetranychus orientalis | Citrus brown mite |
| Helicoverpa armigera | Old World bollworm |
| Oxycarenus hyalinipennis | Cotton seed bug |
| Pectinophora gossypiella | Pink bollworm |
| Spodoptera littoralis | Egyptian cottonworm |
| Spodoptera litura | Cotton cutworm |
| Thaumatotibia leucotreta | False codling moth |

Pests within the scope of the present disclosure associated with oak include the following.

| Scientific Name | Common Name |
|---|---|
| Adoxophyes orana | Summer fruit tortrix moth |
| Aeolesthes sarta | City longhorned beetle |
| Agrilus biguttatus | Oak splendour beetle |
| Archips xylosteanus | Variegated golden tortrix |
| Epiphyas postvittana | Light brown apple moth |
| Lymantria dispar asiatica | Asian gypsy moth |
| Lymantria mathura | Rosy moth |
| Massicus raddei | Mountain oak longhorned beetle |
| Phytophthora quercina | Oak decline |
| Platypus quercivorus | Oak ambrosia beetle |
| Raffaelea quercivora | Japanese oak wilt |
| Scolytus intricatus | European oak bark beetle |
| Spodoptera littoralis | Egyptian cottonworm |
| Thaumatotibia leucotreta | False codling moth |
| Thaumetopoea processionea | Oak processionary moth |
| Tortrix viridana | Green oak tortrix |
| Tremex fuscicornis | Tremex woodwasp |

Pests within the scope of the present disclosure associated with pine include the following.

| Scientific Name | Common Name |
|---|---|
| Candidatus Phytoplasma pini 16SrXXI-A | Pine witches' broom |
| Cronartium flaccidum | Scots pine blister rust |
| Dendroctonus micans | Great spruce bark beetle |
| Dendrolimus pini | Pine-tree lappet |
| Dendrolimus punctatus | Masson pine moth |
| Dendrolimus sibiricus | Siberian silk moth |
| Diprion pini | Pine sawfly |
| Hylobius abietis | Large pine weevil |
| Lymantria mathura | Rosy moth |
| Monochamus saltuarius | Japanese pine sawyer |
| Monochamus sutor | Small white-marmorated longhorned beetle |
| Mycosphaerella gibsonii | Needle blight of pine |
| Panolis flammea | Pine beauty moth |
| Tomicus destruens | No common name, a pine shoot beetle |

Pests within the scope of the present disclosure associated with small grains include the following.

| Scientific Name | Common Name |
|---|---|
| Autographa gamma | Silver Y moth |
| Cernuella virgata | Maritime garden snail |
| Cochlicella spp. | Exotic species |
| Diabrotica speciosa | Cucurbit beetle |
| Helicoverpa armigera | Old world bollworm |
| Heterodera filipjevi | Cereal cyst nematode |
| Heterodera latipons | Mediterranean cereal cyst nematode |
| Heteronychus arator | Black maize beetle |
| Lobesia botrana | European grape vine moth |
| Meloidogyne artiellia | British root-knot nematode |
| Nysius huttoni | Wheat bug |

| Scientific Name | Common Name |
| --- | --- |
| *Peronosclerospora philippinensis* | Philippine downy mildew |
| *Spodoptera littoralis* | Egyptian cottonworm |
| *Spodoptera litura* | Cotton cutworm |

Pests within the scope of the present disclosure associated with soybean include the following.

| Scientific Name | Common Name |
| --- | --- |
| *Adoxophyes orana* | Summer fruit tortrix moth |
| *Alectra vogelii* | Yellow witchweed |
| *Autographa gamma* | Silver Y moth |
| *Cernuella virgata* | Maritime garden snail |
| *Chrysodeixis chalcites* | Golden twin spot moth |
| *Crocidosema aporema* | Bud borer |
| *Diabrotica speciosa* | Cucurbit beetle |
| *Eutetranychus orientalis* | Citrus brown mite |
| *Helicoverpa armigera* | Old world bollworm |
| *Spodoptera littoralis* | Egyptian cottonworm |

Pests within the scope of the present disclosure associated with grape include the following.

| Scientific Name | Common Name |
| --- | --- |
| *Adoxophyes orana* | Summer fruit tortrix moth |
| *Autographa gamma* | Silver Y moth |
| Candidatus *Phytoplasma australiense* 16SrXII-B | Australian grapevine yellows |
| *Cryptoblabes gnidiella Epiphyas postvittana Eupoecilia ambiguella* | Honeydew moth |
| Candidatus *Phytoplasma vitis* 1 *Heteronychus arator Lobesia botrana* | Light brown apple moth |
| *Pseudopezicula tracheiphila Spodoptera littoralis Spodoptera litura Thaumatotibia leucotreta* 6SrV-C | European grape berry moth |
|  | Flavescence dorée Black maize beetle European grape vine |

Pests within the scope of the present disclosure associated with palm include the following.

| Scientific Name | Common Name |
| --- | --- |
| *Bursaphelenchus cocophilus* | Red ring nematode |
| Candidatus *Phytoplasma palmae* 16SrIV | Palm lethal yellowing |
| Cocadviroid Coconut cadang cadang viroid | Coconut cadang cadang |
| *Darna pallivitta* | Nettle caterpillar |
| *Haplaxius crudus* | American palm cixiid |
| *Metamasius hemipterus* | West Indian cane weevil |
| *Oryctes rhinoceros* | Coconut rhinoceros beetle |
| *Paysandisia archon* | No common name, a palm borer |
| *Raoiella indica* | Red palm mite |
| *Rhabdoscelus obscurus* | New Guinea sugarcane weevil |
| *Rhynchophorus ferrugineus* | Red palm weevil |
| *Rhynchophorus palmarum* | South American palm weevil |

Pests within the scope of the present disclosure associated with solanaceous plants include the following.

| Scientific Name | Common Name |
| --- | --- |
| *Autographa gamma* | Silver-Y moth |
| Candidatus *Phytoplasma australiense* 16SrXII-B | Australian grapevine yellows |
| *Chrysodeixis chalcites* | Golden twin spot moth |
| *Globodera pallida* | Pale cyst nematode |
| *Globodera rostochiensis* | Golden nematode |
| *Helicoverpa armigera* | Old world bollworm |
| *Meloidogyne fallax* | False Columbia root-knot nematode |
| *Meloidogyne minor* | Root-knot nematode |
| *Neoleucinodes elegantalis* | Tomato fruit borer |
| *Ralstonia solanacearum* race 3 biovar 2 | Bacterial wilt/Southern bacterial Wilt |
| *Spodoptera littoralis* | Egyptian cottonworm |
| *Spodoptera litura* | Cotton cutworm |
| *Synchytrium endobioticum* | Potato wart |
| *Tecia solanivora* | Guatemalan potato tuber moth |
| *Thaumatotibia leucotreta* | False codling moth |
| *Tuta absoluta* | Tomato leaf miner |

Pests within the scope of the present disclosure associated with stone fruit include the following.

| Scientific Name | Common Name |
| --- | --- |
| *Adoxophyes orana* | Summer fruit tortrix |
| *Argyresthia pruniella* | Cherry blossom moth |
| *Bactrocera zonata* | Peach fruit fly |
| Candidatus *Phytoplasma prunorum* 16SrX-F | European stone fruit yellows |
| *Enarmonia formosana* | Cherry bark tortrix |
| *Epiphyas postvittana* | Light brown apple moth |
| *Grapholita funebrana* (Syn.: *Cydia funebrana*) | Plum fruit moth |
| *Leucoptera malifoliella* | Pear leaf blister moth |
| *Lobesia botrana* | European grape vine moth |
| *Monilia polystroma* | Asiatic brown rot |
| *Monilinia fructigena* | Brown rot, Apple brown rot |
| Potyvirus Plum Pox Virus | Plum pox |
| *Rhagoletis cerasi* | European cherry fruit fly |
| *Thaumatotibia leucotreta* | False codling moth |

Additional agricultural pests include the following cyst nematodes.

| Scientific Name | Common Name |
| --- | --- |
| *Globodera pallida* | Pale cyst nematode |
| *Globodera rostochiensis* | Golden nematode |
| *Heterodera cajani* | Pigeonpea cyst nematode |
| *Heterodera ciceri* | Chickpea cyst nematode |
| *Heterodera filipjevi* | Cereal cyst nematode |
| *Heterodera latipons* | Mediterranean cereal cyst nematode |
| *Heterodera sacchari* | Sugarcane cyst nematode |
| *Punctodera chalcoensis* | Mexican corn cyst nematode |

Additional agricultural pests include the following exotic wood borer or bark beetles.

| Scientific Name | Common Name |
| --- | --- |
| *Agrilus auroguttatus* | Goldspotted oak borer |
| *Agrilus biguttatus* | Oak splendour beetle |
| *Agrilus planipennis* | Emerald ash borer |
| *Anoplophora chinensis* | Citrus longhorned beetle |
| *Anoplophora glabripennis* | Asian longhorned beetle |
| *Chlorophorus annularis* | Bamboo borer |
| *Chlorophorus strobilicola* | Slender-banded pine cone longhorn beetle |
| *Dendroctonus micans* | Great spruce bark beetle |
| *Ips sexdentatus* | Six-toothed bark beetle |
| *Ips typographus* | European spruce bark beetle |

| Scientific Name | Common Name |
| --- | --- |
| *Megaplatypus mutatus* | No common name, an ambrosia beetle |
| *Monochamus alternatus* | Japanese pine sawyer |
| *Monochamus saltuarius* | Japanese pine sawyer |
| *Monochamus sutor* | Small white-marmorated longhorned beetle |
| *Orthotomicus erosus* | Mediterraneran pine engraver |
| *Pityogenes chalcographus* | Sixtoothed spruce bark beetle |
| *Platypus quercivorus* | Oak ambrosia beetle |
| *Scolytus intricatus* | European oak bark beetle |
| *Tetropium castaneum* | Black spruce beetle |
| *Tetropium fuscum* | Brown spruce longhorned beetle |
| *Tomicus destruens* | No common name, a pine shoot beetle |
| *Tomicus minor* | Lesser pine shoot beetle |
| *Tomicus piniperda* | Pine shoot beetle |
| *Trichoferus campestris* | Velvet longhorned beetle |
| *Trypodendron domesticum* | European hardwood ambrosia beetle Redbay ambrosia beetle |

Additional agricultural pests include the following mollusks.

| Scientific Name | Common Name |
| --- | --- |
| *Belocaulus* spp. | No common name, leatherleaf slugs |
| *Cernuella* spp. | No common name, hygromiid snails |
| *Cochlicella* spp. | No common name, cochlicellid snails |
| *Colosius* spp. | No common name, leatherleaf slugs |
| *Laevicaulis* spp. | No common name, leatherleaf slugs |
| *Lissachatina fulica* | Giant African snail |
| *Meghimatium pictum* | Chinese slug |
| *Monacha* spp. | No common name, hygromiid snails |
| *Sarasinula* spp. | No common name, leatherleaf slugs |
| *Semperula* spp. | No common name, leatherleaf slugs |
| *Veronicella* spp. | No common name, leatherleaf slugs |

Additional agricultural pests include the following moths.

| Scientific Name | Common Name |
| --- | --- |
| *Dendrolimus pini* | Pine-tree lappet |
| *Dendrolimus punctatus* | Masson pine moth |
| *Dendrolimus sibiricus* | Siberian silk moth |
| *Lymantria albescens* | Okinawa gypsy moth |
| *Lymantria dispar asiatica* | Asian gypsy moth |
| *Lymantria dispar japonica* | Japanese gypsy moth |
| *Lymantria mathura* | Rosy moth |
| *Lymantria monacha* | Nun moth |
| *Lymantria postalba* | White-winged gypsy moth |
| *Lymantria umbrosa* | Hokkaido gypsy moth |
| *Lymantria xylina* | Casuarina tussock moth |

It is to be understood that additional pests within the scope of the present disclosure may be identified by sources readily available to those of skill in the art.

Common pesticides in general within the scope of the present disclosure to which a pest may be resistant or develop resistance include the following: algicides, antifouling agents, antimicrobials, attractants, biopesticides, biocides, disinfectants, fungicides, fumigants, insecticides, miticides, microbial pesticides, molluscicides, nematicides, pheromones, repellants and rodenticides.

The following pesticide species are useful within the scope of the present disclosure: Glyphosate, Atrazine, Metam Sodium, Metolachlor-S, Acetochlor, Dichloropropene, 2,4-D, Methyl Bromide, Chloropicrin, Pendimenthalin, Ethephon, Chlorothalonil, Metam Potassium, Chlorpyrifos, Copper Hydroxide, Copper Sulfate, Simazine, Trifluralin, Propanil, Mancozeb, Aldicarb, Acephate, Diuron, MCPA, Paraquat, Dimethenamid, Carbaryl, MCPP, MSMA, Pyrethroids, Malathion, Dicamba, Pelarganoc Acid, Sulfuryl fluoride, Triclopyr, Paradiclorobenzene, Naphthalene, Chlorpyrifos, Naled, Dicrotophos, Phosmet, Phorate, Diazinon, Dimethoate, Azinphos-Methyl, and N,N-diethyl-meta-toluamide (insect repellant). One of skill in the art will readily be able to identify additional pesticide species using publicly available information of databases, for example the EPA list of registered pesticides available at world wide web site iaspub.epa.gov/apex/pesticides/f?p=chemicalsearch:1 and with reference to the most commonly used conventional pesticide active ingredients in the U.S. Agricultural, Home and Garden, Industry, Commercial, and Government Market Sectors as compiled by the EPA and publicly available at world wide website www.epa.gov/opp00001/pestsales/.

One of skill in the art will readily be able to identify pesticides toxic to particular pest species based on the present disclosure.

Accordingly, aspect of the present disclosure are directed to a method of altering a eukaryotic germline cell of an organism including introducing into the germline cell a first foreign nucleic acid sequence encoding an RNA guided DNA binding protein nuclease and one or more guide RNAs, and including corresponding promoter sequences and a first flanking sequence and a second flanking sequence, and including a sensitizing nucleic acid the expression of which is harmful to the organism when the organism is exposed to a chemical, compound or condition, wherein the one or more guide RNAs are complementary to one or more target locations on genomic DNA of a first chromosome and a second chromosome of a chromosome pair of the germline cell, wherein the nucleic acid sequence encoding the RNA guided DNA binding protein nuclease and the nucleic acid sequence encoding the one or more guide RNAs are between the first flanking sequence and the second flanking sequence, wherein the first flanking sequence includes a first sequence identical to a first portion of the target location on the first chromosome or the second chromosome of the genomic DNA, wherein the second flanking sequence includes a second sequence identical to a second portion of the target location on the first chromosome or the second chromosome of the genomic DNA, expressing the first foreign nucleic acid sequence to produce the RNA guided DNA binding protein nuclease and the one or more RNAs wherein the RNA guided DNA binding protein nuclease and an associated guide RNA co-localize to an associated target location on the first chromosome of the genomic DNA and the second chromosome of the genomic DNA and the RNA guided DNA binding protein nuclease cleaves the first chromosome of the genomic DNA at the target location in a cleavage site specific manner and cleaves the second chromosome of the genomic DNA at the target location in a cleavage site specific manner, inserting the first foreign nucleic acid sequence into the first chromosome of the chromosome pair of the genomic DNA at the cleavage site, and inserting the first foreign nucleic acid sequence into the second chromosome of the chromosome pair of the genomic DNA at the cleavage site to render the germline cell homozygous for the foreign nucleic acid sequence, and expressing the sensitizing nucleic acid rendering the resulting organism sensitive to the chemical, compound or condition such that the resulting organism perishes or is rendered sterile when exposed to the chemical, compound or condition.

According to one aspect, expression of the sensitizing nucleic acid increases toxicity of the chemical, compound or condition to the organism. According to one aspect, the germline cell is grown into an organism and the sensitizing nucleic acid is transferred to progeny to create a population of organisms including the sensitizing nucleic acid and where the sensitizing nucleic acid increases toxicity of the chemical, compound or condition to the organism. According to one aspect, the organism is a weed or pest. According to one aspect, the sensitizing nucleic acid is a sensitizing gene which replaces an existing gene. According to one aspect, the sensitizing gene is the exact or codon-altered ancestral version of an existing mutant gene in wild populations, such that the current mutated version is replaced with the ancestral form. According to one aspect, the existing gene has acquired a mutation contributing to resistance to a pesticide, herbicide, or fungicide. According to one aspect, the chemical or compound is a pesticide, herbicide or fungicide. According to one aspect, the pesticide, herbicide, or fungicide is one of: a Bt toxin produced by Cry1A.105, CryIAb, CryIF, Cry2Ab, Cry3Bb1, Cry34Ab1, Cry35Ab1, mCry3A, or VIP, 2,4-D or glyphosate. According to one aspect, the sensitizing gene replaces an existing gene whose function is required for the organism to survive or reproduce. According to one aspect, the chemical is a prodrug and the sensitizing gene encodes a corresponding prodrug-converting enzyme. According to one aspect, the enzyme/chemical pairing is cytosine deaminase/5-fluorocytosine, or nitroreductase/CB1954.

According to certain aspect of the present disclosure, a method of controlling a weed or pest population including a sensitivity gene drive in the genome of the weed or pest population wherein the sensitivity gene drive renders the weed or pest population vulnerable to toxicity when in the presence of a chemical, compound or condition is provided including contacting the weed or pest population with the chemical, compound or condition in an effective amount to kill the weed or pest, lower proliferation of the weed or pest or render the weed or pest sterile to inhibit proliferation. According to one aspect, the chemical or compound is an herbicide, or pesticide or fungicide.

According to certain aspect of the present disclosure, a method of altering a eukaryotic germline cell of an organism including a first sensitizing gene drive is provided including introducing into the germline cell a second foreign nucleic acid sequence encoding an RNA guided DNA binding protein nuclease and one or more guide RNAs, and including corresponding promoter sequences and a first flanking sequence and a second flanking sequence, and including a second sensitizing nucleic acid sequence the expression of which is harmful to the organism when the organism is exposed to a chemical, compound or condition, wherein the one or more guide RNAs are complementary to one or more target locations on genomic DNA of a first chromosome including the first sensitizing gene drive and a second chromosome of a chromosome pair of the germline cell including the first sensitizing gene drive, wherein the nucleic acid sequence encoding the RNA guided DNA binding protein nuclease and the nucleic acid sequence encoding the one or more guide RNAs of the second foreign nucleic acid sequence are between the first flanking sequence and the second flanking sequence, wherein the first flanking sequence includes a first sequence identical to a first portion of the target location on the first chromosome or the second chromosome of the genomic DNA, wherein the second flanking sequence includes a second sequence identical to a second portion of the target location on the first chromosome or the second chromosome of the genomic DNA, expressing the second foreign nucleic acid sequence to produce the RNA guided DNA binding protein nuclease and the one or more RNAs wherein the RNA guided DNA binding protein nuclease and an associated guide RNA co-localize to an associated target location on the first chromosome of the genomic DNA and the second chromosome of the genomic DNA and the RNA guided DNA binding protein nuclease cleaves the first chromosome of the genomic DNA at the target location in a cleavage site specific manner and cleaves the second chromosome of the genomic DNA at the target location in a cleavage site specific manner, wherein the first foreign nucleic acid sequence is removed, inserting the second foreign nucleic acid sequence into the first chromosome of the chromosome pair of the genomic DNA at the cleavage site, and inserting the second foreign nucleic acid sequence into the second chromosome of the chromosome pair of the genomic DNA at the cleavage site to render the germline cell homozygous for the second foreign nucleic acid sequence, and expressing the second sensitizing nucleic acid sequence rendering the resulting organism sensitive to the chemical, compound or condition such that the resulting organism perishes or is rendered sterile when exposed to the chemical, compound or condition. According to one aspect, the resulting organism is introduced into a wild type population such as that progeny of the resulting organism and a wild type organism includes the second sensitizing nucleic acid sequence. According to one aspect, the organism is a weed or pest.

According to certain aspect of the present disclosure, a method of altering a eukaryotic germline cell of an organism including a first sensitizing gene drive is provided including introducing into the germline cell a second foreign nucleic acid sequence encoding an RNA guided DNA binding protein nuclease and one or more guide RNAs, and including corresponding promoter sequences and a first flanking sequence and a second flanking sequence, and including a second sensitizing nucleic acid sequence the expression of which is harmful to the organism when the organism is exposed to a chemical, compound or condition, wherein the one or more guide RNAs are complementary to one or more target locations on genomic DNA of a first chromosome including the first sensitizing gene drive and a second chromosome of a chromosome pair of the germline cell including the first sensitizing gene drive, wherein the nucleic acid sequence encoding the RNA guided DNA binding protein nuclease and the nucleic acid sequence encoding the one or more guide RNAs of the second foreign nucleic acid sequence are between the first flanking sequence and the second flanking sequence, wherein the first flanking sequence includes a first sequence identical to a first portion of the target location on the first chromosome or the second chromosome of the genomic DNA, wherein the second flanking sequence includes a second sequence identical to a second portion of the target location on the first chromosome or the second chromosome of the genomic DNA, expressing the second foreign nucleic acid sequence to produce the RNA guided DNA binding protein nuclease and the one or more RNAs wherein the RNA guided DNA binding protein nuclease and an associated guide RNA co-localize to an associated target location on the first chromosome of the genomic DNA and the second chromosome of the genomic DNA and the RNA guided DNA binding protein nuclease cleaves the first chromosome of the genomic DNA at the target location in a cleavage site specific manner and cleaves the second chromosome of the genomic DNA at the target location in a cleavage site specific manner, inserting the second foreign nucleic acid sequence into the first chromosome of the chromosome pair of the genomic DNA at the cleavage site, and inserting the second foreign nucleic acid sequence into the second chromosome of the chromosome pair of the genomic DNA at the cleavage site to render the germline cell homozygous for the second foreign nucleic acid sequence, and expressing the second sensitizing nucleic acid sequence rendering the resulting organism sensitive to the chemical, compound or condition such that the resulting organism perishes or is rendered sterile when exposed to the chemical, compound or condition. According to certain aspects, the resulting organism is introduced into a wild type population such as that progeny of the resulting organism and a wild type organism includes the second sensitizing nucleic acid sequence. According to certain aspects, the organism is a weed or pest.

Example I

Plasmids and Genomic Cassettes

Gene drive cassettes were synthesized from gBlocks (Integrated DNA Technologies, Coralville, Iowa) and inserted into SK1 cells via. Cas9-mediated genome modification as follows. Guide RNAs for each drive were cloned into p416-Cas9 containing plasmids with expression driven by the SNR52 promoter. See DiCarlo, J. E. et al. Genome engineering in Saccharomyces cerevisiae using CRISPR-Cas systems, Nucleic Acids Res. 41, 4336-4343 (2013). 60 base pair homology arms to the target locus were added on both ends of the gene drive cassette via PCR and 5 ug of PCR product was co-transformed with the p416-Cas9-gRNA plasmids. Correctly integrated gene drives were verified by sequencing and p416-Cas9-gRNA plasmids were cured using 5-Fluoroorotic Acid (FDA) selection.

To create the URA3-containing ADE2 gene drive, the ADE2 gene drive w as cloned net to the *Candida albicans* UR43 gene in the pAG60 plasmid. The entire URA3 cassette and gene drive were PCR amplified and inserted using Cas9-mediated genome modification into the ADE2 locus of haploid SK1 cells.

The recoded C-terminus of the ABD1 gene and corresponding gene drive were synthesized as a gBlock to remove homology and generate mutations in the seed sequence via synonymous changes. The TER terminator was inserted at the 3' end of the recoded ABD1 gene between the gene and the gRNA as ABM shares a terminator with the MCI gene. The entire cassette was integrated into the haploid SK1 genome using Cas9-mediated genome modification.

The p416-Cas9-gRNA plasmid (conferring uracil prototrophy) is a variant of the previously described p414-Cas9-gRNA plasmid (conferring tryptophan prototrophy) (see DiCarlo, J. E. et al. Genome engineering in *Saccharomyces cerevisiae* using CRISPR-Cas systems, Nucleic Acids Res. 41, 4336-4343 (2013)) (Addgene #43802). One or the other was used in each mating experiment. The pRS413 vector was transformed into select cell types to confer histidine prototrophy as a marker to select for diploid cells. Strain genotypes are provided in Table 1 below.

TABLE 1

| Strain | Genotype |
| --- | --- |
| SK1 A | MATa ho::LYS2 lys2 ura3 leu2::hisG his3::hisG trp1::hisG |
| SK1 α | MATα ho::LYS2 lys2 ura3 leu2::hisG his3::hisG trp1::hisG |
| Y12A | MATa ho::HygMX ura3::KanMX |
| YPS128 | MATa ho::HygMX ura3::KanMX |
| YJM981 | MATa ho::HygMX ura3::KanMX |
| Y55 | MATa ho::HygMX ura3::KanMX |

TABLE 1-continued

| Strain | Genotype |
| --- | --- |
| UWOPS05-217.3 | MATa ho::HygMX ura3::KanMX |
| DBVPG 6044 | MATa ho::HygMX ura3::KanMX |
| 273614N | MATa ho::HygMX ura3::KanMX |

Example II

Yeast Mating Experiments

Haploid drive-containing SK1 yeast and haploid wild-type strains of the opposite mating type were mixed in equal amounts in YPAD liquid media and incubated overnight. The resulting diploids were washed in sterile water and plated on selective media for both parental genotypes. Table 2 below details the specific crosses.

TABLE 2

| MATa Genotype | MATα Genotype | Selection |
| --- | --- | --- |
| SK1 pRS414 - Cas9 | SK1 ade2::gRNA (gene drive), pRS413 | SC-histidine - tryptophan |
| SK1 ade2::gRNA + URA3 (gene drive), p414-Cas9 | SK1 pRS413 | SC-histidine - tryptophan |
| SK1 p414-Cas9 | SK1 abd1::ABD1 recoded + gRNA (gene drive), pRS413 | SC-histidine - tryptophan |
| Y12A Hygromycin B resistance (HygR) | SK1 ade2::gRNA (gene drive), p416-Cas9 | SC-uracil + 300 ug/mL Hygromycin B |
| YPS128 Hygromycin B resistance (HygR) | SK1 ade2::gRNA (gene drive), p416-Cas9 | SC-uracil + 300 ug/mL Hygromycin B |
| YJM981 Hygromycin B resistance (HygR) | SK1 ade2::gRNA (gene drive), p416-Cas9 | SC-uracil + 300 ug/mL Hygromycin B |
| Y55 Hygromycin B resistance (HygR) | SK1 ade2::gRNA (gene drive), p416-Cas9 | SC-uracil + 300 ug/mL Hygromycin B |
| UWOPS05-217.3 Hygromycin B resistance (HygR) | SK1 ade2::gRNA (gene drive), p416-Cas9 | SC-uracil + 300 ug/mL Hygromycin B |
| DBVPG 6044 Hygromycin B resistance (HygR) | SK1 ade2::gRNA (gene drive), p416-Cas9 | SC-uracil + 300 ug/mL Hygromycin B |
| 273614N Hygromycin B resistance (HygR) | SK1 ade2::gRNA (gene drive), p416-Cas9 | SC-uracil + 300 ug/mL Hygromycin B |
| SK1 ADE2::ADE2 silently recoded genomic target seed sequence, p414-Cas9 | SK1 ade2::gRNA (gene drive), pRS413 | SC-histidine - tryptophan |
| SK1, p414-empty | SK1 ade2::gRNA (gene drive), pRS413 | SC-histidine - tryptophan |

Example III

Sporulation and Tetrad Dissection

After mating in liquid YPAD and selection for diploids on selection plates, the selection plates were scraped into 10 mL selective media and grown overnight at 30° C. A fresh 5 mL YPAD culture was then inoculated to and OD=0.1 and grown 4-5 hours at 30° C. The entire culture was then washed twice in 10 mL water, inoculated into 2 mL of sporulation media (1% potassium acetate), and incubated at room-temperature for 3 days or until spores were visible. Sporulated cells were suspended in 50 μL of a stock solution of zymolyase (50 μg/mL in 1M sorbitol) and incubated at 30

C for 5 minutes, transferred to ice, diluted with 150 µL cold H₂O, microdissected using a Zeiss tetrad dissection microscope, and isolated spores grown on YPAD plates.

Example IV

Selection for URA3 Function

Dissected spores were grown in synthetic complete (SC) media and then spotted onto SC medium as well as SC medium without uracil. To enhance red color, all SC solid media used for plate images contained 0.5× adenine hemisulfate (final concentration of 0.08 mM).

Example V

Quantitative PCR

Candidate primer pairs were designed to amplify short regions specific to each drive or the wild-type sequence replaced by the drive, as well as the ACT1 gene as a control. All sequences are included in the supplementary information. Genomic DNA was extracted using Method A as described in Looke et al.31

KAPA SYBR FAST qPCR Master Mix (2×) was used to perform the qPCR reaction along with 25 ng of genomic DNA. The amplification efficiency and relative specificity of each primer pair were measured by amplifying dilutions of genomic DNA from wild-type and drive haploids, respectively, and the best-performing and well-matched pairs selected for use (see below for all primers used). Quantitative PCR reactions were performed on genomic DNA isolated from each parental haploid as well as from diploids arising from three independent mating events. Three reactions (technical replicates) were performed per sample on a LightCycler 96 machine by Roche.

Example VI

Calculations

Results from three technical replicates were averaged for calculations. In order to directly calculate the ratio of alleles before PCR amplification, the efficiencies of the different primer pairs were first determined. Efficiencies were calculated from qPCR runs of serial dilutions (6 orders of magnitude) as:

$$\text{Efficiency} = 10^{-1/slope}$$

$R^2$ values were higher than 0.99 in all cases except for one pair (ade2::URA3+sgRNA). The allelic ratios were calculated as:

$$x_a \cdot E_a^{Ct,a} = x_b \cdot x_b E_b^{Ct,b}$$

$$x_a/x_b = E_b^{Ct,b}/E_a^{Ct,a}$$

with $x_a$ and $x_b$ being the initial concentration of drive and wt DNA, $E_a$ and $E_b$ the efficiency of the respective primer pairs and Ct,a and Ct,b the Ct values for each sample.

Example VII

Efficiency of CRISPR/Cas9 Gene Drives in Yeast

To directly measure the efficiency of CRISPR/Cas9 gene drives in yeast, a system was developed using the red color that builds up in yeast lacking functional copies of the ADE2 gene. See Chamberlain, N., Cutts, N. S. & Rainbow, C. The formation of pigment and arylamine by yeasts. *J. Gen. Microbiol.* 7, 54-60 (1952). As depicted in FIG. 13A, if red ADE2⁻ haploids are mated with cream-colored wild-type haploids, the resulting heterozygous diploids inherit one functional copy and are therefore cream-colored. When these diploids undergo meiosis and reproduce via sporulation, half of the resulting haploids inherit the broken copy and are consequently red; the other half inherit the intact copy and are cream-colored (FIG. 13A).

As depicted in FIG. 13B, if the red haploids encode a functional gene drive that cuts and replaces the intact ADE2 locus inherited from the wild-type parent, their diploid progeny will be red. Because these red diploids will have two broken copies of ADE2, all of their sporulated haploid offspring will inherit a broken copy and consequently will also be red. Thus, the cutting efficiency of a gene drive that targets and replaces ADE2 can be assessed by simply plating diploids and counting the fraction that are red.

Figure 13C:
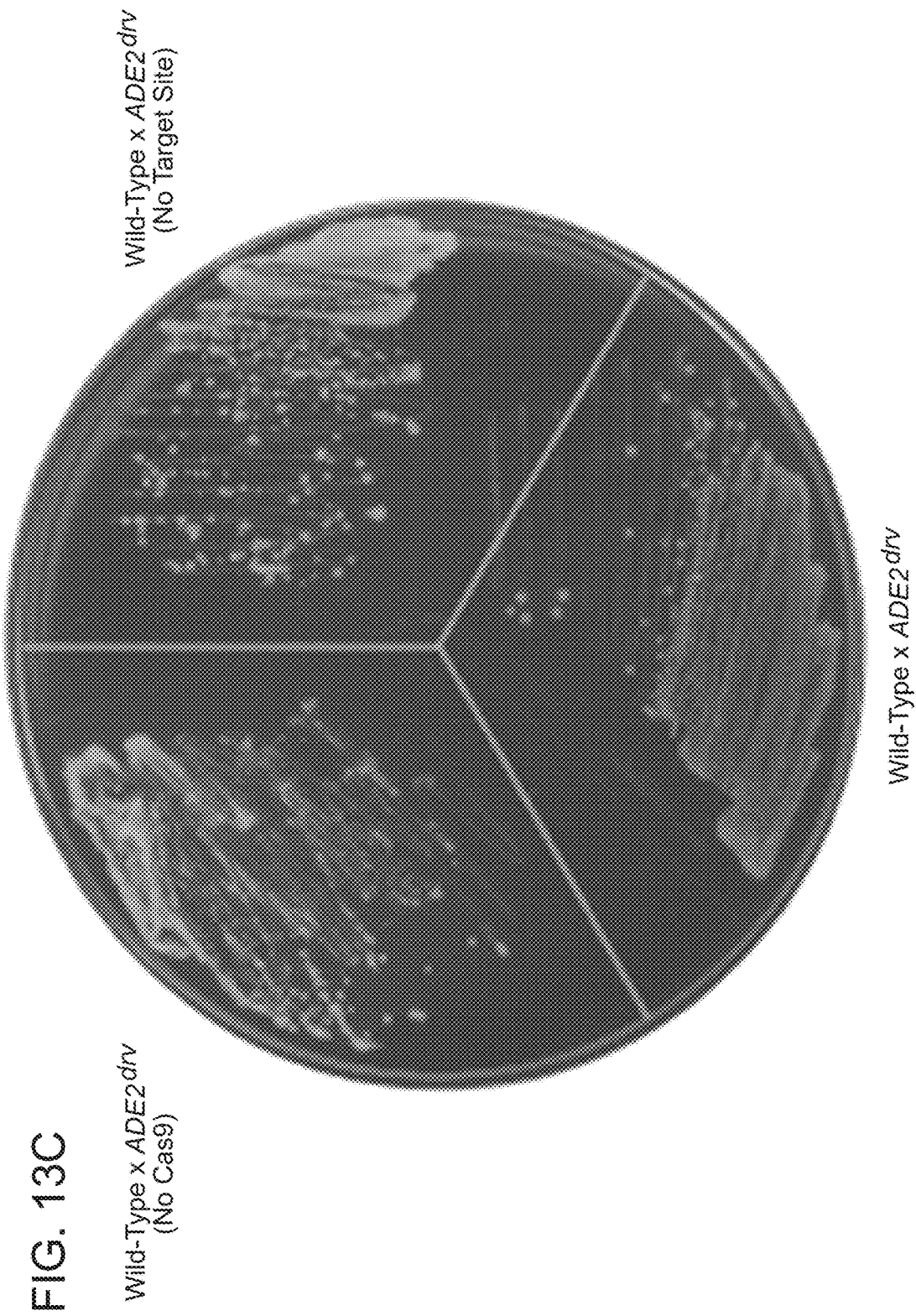
FIG. 13C is an image of *S. cerevisiae* colonies. Diploids produced by mating wild-type and ADE2::sgRNA gene drive haploids yield cream-colored colonies in the absence of Cas9 or when the target site is removed by recoding but uniformly red colonies when both are present, demonstrating Cas9-dependent disruption of the wild-type ADE2 copy.

A gene drive construct targeting ADE2 was made. To prevent accidental escape of the gene drive into the wild, Cas9 and guide RNAs were separated to avoid creating a self-sufficient inheritance-biasing cassette. Consequently, constructs encoded a guide RNA targeting ADE2, while Cas9 was provided from an episomal plasmid. Red haploids were mated to wild-type yeast of the opposite mating type in the presence or absence of the plasmid and plated on media that selects for diploids. As shown in FIG. 13C, nearly all colonies were red in the presence of the plasmid, indicating highly efficient cutting of the ADE2 copy inherited from the wild-type parent. In the absence of Cas9, no red diploid colonies were observed, demonstrating that the drive can only spread in laboratory yeast populations that provide it.

Figure 13D:
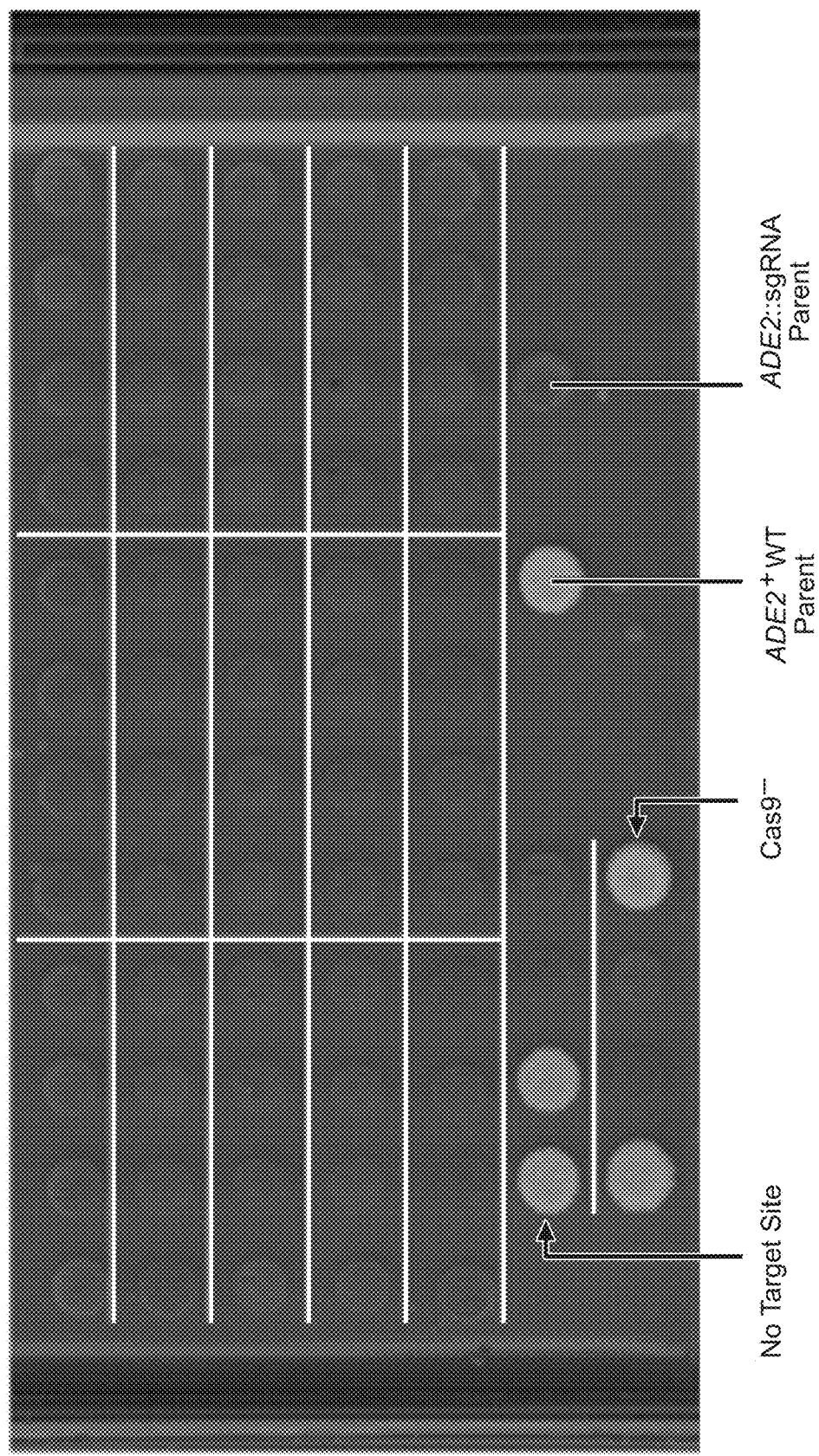
FIG. 13D are images of spores from 15 dissected tetrads that produce uniformly red colonies on adenine-limited plates, confirming disruption of the ADE2 gene inherited from the wild-type parent. In the absence of the target site or Cas9, normal 2:2 segregation is observed.

To verify that the ADE2 alleles from wild-type parents were lost, the mated diploids were sporulated and their resultant haploid progeny were examined. As shown in FIG. 13D, upon dissecting 18 cas9+ diploids, a perfect 4:0 ratio of red:cream haploids was observed, confirming that all copies of the ADE2 locus were disrupted. In contrast, 18 cream-colored cas9—diploids yielded a 2:2 red:cream ratio, indicating normal inheritance of the inactivated drive and the wild-type alleles.

To determine whether the ADE2 disruptions in red diploids were the result of successful copying of the drive element by homologous recombination, 72 haploids derived from dissected cas9+ diploids were sequenced. All sequenced colonies contained intact drives without additional mutations, indicating that drive mobilization was efficient and occurred at high fidelity.

Figure 14A:
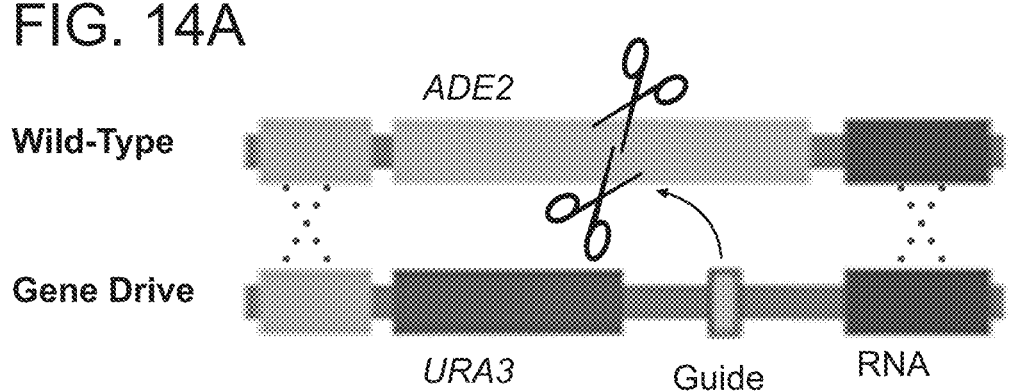
FIG. 14A is a schematic showing that the ADE2-targeting gene drive was modified to carry URA3 as a cargo gene.
Figure 14C:
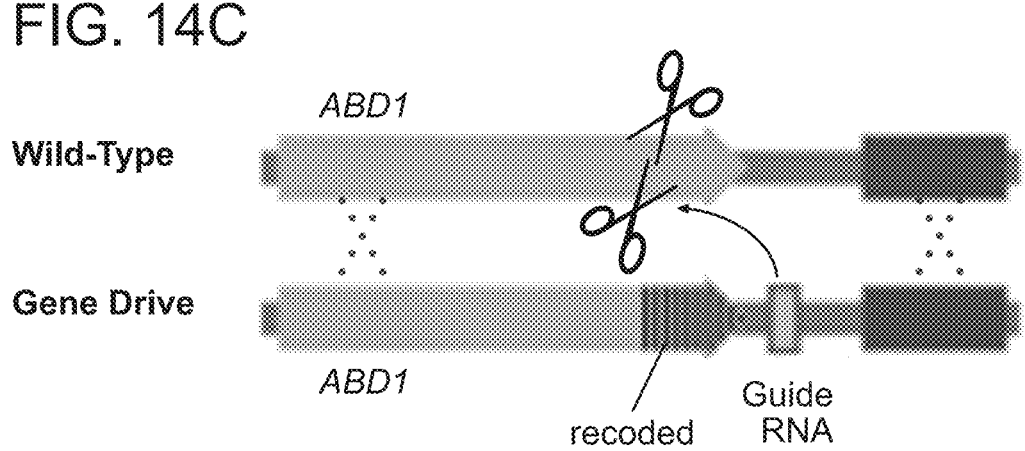
FIG. 14C is a schematic showing that the ABD1-targeting gene drive cuts and recodes the tail end of the essential ABD1 gene. Gene drives and cargo genes remain intact upon copying and can spread by targeting both non-essential and essential genes.
Figure 14B:
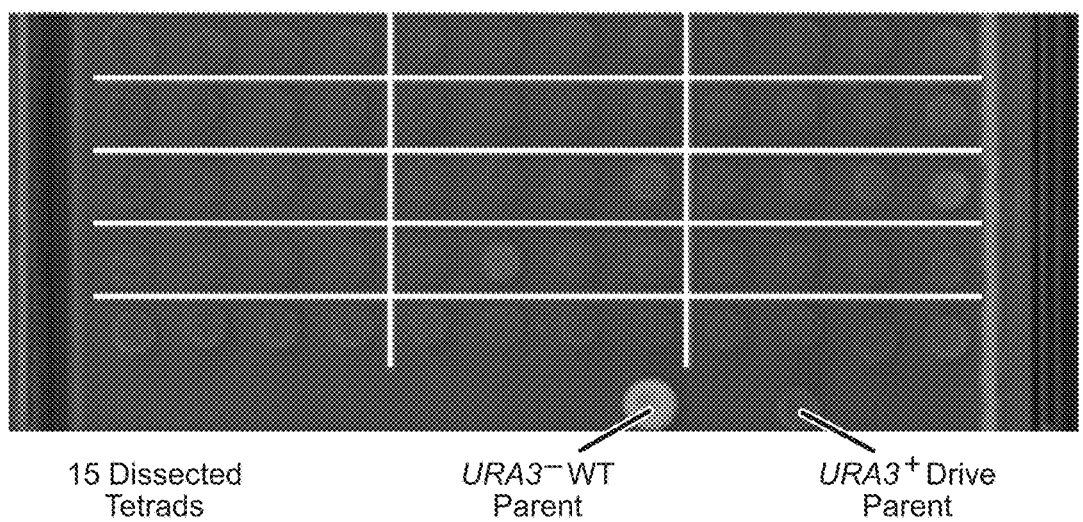
FIG. 14 B is an image of diploids produced by mating wild-type URA3⁻ haploid yeast with haploids encoding the gene drive carrying URA3 which were sporulated and tetrads dissected to isolate colonies arising from individual spores. All of these grew when replica-plated onto plates lacking uracil, demonstrating that the drive successfully copied URA3 in all diploids.
Figure 14B:
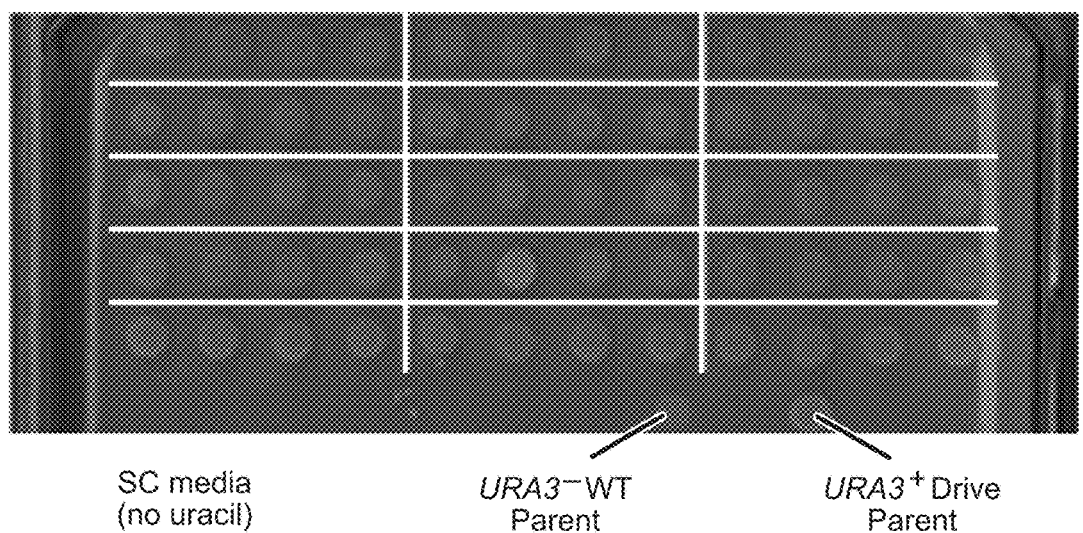

An ADE2 gene drive was modified as shown in schematic in FIG. 14A to contain an in cis URA3 allele, which allows laboratory modified yeast strains to grow in the absence of uracil supplementation. This drive element was tested for the ability of gene drives to "carry" an associated cargo element when copied into a target locus. URA3-containing drive haploids were mated with wild-type haploids in the presence of an episomal Cas9 plasmid, diploids were selected (all of which were red) and sporulated, and 18 tetrads were dissected. As was the case for the original ADE2 gene drive, all of the sporulated haploid cells formed red colonies. As shown in FIG. 14B, all grew normally when replica plated on uracil deficient media, indicating that the URA3 cargo element was efficiently copied with the drive.

Gene drives which target and recode an essential gene could avoid drive resistance in even large populations since error prone repair events that modify the target site will cause lethality. Non-essential but nonetheless important genes could similarly be edited because mutants created by NHEJ events would still be less fit than the drive itself. To test essential gene recoding during drive insertion, a third gene drive targeting ABD1 shown in schematic in FIG. 14C was constructed. See Mao, X., Schwer, B. & Shuman, S. Mutational analysis of the *Saccharomyces cerevisiae* ABD1 gene: cap methyltransferase activity is essential for cell growth, *Mol. Cell. Biol.* 16, 475-480 (1996).

A haploid strain containing a recoded ABD1 allele upstream of a guide RNA targeting the natural ABD1 coding sequence was mated to wild-type cells in the presence of Cas9. Diploid cells were selected of which 18 were sporulated 18 of them. 72 segregants were sequenced. All contained the recoded ABD1 locus and the guide RNAs, thereby demonstrating gene drives based on essential gene recoding.

Figure 15B:
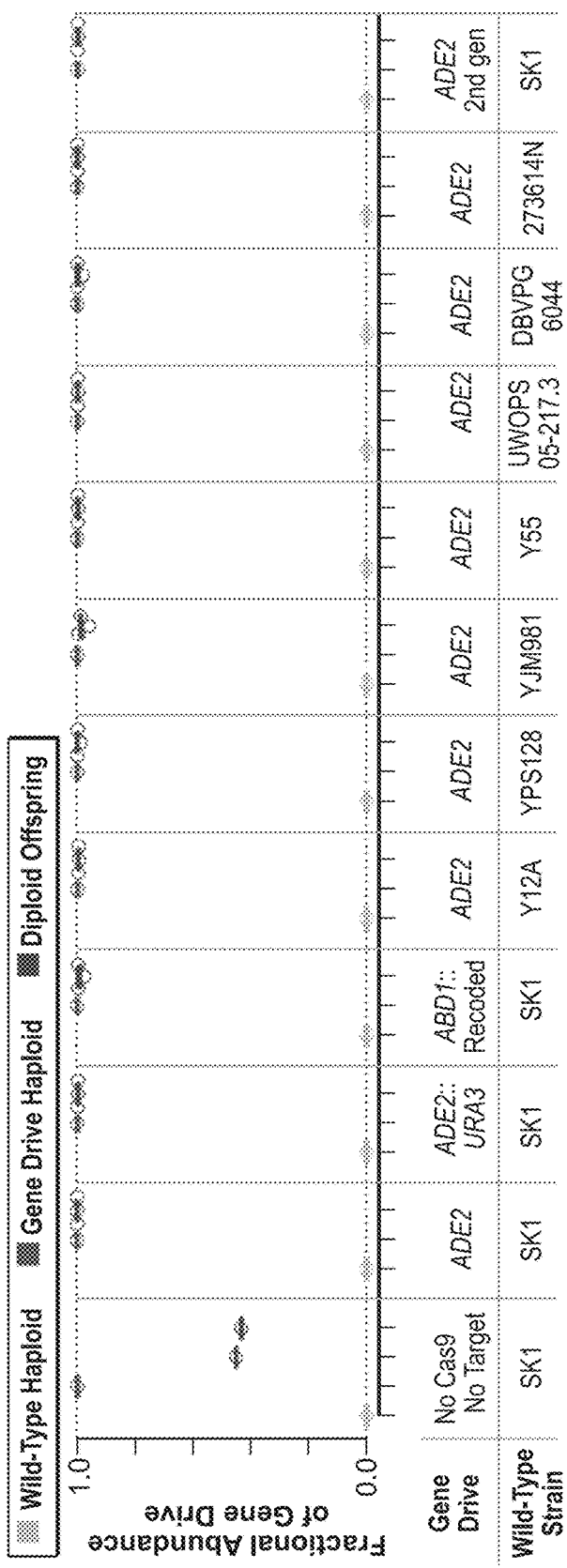
FIG. 15B depicts quantitative PCR results of the extent of inheritance-biasing in diverse yeast strains depicting the relative abundance of wild-type and drive-containing alleles in diploids arising from matings between SK1 haploids bearing gene drives and diverse wild-type haploid strains. "No Cas9" and "No Target" refer to the haploid cells containing the ADE2 drive element mated to wild-type haploids in the absence of Cas9 or to a wild-type strain with a mutation in the targeted sequence that prevents cutting. "2nd gen" refers to the haploid progeny of an earlier mating.

Gene drives were copied from a laboratory strain into a diverse group of native *S. cerevisiae* strains. ADE2 drive-containing haploids were mated with 6 phylogenetically and phenotypically diverse wild-type strains of haploid *S. cerevisiae*. See Liti, G. et al. Population genomics of domestic and wild yeasts, *Nature* 458, 337-341 (2009). See also FIG. 15A. To quantitatively measure the efficiency of gene drive copying for each cross, quantitative PCR was performed on populations of all diploids using one set of primers specific to the drive and another set designed to amplify either wild-type or NHEJ-disrupted alleles. As shown In FIG. 15B which was generated using BoxPlot (see Spitzer, M., Wildenhain, J., Rappsilber, J. & Tyers, M. BoxPlotR: a web tool for generation of box plots. *Nat. Methods* 11, 121-122 (2014)), the fraction of diploid chromosomes containing the ADE2 gene drive was over 99% regardless of wild-type parent, demonstrating the use of the drive in diverse backgrounds. Addition of the URA3 cargo gene did not appreciably change this efficiency. The ABD1 drive was copied at an equivalent rate.

The stability of the drive over successive copying events was investigated. As shown in FIG. 15B, several haploid offspring of the first-round ADE2 gene drive diploids were mated to wild-type haploids containing the Cas9-expressing plasmid. All of the second-generation gene drive constructs biased inheritance at the same efficiency, demonstrating a continued ability to spread through sexually reproducing populations over generations.

The following genome modification primer and gBlock sequences are provided.

| | Sequence |
|---|---|
| Genome modification primers and gBlocks | |
| ADE2.sgRNA.ade2.1 insert.F | TACGAACCGGGTAATACTAAGTGATTGACTCTTGCTGACCT<br>TTTATTAAGAACTAAATGGtctttgaaaagataatgtatgattatgctttc |
| ADE2.sgRNA.ade2.1 insert.R | TAATAAGTGATCTTATGTATGAAATTCTTAAAAAAGGACACC<br>TGTAAGCGTTGATTTCTAagacataaaaaaacaaaaaaagcaccac |
| gRNA + CaURA3.ade2.F | TACGAACCGGGTAATACTAAGTGATTGACTCTTGCTGACCT<br>TTTATTAAGAACTAAATGGagacataaaaaaacaaaaaaagcaccaccg |
| gRNA + CaURA3.ade2.R | TAATAAGTGATCTTATGTATGAAATTCTTAAAAAAGGACACC<br>TGTAAGCGTTGATTTCTAtcgacactggatggcggcgttagtatc |
| ABD1.recode + gRNA | AGCCAGATGCCATTCAACAAGTTCTTCGTGCAGGAGATACC<br>AAAGTGGATAGAACGTTTCAGCCCAAAGATGCGTGAGGGG<br>CTTCAGCGTAGCGACGGGCGTTACGGGGTGGAGGGTGACG<br>AGAAAGAGGCTGCTAGCTACTTTTACACGATGTTCGCTTTT<br>AGAAAAGTTAAGCAATACATAGAGCCTGAGTCAGTTAAACC<br>AAATTGAACGGCTCCTCGCTGCAGACCTGCGAGCAGGGAA<br>ACGCTCCCCTCACAGACGCGTTGAATTGTCCCCACGCCGCG<br>CCCCTGTAGAGAAATATAAAAGGTTAGGATTTGCCACTGAG<br>GTTCTTCTTTCATATACTTCCTTTTAAAATCTTGCTAGGATAC<br>AGTTCTCACATCACATCCGAACATAAACAACCATGGGTATG<br>ACCGACCAAGCGACGCCCAACCTGCCATCACGAGATTTCG<br>ATCCCACCGCCGCCTTCTATGAAAGGtctttgaaaagataatgtatgattat<br>gctttcactcatatttatacagaaacttgatgttttctttcgagtatatacaaggtgattacatgtacgttt<br>gaagtacaactctagattttgtagtgccctcttgggctagcggtaaaggtgcgcatttttttcacaccc<br>tacaatgttctgttcaaaagatttttggtcaaacgctgtagaagtgaaagttggtgcgcatgtttcggc<br>gttcgaaacttctccgcagtgaaagataaatgatcTGAAGGGGATGAAAAGGA<br>AGGTTTTAGAGCTAGAAATAGCAAGTTAAAATAAGGCTAGT<br>CCGTTATCAACTTGAAAAAGTGGCACCGAGTCGGTGGTGC<br>TTTTTTTGTTTTTTATGTCT |
| ABD1.recode + gRNA.int.F | tatgttgtgccattcgaaaccttaagaagtttggctgatgaatacggtttggaactagtaAGCCA<br>GATGCCATTCAACAAGTTC |
| ABD1.recode + gRNA.int.R | gtaatacggccgaaatacagatgctttatagtagggttattgtttctattcattttttattAGACATA<br>AAAAACAAAAAAGCACCACC |
| ADE2.gRNA | tctttgaaaagataatgtatgattatgctttcactcatatttatacagaaacttgatgttttctttcgagtat<br>atacaaggtgattacatgtacgtttgaagtacaactctagattttgtagtgccctcttgggctagcggt<br>aaaggtgcgcatttttttcacaccctacaatgttctgttcaaaagatttttggtcaaacgctgtagaagtg<br>aaagttggtgcgcatgtttcggcgttcgaaacttctccgcagtgaaagataaatgatcACTTG<br>AAGATTCTTTAGTGTGTTTTAGAGCTAGAAATAGCAAGTTA<br>AAATAAGGCTAGTCCGTTATCAACTTGAAAAAGTGGCACCG<br>AGTCGGTGGTGCTTTTTTTGTTTTTTATGTCT |

|                              | Sequence                                                                                          |
| ---------------------------- | ------------------------------------------------------------------------------------------------- |
| ADE2.1.silent. seed.90mer.F  | TGATGTGCTAACGATTGAGATTGAGCATGTTGATGTTCCTAC CCTGAAAAACCTGCAAGTAAAACATCCCAAATTAAAAATTT ACCCTTC       |
| ADE2.1.silent. seed.90mer.F  | GAAGGGTAAATTTTTAATTTGGGATGTTTTACTTGCAGGTTT TTCAGGGTAGGAACATCAACATGCTCAATCTCAATCGTTAG CACATCA       |
| ABD1.ver.F                   | ATAGATAATGTTCCTGAATATGTTGTGCCA                                                                    |
| ABD1.ver.R                   | TTACTACATATAGAAGTCTTGTAATACGGCCG                                                                  |
| ADE2.ver.F                   | GCTACGAACCGGGTAATACTAAGTGATTG                                                                     |
| ADE2.ver.R                   | CAGGTAATTATTCCTTGCTTCTTGTTACTGG                                                                   |
| qPCR Primers                 |                                                                                                   |
| ade2.WT.qPCR.F               | TACGAACCGGGTAATACTAAGTGATTGACTC                                                                   |
| ade2.gRNA.qPCR.R             | CGCTAGCCCAAGAGGGCACTACA                                                                           |
| ade2.WT.qPCR.R               | TACCAACTGTTCTAGAATCCATACTTGATTGTTT                                                                |
| URA3.genedrive. ade2.WT.qPCR.F | TACGAACCGGGTAATACTAAGTGATTGACTC                                                                  |
| URA3.genedrive. ade2.WT.qPCR.R | CCTCCTAATATACCAACTGTTCTAGAATCCAT                                                                 |
| URA3.genedrive. ade2.gRNA.qPCR.R | AAACTTCTCCGCAGTGAAAGATAAATGATC                                                                 |
| ABD1_rec_qPCR.R              | CGAGGAGCCGTTCAATTTGGTTTAACTGAC                                                                    |
| ABD1_rec_qPCR.F              | AGATGCGTGAGGGGCTTCAGC                                                                             |
| ABD1_WT_qPCR (JDwt1.4).F     | GAAGGGGATGAAAAGGAAGC                                                                              |
| ABD1_WT_qPCR (JDwt1.3).R     | CGCTTTCCGGTTCGATATAC                                                                              |
| ACT1.qPCR.F                  | CGAAAGATTCAGAGCCCCAGAAGCT                                                                         |
| ACT1.qPCR.R                  | CGGTGATTTCCTTTTGCATTCTTTCG                                                                        |

The invention claimed is:

1. A method of altering a eukaryotic germline cell derived from an organism to include a CRISPR/Cas-based gene drive comprising
    introducing into the germline cell the CRISPR/Cas-based gene drive comprising a first foreign nucleic acid sequence comprising sequences encoding a Cas9 and one or more guide RNAs between a first flanking sequence and a second flanking sequence,
    wherein the one or more guide RNAs are complementary to one or more target locations on genomic DNA of a first chromosome and a second chromosome of a chromosome pair of the germline cell,
    wherein the first flanking sequence includes a first sequence identical to a first location sequence on the first chromosome or the second chromosome of the genomic DNA,
    wherein the second flanking sequence includes a second sequence identical to a second location sequence on the first chromosome or the second chromosome of the genomic DNA,
    wherein the one or more target locations are flanked by the first and second location sequences on the first chromosome or the second chromosome of the genomic DNA,
    expressing the first foreign nucleic acid sequence to produce the Cas9 and the one or more guide RNAs wherein the Cas9 and an associated guide RNA co-localize to one or more complementary target locations on the first chromosome of the genomic DNA and the second chromosome of the genomic DNA and the Cas9 cleaves the first chromosome of the genomic DNA at the one or more complementary target locations in a cleavage site specific manner and cleaves the second chromosome of the genomic DNA at the one or more complementary target locations in a cleavage site specific manner,
    inserting the first foreign nucleic acid sequence into the first chromosome of the chromosome pair of the genomic DNA at the cleavage site, and inserting the first foreign nucleic acid sequence into the second chromosome of the chromosome pair of the genomic DNA at the cleavage site to render the germline cell homozygous for the foreign nucleic acid sequence, and
    developing an organism from the germline cell altered by the first foreign nucleic acid
    wherein the germline cell is a fungal cell, a plant cell, an insect cell or a non-human mammalian cell,
    wherein the one or more guide RNAs are about 100 nucleotides and are composed of a first region of about 20 nucleotides as a region of complementarity to a target sequence and a second region of about 80 nucleotides.

2. The method of claim 1 wherein the Cas9 creates a double stranded break or a single stranded break.

3. The method of claim 1
    further comprising introducing into a germline cell derived from the organism developed from the germline cell altered by the first foreign nucleic acid a second foreign nucleic acid sequence comprising sequences encoding a Cas9 and one or more guide RNAs, a first flanking sequence and a second flanking sequence,
    wherein the one or more guide RNAs encoded by the second foreign nucleic acid sequence are complementary to one or more target locations within the first foreign nucleic acid sequence,
    expressing the second foreign nucleic acid sequence to produce the RNA guided DNA binding protein nuclease and the one or more RNAs wherein the RNA guided DNA binding protein nuclease and an associated guide RNA co-localize to one or more complementary target locations on the chromosome of the genomic DNA and the RNA guided DNA binding protein nuclease cleaves the chromosome of the genomic DNA at the one or more complementary target locations in a cleavage site specific manner to remove the first foreign nucleic acid sequence, and
    inserting the second foreign nucleic acid sequence into the chromosome of the genomic DNA at the cleavage site.

4. The method of claim 1 wherein the Cas9 encoded by the first and second foreign nucleic acid is Cas9 nickase.

5. The method of claim 1 wherein at least one target location is within an essential gene and the first foreign nucleic acid sequence is inserted adjacent to and replacing part of the essential gene.

6. The method of claim 1 wherein the first foreign nucleic acid sequence is inserted by homologous recombination.

7. The method of claim 3 wherein the one or more guide RNAs encoded by the first and second foreign nucleic acid are between about 10 to about 250 nucleotides.

8. The method of claim 3 wherein the Cas9 encoded by the first and second foreign nucleic acid co-localizes with an associated guide RNA at a plurality of complementary target locations to cleave the first chromosome and/or the second chromosome at a plurality of cleavage sites.

9. The method of claim 8 wherein cleaving at the plurality of cleavage sites removes a DNA sequence which is replaced with the first and/or the second foreign nucleic acid sequence by homologous recombination.

10. The method of claim 3 wherein the second foreign nucleic acid sequence includes genetic modifications different from the first foreign nucleic acid sequence.

11. The method of claim 3 further comprising developing an organism from the germline cell altered by the second foreign nucleic acid, and introducing into a germline cell derived from the organism developed from the germline cell altered by the second foreign nucleic acid a third foreign nucleic acid sequence comprising sequences encoding a Cas9 and one or more guide RNAs, a first flanking sequence and a second flanking sequence,
wherein the one or more guide RNAs encoded by the third foreign nucleic acid sequence are complementary to the one or more target locations that were altered by the second foreign nucleic acid sequence,
expressing the third foreign nucleic acid sequence to produce the Cas9 and the one or more RNAs wherein the Cas9 and an associated guide RNA co-localize to one or more complementary target locations on the chromosome of the genomic DNA and the Cas9 cleaves the chromosome of the genomic DNA at the one or more complementary target locations in a cleavage site specific manner to remove the second foreign nucleic acid sequence, and
inserting the third foreign nucleic acid sequence into the chromosome of the genomic DNA at the cleavage site, wherein the third foreign nucleic acid sequence includes the wild type sequence of the chromosome that was modified by the first foreign nucleic acid sequence.

12. A method of altering a eukaryotic germline cell derived from an organism to include a CRISPR/Cas-based gene drive and wherein the germline cell is altered at a plurality of genes comprising
introducing into the germline cell the CRISPR/Cas-based gene drive comprising a first foreign nucleic acid sequence comprising sequences encoding a Cas9 and a plurality of guide RNAs between a first flanking sequence and a second flanking sequence, along with one or more additional foreign nucleic acid sequences corresponding to the plurality of genes,
wherein the plurality of guide RNAs include one or more gene specific guide RNAs that are complementary to one or more target locations on a plurality of genes in the genomic DNA of a chromosome of the germline cell,
wherein the first flanking sequence includes a first sequence identical to a first location sequence on the chromosome of the genomic DNA,
wherein the second flanking sequence includes a second sequence identical to a second location sequence on the chromosome of the genomic DNA,
wherein the one or more target locations on each of the plurality of genes are flanked by gene specific first and second location sequences on the chromosome of the genomic DNA,
wherein each of the one or more additional foreign nucleic acid sequences contains a gene specific first flanking sequence and a gene specific second flanking sequence homologous to the gene specific first and second location sequences of the target locations on the plurality of genes,
expressing the first foreign nucleic acid sequence to produce the Cas9 and the plurality of guide RNAs wherein the Cas9 and associated guide RNAs co-localize to a plurality of complementary target locations on the chromosome of the genomic DNA and the Cas9 cleaves the chromosome of the genomic DNA at a plurality of genes in a cleavage site specific manner,
inserting the corresponding foreign nucleic acid sequences into the chromosome of the genomic DNA at each cleavage site,
wherein the one or more gene specific guide RNAs are about 100 nucleotides and are composed of a first region of about 20 nucleotides as a region of complementarity to a target sequence and a second region of about 80 nucleotides.

13. The method of claim 12 further comprising developing an organism from the germline cell altered by the first foreign nucleic acid, and introducing into a germline cell derived from the organism developed from the germline cell altered by the first foreign nucleic acid sequence a second foreign nucleic acid sequence comprising sequences encoding a Cas9 and a plurality of guide RNAs, and a first flanking sequence and a second flanking sequence, along with one or more additional foreign nucleic acid sequences corresponding to the plurality of genes altered by the first nucleic acid sequence,
wherein the plurality of guide RNAs are complementary to the plurality of target locations that were altered by the first foreign nucleic acid sequence,
expressing the second foreign nucleic acid sequence to produce the Cas9 and the plurality of guide RNAs wherein the Cas9 and associated guide RNAs co-localize to complementary target locations that were altered by the first foreign nucleic acid sequence on the chromosome of the genomic DNA and the Cas9 cleaves the chromosome of the genomic DNA at the complementary target locations in a cleavage site specific manner, and
inserting the second foreign nucleic acid sequence and the one or more additional foreign nucleic acid sequences into the chromosome of the genomic DNA at each cleavage site as determined by the first and second flanking sequences of each foreign nucleic acid sequence that are homologous to the first and second gene specific location sequences flanking each cleavage site.

14. A method of altering a eukaryotic germline cell derived from an organism to include a CRISPR/Cas-based gene drive comprising
introducing into the germline cell the CRISPR/Cas-based gene drive comprising a first foreign nucleic acid sequence comprising sequences encoding a Cas9, a plurality of guide RNAs, and a nucleic acid encoding an enzyme capable of converting a prodrug into a chemical that is toxic to the organism between a first flanking sequence and a second flanking sequence,
wherein the plurality of guide RNAs are complementary to a plurality of target locations on genomic DNA of a first chromosome and a second chromosome of a chromosome pair of the germline cell,
wherein the first flanking sequence includes a first sequence identical to a first location sequence on the first chromosome or the second chromosome of the genomic DNA,
wherein the second flanking sequence includes a second sequence identical to a second location sequence on the first chromosome or the second chromosome of the genomic DNA,
wherein the plurality of target locations are flanked by the first and second location sequences on the first chromosome or the second chromosome of the genomic DNA,
expressing the first foreign nucleic acid sequence to produce the Cas9 and the plurality of guide RNAs wherein the Cas9 and an associated guide RNA co-localize to a plurality of complementary target locations on the first chromosome of the genomic DNA and the second chromosome of the genomic DNA and the Cas9 cleaves the first chromosome of the genomic DNA at the plurality of complementary target locations in a cleavage site specific manner and cleaves the second chromosome of the genomic DNA at the plurality of target locations in a cleavage site specific manner, inserting the first foreign nucleic acid sequence into the first chromosome of the chromosome pair of the genomic DNA at the cleavage site, and inserting the first foreign nucleic acid sequence into the second chromosome of the chromosome pair of the genomic DNA at the cleavage site to render the germline cell homozygous for the foreign nucleic acid sequence, and expressing the nucleic acid encoding the enzyme rendering the organism sensitive to the chemical such that the chemical is toxic to the organism, wherein each of the plurality of guide RNAs are about 100 nucleotides and are composed of a first region of about 20 nucleotides as a region of complementarity to a target sequence and a second region of about 80 nucleotides.

15. The method of claim 14 wherein the germline cell is grown into an organism and the nucleic acid encoding the enzyme is transferred to progeny to create a population of organisms including the nucleic acid encoding the enzyme and where the nucleic acid encoding the enzyme increases toxicity of the chemical to the organism.

16. The method of claim 14 wherein the organism is a weed or pest.

17. The method of claim 14 wherein the chemical is a pesticide, herbicide or fungicide.

18. The method of claim 17, where the pesticide is one of a Bt toxin produced by Cry1A.105, CryIAb, CryIF, Cry2Ab, Cry3Bb 1, Cry34Ab 1, Cry35Ab1, mCry3A, wherein the herbicide is 2,4-dichlorophenoxyacetic acid or glyphosate, and wherein the fungicide is a combination of Mefenoxam, Thiabendazole, Sedaxane, Thiamethoxam and Fludioxinil.

19. The method of claim 14 where the enzyme/chemical pairing is cytosine deaminase/5-fluorocytosine, or nitroreductase/CB1954.

20. A method of altering a eukaryotic germline cell derived from an organism including a first CRISPR/Cas9 based gene drive comprising introducing into the germline cell a second CRISPR/Cas9 based gene drive comprising a second foreign nucleic acid sequence comprising sequences encoding a Cas9, a plurality of guide RNAs, and a second nucleic acid encoding an enzyme capable of converting a prodrug into a chemical that is toxic to the organism between a first flanking sequence and a second flanking sequence, wherein the plurality of guide RNAs are complementary to a plurality of target locations on genomic DNA of a first chromosome including the first sensitizing gene drive and a second chromosome of a chromosome pair of the germline cell including the first sensitizing gene drive, wherein the first flanking sequence includes a first sequence identical to a first location sequence on the first chromosome or the second chromosome of the genomic DNA, wherein the second flanking sequence includes a second sequence identical to a second location sequence on the first chromosome or the second chromosome of the genomic DNA, wherein the plurality of target locations are flanked by the first and second location sequences on the first chromosome or the second chromosome of the genomic DNA, expressing the second foreign nucleic acid sequence to produce Cas9 and the plurality of guide RNAs wherein the Cas9 and an associated guide RNA co-localize to a plurality of complementary target locations on the first chromosome of the genomic DNA and the second chromosome of the genomic DNA and the Cas9 cleaves the first chromosome of the genomic DNA at the plurality of complementary target locations in a cleavage site specific manner and cleaves the second chromosome of the genomic DNA at the plurality of complementary target locations in a cleavage site specific manner, inserting the second foreign nucleic acid sequence into the first chromosome of the chromosome pair of the genomic DNA at the cleavage site, and inserting the second foreign nucleic acid sequence into the second chromosome of the chromosome pair of the genomic DNA at the cleavage site to render the germline cell homozygous for the second foreign nucleic acid sequence, and expressing the second nucleic acid encoding the enzyme rendering the organism sensitive to the chemical such that the chemical is toxic to the organism, wherein each of the plurality of guide RNAs are about 100 nucleotides and are composed of a first region of about 20 nucleotides as a region of complementarity to a target sequence and a second region of about 80 nucleotides.

21. The method of claim 20 wherein the organism is introduced into a wild type population such as that progeny of the organism and a wild type organism includes the second sensitizing nucleic acid encoding the enzyme.

22. The method of claim 20 wherein the organism is a weed.

23. The method of claim 20 wherein the organism is a pest.

24. The method of claim 1 wherein the organism is a weed.

25. The method of claim 14 wherein the organism is a weed.

* * * * *

SEQUENCE LISTING

<160> NUMBER OF SEQ ID NOS: 28

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495
```

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr

-continued

```
              915                 920                 925
Lys His Val Ala Gln Ile Leu Asp Ser Arg Met Asn Thr Lys Tyr Asp
              930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
              965                 970                 975

Glu Ile Asn Asn Tyr His His Ala His Asp Ala Tyr Leu Asn Ala Val
              980                 985                 990

Val Gly Thr Ala Leu Ile Lys Lys Tyr Pro Lys Leu Glu Ser Glu Phe
              995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320
```

```
Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

<210> SEQ ID NO 2
<211> LENGTH: 92
<212> TYPE: DNA
<213> ORGANISM: Artificial
<220> FEATURE:
<223> OTHER INFORMATION: Genome modification primers and gBlocks
      ADE2.sgRNA.ade2.1 insert.F

<400> SEQUENCE: 2
tacgaaccgg gtaatactaa gtgattgact cttgctgacc ttttattaag aactaaatgg    60
tctttgaaaa gataatgtat gattatgctt tc                                  92

<210> SEQ ID NO 3
<211> LENGTH: 87
<212> TYPE: DNA
<213> ORGANISM: Artificial
<220> FEATURE:
<223> OTHER INFORMATION: Genome modification primers and gBlocks
      ADE2.sgRNA.ade2.1 insert.R

<400> SEQUENCE: 3
taataagtga tcttatgtat gaaattctta aaaaggaca cctgtaagcg ttgatttcta     60
agacataaaa aacaaaaaaa gcaccac                                        87

<210> SEQ ID NO 4
<211> LENGTH: 89
<212> TYPE: DNA
<213> ORGANISM: Artificial
<220> FEATURE:
<223> OTHER INFORMATION: Genome modification primers and gBlocks
      gRNA+CaURA3.ade2.F

<400> SEQUENCE: 4
tacgaaccgg gtaatactaa gtgattgact cttgctgacc ttttattaag aactaaatgg    60
agacataaaa aacaaaaaaa gcaccaccg                                      89

<210> SEQ ID NO 5
<211> LENGTH: 87
<212> TYPE: DNA
<213> ORGANISM: Artificial
<220> FEATURE:
<223> OTHER INFORMATION: Genome modification primers and gBlocks
      gRNA+CaURA3.ade2.R

<400> SEQUENCE: 5
taataagtga tcttatgtat gaaattctta aaaaggaca cctgtaagcg ttgatttcta     60
tcgacactgg atggcggcgt tagtatc                                        87

<210> SEQ ID NO 6
<211> LENGTH: 863
<212> TYPE: DNA
<213> ORGANISM: Artificial
<220> FEATURE:
<223> OTHER INFORMATION: Genome modification primers and gBlocks
      ABD1.recode+gRNA
```

<400> SEQUENCE: 6

```
agccagatgc cattcaacaa gttcttcgtg caggagatac caaagtggat agaacgtttc    60
agcccaaaga tgcgtgaggg gcttcagcgt agcgacgggc gttacggggt ggagggtgac   120
gagaaagagg ctgctagcta cttttacacg atgttcgctt ttagaaaagt taagcaatac   180
atagagcctg agtcagttaa accaaattga acggctcctc gctgcagacc tgcgagcagg   240
gaaacgctcc cctcacagac gcgttgaatt gtccccacgc cgcgcccctg tagagaaata   300
taaaaggtta ggatttgcca ctgaggttct tctttcatat acttccttttt aaaatcttgc   360
taggatacag ttctcacatc acatccgaac ataaacaacc atgggtatga ccgaccaagc   420
gacgcccaac ctgccatcac gagatttcga tcccaccgcc gccttctatg aaaggtcttt   480
gaaaagataa tgtatgatta tgctttcact catatttata cagaaacttg atgttttctt   540
tcgagtatat acaaggtgat tacatgtacg tttgaagtac aactctagat tttgtagtgc   600
cctcttgggc tagcggtaaa ggtgcgcatt ttttcacacc ctacaatgtt ctgttcaaaa   660
gattttggtc aaacgctgta gaagtgaaag ttggtgcgca tgtttcggcg ttcgaaactt   720
ctccgcagtg aaagataaat gatctgaagg ggatgaaaag gaaggtttta gagctagaaa   780
tagcaagtta aaataaggct agtccgttat caacttgaaa aagtggcacc gagtcggtgg   840
tgctttttttt gttttttatg tct                                          863
```

<210> SEQ ID NO 7
<211> LENGTH: 84
<212> TYPE: DNA
<213> ORGANISM: Artificial
<220> FEATURE:
<223> OTHER INFORMATION: Genome modification primers and gBlocks
ABD1.recode+gRNA.int.F

<400> SEQUENCE: 7

```
tatgttgtgc cattcgaaac cttaagaagt ttggctgatg aatacggttt ggaactagta    60
agccagatgc cattcaacaa gttc                                           84
```

<210> SEQ ID NO 8
<211> LENGTH: 88
<212> TYPE: DNA
<213> ORGANISM: Artificial
<220> FEATURE:
<223> OTHER INFORMATION: Genome modification primers and gBlocks
ABD1.recode+gRNA.int.R

<400> SEQUENCE: 8

```
gtaatacggc cgaaatacag atgctttata gtagggttat tgtttctatt cattttatt     60
agacataaaa aacaaaaaaa gcaccacc                                       88
```

<210> SEQ ID NO 9
<211> LENGTH: 388
<212> TYPE: DNA
<213> ORGANISM: Artificial
<220> FEATURE:
<223> OTHER INFORMATION: Genome modification primers and gBlocks
ADE2.gRNA

<400> SEQUENCE: 9

```
tctttgaaaa gataatgtat gattatgctt tcactcatat ttatacagaa acttgatgtt    60
ttctttcgag tatatacaag gtgattacat gtacgtttga agtacaactc tagattttgt   120
agtgccctct tgggctagcg gtaaaggtgc gcattttttc acaccctaca atgttctgtt   180
```

```
caaaagattt tggtcaaacg ctgtagaagt gaaagttggt gcgcatgttt cggcgttcga    240
aacttctccg cagtgaaaga taaatgatca cttgaagatt ctttagtgtg ttttagagct    300
agaaatagca agttaaaata aggctagtcc gttatcaact tgaaaaagtg gcaccgagtc    360
ggtggtgctt tttttgtttt ttatgtct                                      388
```

```
<210> SEQ ID NO 10
<211> LENGTH: 90
<212> TYPE: DNA
<213> ORGANISM: Artificial
<220> FEATURE:
<223> OTHER INFORMATION: Genome modification primers and gBlocks
      ADE2.1.silent.seed.90mer.F

<400> SEQUENCE: 10
tgatgtgcta acgattgaga ttgagcatgt tgatgttcct accctgaaaa acctgcaagt     60
aaaacatccc aaattaaaaa tttacccttc                                     90
```

```
<210> SEQ ID NO 11
<211> LENGTH: 90
<212> TYPE: DNA
<213> ORGANISM: Artificial
<220> FEATURE:
<223> OTHER INFORMATION: Genome modification primers and gBlocks

<400> SEQUENCE: 11
gaagggtaaa ttttaattt gggatgtttt acttgcaggt ttttcagggt aggaacatca      60
acatgctcaa tctcaatcgt tagcacatca                                     90
```

```
<210> SEQ ID NO 12
<211> LENGTH: 30
<212> TYPE: DNA
<213> ORGANISM: Artificial
<220> FEATURE:
<223> OTHER INFORMATION: Genome modification primers and gBlocks
      ABD1.ver.F

<400> SEQUENCE: 12
atagataatg ttcctgaata tgttgtgcca                                     30
```

```
<210> SEQ ID NO 13
<211> LENGTH: 32
<212> TYPE: DNA
<213> ORGANISM: Artificial
<220> FEATURE:
<223> OTHER INFORMATION: Genome modification primers and gBlocks
      ABD1.ver.R

<400> SEQUENCE: 13
ttactacata tagaagtctt gtaatacggc cg                                  32
```

```
<210> SEQ ID NO 14
<211> LENGTH: 29
<212> TYPE: DNA
<213> ORGANISM: Artificial
<220> FEATURE:
<223> OTHER INFORMATION: Genome modification primers and gBlocks
      ABD1.ver.F

<400> SEQUENCE: 14
gctacgaacc gggtaatact aagtgattg                                      29
```

```
<210> SEQ ID NO 15
<211> LENGTH: 31
```

<210> SEQ ID NO 15
<211> LENGTH: 31
<212> TYPE: DNA
<213> ORGANISM: Artificial
<220> FEATURE:
<223> OTHER INFORMATION: Genome modification primers and gBlocks ABD1.ver.R

<400> SEQUENCE: 15
caggtaatta ttccttgctt cttgttactg g                          31

<210> SEQ ID NO 16
<211> LENGTH: 31
<212> TYPE: DNA
<213> ORGANISM: Artificial
<220> FEATURE:
<223> OTHER INFORMATION: qPCR Primer ade2.WT.qPCR.F

<400> SEQUENCE: 16
tacgaaccgg gtaatactaa gtgattgact c                          31

<210> SEQ ID NO 17
<211> LENGTH: 23
<212> TYPE: DNA
<213> ORGANISM: Artificial
<220> FEATURE:
<223> OTHER INFORMATION: qPCR Primer ade2.gRNA.qPCR.R

<400> SEQUENCE: 17
cgctagccca agagggcact aca                                   23

<210> SEQ ID NO 18
<211> LENGTH: 34
<212> TYPE: DNA
<213> ORGANISM: Artificial
<220> FEATURE:
<223> OTHER INFORMATION: qPCR Primers ade2.WT.qPCR.R

<400> SEQUENCE: 18
taccaactgt tctagaatcc atacttgatt gttt                       34

<210> SEQ ID NO 19
<211> LENGTH: 31
<212> TYPE: DNA
<213> ORGANISM: Artificial
<220> FEATURE:
<223> OTHER INFORMATION: qPCR Primer URA3.genedrive.ade2.WT.qPCR.F

<400> SEQUENCE: 19
tacgaaccgg gtaatactaa gtgattgact c                          31

<210> SEQ ID NO 20
<211> LENGTH: 32
<212> TYPE: DNA
<213> ORGANISM: Artificial
<220> FEATURE:
<223> OTHER INFORMATION: qPCR Primer URA3.genedrive.ade2.WT.qPCR.R

<400> SEQUENCE: 20
cctcctaata taccaactgt tctagaatcc at                         32

<210> SEQ ID NO 21
<211> LENGTH: 30
<212> TYPE: DNA
<213> ORGANISM: Artificial
<220> FEATURE:
<223> OTHER INFORMATION: qPCR Primer URA3.genedrive. ade2.gRNA.qPCR.R

<400> SEQUENCE: 21

```
aaacttctcc gcagtgaaag ataaatgatc                                          30

<210> SEQ ID NO 22
<211> LENGTH: 30
<212> TYPE: DNA
<213> ORGANISM: Artificial
<220> FEATURE:
<223> OTHER INFORMATION: qPCR Primers ABD1_rec_qPCR.R

<400> SEQUENCE: 22
cgaggagccg ttcaatttgg tttaactgac                                          30

<210> SEQ ID NO 23
<211> LENGTH: 21
<212> TYPE: DNA
<213> ORGANISM: Artificial
<220> FEATURE:
<223> OTHER INFORMATION: qPCR Primer ABD1_rec_qPCR.F

<400> SEQUENCE: 23
agatgcgtga ggggcttcag c                                                   21

<210> SEQ ID NO 24
<211> LENGTH: 20
<212> TYPE: DNA
<213> ORGANISM: Artificial
<220> FEATURE:
<223> OTHER INFORMATION: qPCR Primer ABD1_WT_qPCR (JDwt1.4).F

<400> SEQUENCE: 24 gaagggatg aaaaggaagc                                                      20

<210> SEQ ID NO 25
<211> LENGTH: 20
<212> TYPE: DNA
<213> ORGANISM: Artificial
<220> FEATURE:
<223> OTHER INFORMATION: qPCR Primer ABD1_WT_qPCR (JDwt1.3).R

<400> SEQUENCE: 25
cgctttccgg ttcgatatac                                                     20

<210> SEQ ID NO 26
<211> LENGTH: 25
<212> TYPE: DNA
<213> ORGANISM: Artificial
<220> FEATURE:
<223> OTHER INFORMATION: qPCR Primer ACT1.qPCR.F

<400> SEQUENCE: 26
cgaaagattc agagccccag aagct                                               25

<210> SEQ ID NO 27
<211> LENGTH: 26
<212> TYPE: DNA
<213> ORGANISM: Artificial
<220> FEATURE:
<223> OTHER INFORMATION: qPCR Primer ACT1.qPCR.R

<400> SEQUENCE: 27
cggtgatttc cttttgcatt ctttcg                                              26

<210> SEQ ID NO 28
<211> LENGTH: 80
<212> TYPE: DNA
```

```
<213> ORGANISM: Artificial
<220> FEATURE:
<223> OTHER INFORMATION: Guide RNA Figure 1A

<400> SEQUENCE: 28
uuuucguggc ugagccacgg ugaaaaaguu caacuauugc cugaucggaa uaaaauugaa      60
cgauaaagau cgagauuuug                                                  80
```